United States Patent
Lukhtanov et al.

(10) Patent No.: US 6,972,339 B2
(45) Date of Patent: Dec. 6, 2005

(54) COMPOUNDS AND METHODS FOR FLUORESCENT LABELING

(75) Inventors: Eugeny A. Lukhtanov, Bothell, WA (US); Alexei V. Vorobiev, Bothell, WA (US); Michael W. Reed, Seattle, WA (US); Nicolaas M. J. Vermeulen, Woodinville, WA (US)

(73) Assignee: Epoch Biosciences, Inc., Bothell, WA (US)

( * ) Notice: Subject to any disclaimer, the term of this patent is extended or adjusted under 35 U.S.C. 154(b) by 537 days.

(21) Appl. No.: 10/026,374

(22) Filed: Dec. 21, 2001

(65) Prior Publication Data

US 2005/0171340 A1    Aug. 4, 2005

Related U.S. Application Data

(60) Provisional application No. 60/317,875, filed on Sep. 7, 2001.

(51) Int. Cl.$^7$ ................................................. C07F 9/24
(52) U.S. Cl. .......................................... 558/91; 558/93
(58) Field of Search ..................... 558/91, 93

(56) References Cited

U.S. PATENT DOCUMENTS

| | | |
|---|---|---|
| 5,187,288 A | 2/1993 | Kang et al. |
| 5,188,934 A | 2/1993 | Menchen et al. |
| 5,221,611 A | 6/1993 | Stenglein et al. |
| 5,227,487 A | 7/1993 | Haugland et al. |
| 5,248,782 A | 9/1993 | Haugland et al. |
| 5,262,530 A | 11/1993 | Andrus et al. |
| 5,304,645 A | 4/1994 | Klein et al. |
| 5,419,966 A | 5/1995 | Reed et al. |
| 5,433,896 A | 7/1995 | Kang et al. |
| 5,442,045 A | 8/1995 | Haugland et al. |
| 5,451,463 A | 9/1995 | Nelson et al. |
| 5,512,667 A | 4/1996 | Reed et al. |
| 5,556,959 A | 9/1996 | Brush et al. |
| 5,583,236 A | 12/1996 | Brush |
| 5,589,586 A | 12/1996 | Holmberg |
| 5,696,251 A | 12/1997 | Arnold, Jr. et al. |
| 5,739,386 A | 4/1998 | Holmes |
| 5,808,044 A | 9/1998 | Brush et al. |
| 5,942,610 A | 8/1999 | Nelson et al. |
| 5,986,086 A | 11/1999 | Brush et al. |
| 6,020,481 A | 2/2000 | Benson et al. |
| 6,162,931 A | 12/2000 | Gee et al. |
| 6,221,604 B1 | 4/2001 | Upadhya et al. |
| 6,660,845 B1 | 12/2003 | Gall et al. |
| 6,683,173 B2 | 1/2004 | Dempcy et al. |

FOREIGN PATENT DOCUMENTS

| | | |
|---|---|---|
| WO | WO 01/64958 A2 | 9/2001 |
| WO | WO 03/023357 A2 | 3/2003 |
| WO | WO 03/107144 A2 | 12/2003 |

OTHER PUBLICATIONS

Theisen et al, Tetrahedron Letters, vol. 33, No. 35, p. 5033-5036 (1992).*

* cited by examiner

*Primary Examiner*—Bernard Dentz
(74) *Attorney, Agent, or Firm*—Townsend and Townsend and Crew LLP

(57) ABSTRACT

Dye reagents useful in labeling biological materials are provided along with methods for their use.

8 Claims, No Drawings

COMPOUNDS AND METHODS FOR FLUORESCENT LABELING

CROSS-REFERENCES TO RELATED APPLICATIONS

This application claims the benefit of U.S. Provisional Application Ser. No. 60/317,875, filed Sep. 7, 2001 entitled "Compounds and Methods for Fluorescent Labeling", the contents of which are incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

BACKGROUND OF THE INVENTION

The non-radioactive detection of biological analytes is an important technology in modern analytical biotechnology. By eliminating the need for radioactive labels, safety is enhanced and the environmental impact of reagent disposal is greatly reduced, resulting in decreased costs for analysis. Examples of methods utilizing such non-radioactive detection methods include DNA sequencing, oligonucleotide probe methods, detection of polymerase-chain-reaction products, immunoassays, and the like.

In many applications the independent detection of multiple spatially overlapping analytes in a mixture is required, e.g., single-tube multiplex DNA probe assays, immuno assays, multicolor DNA sequencing methods, and the like. In the case of multi-loci DNA probe assays, by providing multicolor detection, the number of reaction tubes may be reduced thereby simplifying the experimental protocols and facilitating the manufacturing of application-specific kits. In the case of automated DNA sequencing, multicolor labeling allows for the analysis of all four bases in a single lane thereby increasing throughput over single-color methods and eliminating uncertainties associated with inter-lane electrophoretic mobility variations.

Multiplex detection imposes a number of severe constraints on the selection of dye labels, particularly for analyses requiring an electrophoretic separation and treatment with enzymes, e.g., DNA sequencing.

Due to the variety of constraints imposed of the labeling of biological materials, methodology that is broadly applicable to a variety of dyes is highly desirable. Surprisingly, the present invention provides such methodology, along with reagents that are useful in carrying out labeling processes.

BRIEF SUMMARY OF THE INVENTION

In a broad sense, the present invention provides a method for preparing a fluorescent dye-labeled biological agent, the method comprising contacting an unlabeled biological agent with a fluorescent dye-fused lactone derivative under conditions sufficient to covalently attach the fluorescent dye to said biological agent and form a fluorescent dye-labeled biological agent. In a related aspect, the lactone dyes can be used to prepare phosphoramidite reagents suitable for labeling biological agents or materials in, for example, automated synthesizers.

The fluorescent dye-fused lactone derivatives are generally provided as having the formula selected from the group consisting of:

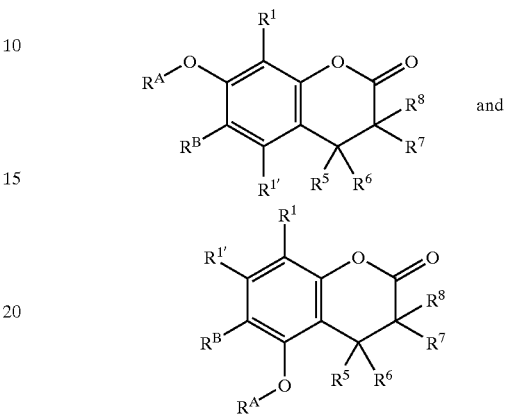

and wherein $R^1$ and $R^{1'}$ are each independently selected from H, halogen, cyano, $CF_3$, $(C_1-C_8)$alkyl, $(C_1-C_8)$alkylthio, $(C_1-C_8)$alkoxy, aryl and heteroaryl; $R^5$, $R^6$, $R^7$ and $R^8$ are each independently selected from H, $(C_1-C_8)$alkyl, aryl, heteroaryl, aryl$(C_1-C_4)$alkyl and heteroaryl$(C_1-C_4)$alkyl; wherein the alkyl portions of any of $R^1$, $R^{1'}$, and $R^1$ through $R^8$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and the aryl or heteroaryl portions of any of $R^1$, $R^{1'}$, and $R^5$ through $R^8$ are optionally substituted with from one to four substituents selected from the group consisting of halogen, cyano, carboxy, sulfo, hydroxy, amino, mono- or di$(C_1-C_6)$alkylamino, $(C_1-C_6)$alkyl, $(C_1-C_6)$alkylthio and $(C_1-C_6)$alkoxy; $R^A$ and $R^B$ are combined to form a substituted or unsubstituted fused ring system having from 1 to 4 five- or six-membered rings; with the proviso that the compound has an emission wavelength of from 400 nm to 1200 nm.

Preferred fluorescent dye-fused lactone derivatives are based on known dyes selected from the coumarins, benzocoumarins, xanthenes, benzo[a]xanthenes, benzo[b]xanthenes, benzo[c]xanthenes, phenoxazines, benzo[a]phenoxazines, benzo[b]phenoxazines and benzo[c]phenoxazines.

Additional reagents and methods are provided in which the lactone dyes are converted to phosphoramidite reagents as well as solid support bound labels useful in fluorescent labeling processes.

The reagents provided herein are stable and in many instances are provided with certain protecting groups that provide the reagent with a long shelf life, making them useful to those engaged in a variety of research efforts.

BRIEF DESCRIPTION OF THE DRAWINGS

Not applicable.

DETAILED DESCRIPTION OF THE INVENTION

Abbreviations and Definitions

Unless otherwise stated, the following terms used in the specification and claims have the meanings given below:

The term "alkyl" refers to a linear, branched, or cyclic saturated monovalent hydrocarbon radical or a combination of cyclic and linear or branched saturated monovalent hydrocarbon radicals having the number of carbon atoms indicated in the prefix. For example, ($C_1$–$C_8$)alkyl is meant to include methyl, ethyl, n-propyl, 2-propyl, tert-butyl, pentyl, cyclopentyl, cyclopropylmethyl and the like. For each of the definitions herein (e.g., alkyl, alkenyl, alkoxy, arylalkoxy), when a prefix is not included to indicate the number of main chain carbon atoms in an alkyl portion, the radical or portion thereof will have eight or fewer main chain carbon atoms.

The term "alkylene" means a linear saturated divalent hydrocarbon radical or a branched saturated divalent hydrocarbon radical having the number of carbon atoms indicated in the prefix. For example, ($C_1$–$C_6$)alkylene is meant to include methylene, ethylene, propylene, 2-methylpropylene, pentylene, and the like.

The term "alkenyl" refers to a linear monovalent hydrocarbon radical or a branched monovalent hydrocarbon radical having the number of carbon atoms indicated in the prefix and containing at least one double bond. For example, ($C_2$–$C_6$)alkenyl is meant to include, ethenyl, propenyl, and the like.

The term "alkynyl" refers to a linear monovalent hydrocarbon radical or a branched monovalent hydrocarbon radical containing at least one triple bond and having the number of carbon atoms indicated in the prefix. For example, ($C_2$–$C_6$)alkynyl is meant to include ethynyl, propynyl, and the like.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Similarly, the term dialkylamino refers to an amino group having two attached alkyl groups that can be the same or different.

The term "aryl" means a monovalent monocyclic or bicyclic aromatic hydrocarbon radical of 6 to 10 ring atoms which is unsubstituted or substituted independently with one to four substituents, preferably one, two, or three substituents selected from alkyl, cycloalkyl, cycloalkyl-alkyl, halo, cyano, hydroxy, alkoxy, amino, acylamino, mono-alkylamino, di-alkylamino, haloalkyl, haloalkoxy, heteroalkyl, COR (where R is hydrogen, alkyl, cycloalkyl, cycloalkylalkyl cut, phenyl or phenylalkyl, aryl or arylalkyl), —(CR'R")$_n$—COOR (where n is an integer from 0 to 5, R' and R" are independently hydrogen or alkyl, and R is hydrogen, alkyl, cycloalkyl, cycloalkylalkyl cut, phenyl or phenylalkyl aryl or arylalkyl) or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl, aryl or arylalkyl). More specifically the term aryl includes, but is not limited to, phenyl, biphenyl, 1-naphthyl, and 2-naphthyl, and the substituted forms thereof. Similarly, the term "heteroaryl" refers to those aryl groups wherein one or more heteroatoms or heteroatom functional groups have replaced a ring carbon, while retaining aromatic properties, e.g., pyridyl, quinolinyl, quinazolinyl, thienyl, and the like. For brevity, the term aryl, when used in combination with other radicals (e.g., aryloxy, arylalkyl) is meant to include both aryl groups and heteroaryl groups as described above.

The term "arylalkyl" refers to a radical —R$^a$R$^b$ where R$^a$ is an alkylene group (having the indicated number of carbon atoms, or if unspecified having six or fewer main chain carbon atoms) and R$^b$ is an aryl group as defined herein. Examples of arylalkyl groups include benzyl, phenylethyl, 3-(3-chlorophenyl)-2-methylpentyl, and the like.

Similarly the term "arylalkenyl" means a radical —R$^a$R$^b$ where R$^a$ is an alkenylene group and R$^b$ is an aryl group as defined herein, e.g., 3-phenyl-2-propenyl, and the like.

"Arylheteroalkyl" means a radical —R$^a$R$^b$ where R$^a$ is an heteroalkylene group (having the indicated number of carbon atoms) and R$^b$ is an aryl group as defined herein, e.g., 2-hydroxy-2-phenyl-ethyl, 2-hydroxy-1-hydroxymethyl-2-phenyl-ethyl, and the like.

The term "aryloxy", refers to a radical —OR where R is an aryl group, e.g., phenoxy, naphthyloxy and the like.

The prefix "halo" and the term "halogen" when used to describe a substituent, refer to —F, —Cl, —Br and —I.

The term "heteroalkyl" refers to an alkyl radical as defined herein with one, two or three substituents independently selected from cyano, —OR$^a$, —NR$^b$R$^c$, and —S(O)$_n$R$^d$ (where n is an integer from 0 to 2), with the understanding that the point of attachment of the heteroalkyl radical is through a carbon atom of the heteroalkyl radical. R$^a$ is hydrogen, alkyl, aryl, arylalkyl, alkoxycarbonyl, aryloxycarbonyl, carboxamido, or mono- or di-alkylcarbamoyl. R$^b$ is hydrogen, alkyl, aryl or arylalkyl. R$^c$ is hydrogen, alkyl, aryl, arylalkyl, alkoxycarbonyl, aryloxycarbonyl, carboxamido, mono- or di-alkylcarbamoyl or alkylsulfonyl. R$^d$ is hydrogen (provided that n is 0), alkyl, aryl, arylalkyl, amino, mono-alkylamino, di-alkylamino, or hydroxyalkyl. Representative examples include, for example, 2-hydroxyethyl, 2,3-dihydroxypropyl, 2-methoxyethyl, benzyloxymethyl, 2-cyanoethyl, and 2-methylsulfonyl-ethyl. For each of the above, R$^a$, R$^b$, R$^c$, and R$^d$ can be further substituted by NH$_2$, fluorine, alkylamino, di-alkylamino, OH or alkoxy. Additionally, the prefix indicating the number of carbon atoms (e.g., $C_1$–$C_{10}$) refers to the total number of carbon atoms in the portion of the heteroalkyl group exclusive of the cyano, —OR$^a$, —NR$^b$R$^c$, or —S(O)$_n$R$^d$ portions.

The term "heterocyclic" refers to a saturated or unsaturated non-aromatic cyclic radical of 3 to 8 ring atoms in which one or two ring atoms are heteroatoms selected from O, NR (where R is independently hydrogen or alkyl) or S(O)$_n$ (where n is an integer from 0 to 2), the remaining ring atoms being C, where one or two C atoms may optionally be replaced by a carbonyl group. The heterocyclyl heterocyclic ring may be optionally substituted independently with one, two, or three substituents selected from alkyl, halo, cyano, hydroxy, alkoxy, amino, mono-alkylamino, di-alkylamino, haloalkyl, haloalkoxy, COR (where R is hydrogen, alkyl, cycloalkyl, cycloalkyl-alkyl cut, phenyl or phenylalkyl aryl or arylalkyl), —(CR'R")$_n$—COOR (n is an integer from 0 to 5, R' and R" are independently hydrogen or alkyl, and R is hydrogen, alkyl, cycloalkyl, cycloalkyl-alkyl cut, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, phenyl or phenylalkyl). More specifically the term heterocyclyl heterocyclic includes, but is not limited to, tetrahydropyranyl, piperidino, N-methylpiperidin-3-yl, piperazino, N-methylpyrrolidin-3-yl, 3-pyrrolidino, 2-pyrrolidon-1-yl, morpholino, thiomorpholino, thiomorpholino-1-oxide, thiomorpholino-1,1-dioxide, pyrrolidinyl, and the derivatives thereof. The prefix indicating the number of carbon atoms (e.g., $C_3$–$C_{10}$) refers to the total number of carbon atoms in the portion of the heterocyclyl heterocyclic group exclusive of the number of heteroatoms.

The terms "heteroalkylene" means a linear saturated divalent hydrocarbon radical of one to six carbons or a branched saturated hydrocarbon radical of three to six carbon atoms with one, two or three substituents independently selected from —OR$^a$, —NR$^b$R$^c$, and —S(O)$_n$R$^d$ (where n is an integer from 0 to 2) where, R$^a$, Rb, R c, and R$^d$ are as defined herein for a heteroalkyl radical. Examples include, 2-hydroxyethan-1,2-diyl, 2-hydroxypropan-1,3-diyl and the like.

Each of the above terms (e.g., "alkyl," "heteroalkyl," and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, heterocycloalkyl, and heterocycloalkenyl) can be a variety of groups selected from: —OR', =O, =NR', =N—OR', —NR'R", —SR', -halogen, —SiR'R"R'", —OC(O)R', —C(O)R', —CO$_2$R', CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to four, preferably, zero, one, two or three substituents. R', R" and R'" each independently refer to hydrogen, unsubstituted (C$_1$-C$_8$)alkyl and heteroalkyl, unsubstituted aryl, aryl substituted with 1–3 halogens, unsubstituted alkyl, alkoxy or thioalkoxy groups, or aryl-(C$_1$-C$_4$)alkyl groups. When R' and R" are attached to the same nitrogen atom, they can be combined with the nitrogen atom to form a 5,6-, or 7-membered ring. For example, —NR'R" is meant to include 1-pyrrolidinyl and 4-morpholinyl. From the above discussion of substituents, one of skill in the art will understand that the term "alkyl" in its broadest sense is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). Preferably, the alkyl groups will have from 0–3 substituents, more preferably 0, 1, or 2 substituents, unless otherwise specified.

Similarly, substituents for the aryl groups are varied and are selected from: -halogen, —OR', —OC(O)R', —NR'R", —SR', —R', —CN, —NO$_2$, —CO$_2$R', —CONR'R", —C(O)R', OC(O)NR'R", —NR"C(O)R', —NR"C(O)$_2$R', —NR'—C(O)NR"R", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R" and R'" are independently selected from hydrogen, (C$_1$-C$^8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl.

Two of the substituents on adjacent atoms of the aryl or heteroaryl ring may optionally be replaced with a substituent of the formula —T—C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula —A—(CH$_2$)$_r$—B—, wherein A and B are independently —CH$_2$—, —O—, —NH—, —S—, —S(O)—, —S(O)$_2$—, —S(O)$_2$NR'- or a single bonds, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, S(O)—, —S(O)$_2$—, or —S(O)$_2$NR'—. The substituent R' in —NR'— and —S(O)$_2$NR'— is selected from hydrogen or unsubstituted (C$_1$-C$_6$) alkyl.

Certain compounds or oligonucleotides of the present invention may exist in a salt form. Such salts include base addition salts such as sodium, potassium, calcium, ammonium, organic amino, or magnesium salt, or a similar salt. When the compounds or modified oligonucleotides of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, lactic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention. The methods for the determination of stereochemistry and the separation of isomers are well-known in the art (see discussion in Chapter 4 of ADVANCED ORGANIC CHEMISTRY, 4th edition J. March, John Wiley and Sons, New York, 1992).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not (e.g., $^2$H), are intended to be encompassed within the scope of the present invention.

"Protecting group" or "protected form thereof" refers to a grouping of atoms that when attached to a reactive group in a molecule masks, reduces or prevents that reactivity. Examples of protecting groups can be found in T. W. Greene and P. G. Wuts, PROTECTIVE GROUPS IN ORGANIC CHEMISTRY, (Wiley, 2nd ed. 1991), Beaucage and Iyer, Tetrahedron 48:2223–2311 (1992), and Harrison and Harrison et al., COMPENDIUM OF SYNTHETIC ORGANIC METHODS, Vols. 1–8 (John Wiley and Sons. 1971–1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like (see also, Boyle, A. L. (Editor), CURRENT PROTOCOLS IN NUCLEIC ACID CHEMISTRY, John Wiley and Sons, New York, Volume 1, 2000). Representative hydroxy protecting groups include those where the hydroxy group is either acylated or alkylated such as benzyl and trityl ethers as well as alkyl ethers, tetrahydropyranyl ethers, trialkylsilyl ethers and allyl ethers. Additionally, hydroxy groups can be protected by photoremovable groups such as α-methyl-6-nitopiperonyloxycarbonyl (McGall, G. H. and Fidanza, J. A., Photolithographic synthesis of high-density olignucleotide arrays, in DNA ARRAYS METHODS AND PROTOCOLS, Edited by Rampal J. B., METHODS IN MOLECULAR BIOLOGY, 170:71–101 (2001), Humana Press, Inc., NY; Boyle, Ann L. (Editor), Current Protocols in Nucleic Acid Chemistry, John Wiley and Sons, New York, Volume 1, 2000.)

"Optional" or "optionally" in the above definitions means that the subsequently described event or circumstance may but need not occur, and that the description includes instances where the event or circumstance occurs and instances in which it does not. For example, "heterocyclo group optionally mono- or di- substituted with an alkyl group" means that the alkyl may but need not be present, and the description includes situations where the heterocyclo group is mono- or disubstituted with an alkyl group and situations where the heterocyclo group is not substituted with the alkyl group.

The term "biological agent" refers to essentially any nucleoside, oligonucleotide, peptide, protein, aminocarbohydrate or ligand, as well as analogs thereof (e.g., oligonucleotides having modified or non-natural bases).

The term "conjugate" refers to a molecule formed by the covalent attachment of two or more components such as oligonucleotides, fluorophores, quenchers, minor groove binders, and the like.

"Oligonucleotide" and "polynucleotide" are used interchangeably and refers to a polymer of nucleotides, either natural or synthetic including, but not limited to those nucleotides having modified bases, sugar analogs, and the like. As noted above, an oligonucleotide conjugate will refer to an oligonucleotide as defined, having at least one covalently attached fluorophore, quencher, minor groove binder (MGB) or other useful fragments, as well as combinations of the recited components.

The term "solid support" refers to essentially any solid or semisolid matrix that is useful for, and compatible with, automated oligonucleotide techniques and includes, glass, polystyrene, nylon, plastic, combinations and the like. Examples of useful solid supports have been described in, for example, U.S. Pat. Nos. 5,262,530, 5,419,966, 5,512,667 and 5,589,586.

The practice of the present invention will employ, unless otherwise indicated, conventional techniques in organic chemistry, biochemistry, oligonucleotide synthesis and modification, bioconjugate chemistry, nucleic acid hybridization, molecular biology, microbiology, genetics, recombinant DNA, and related fields as are within the skill of the art. These techniques are fully explained in the literature. See, for example, Maniatis, Fritsch & Sambrook, MOLECULAR CLONING: A LABORATORY MANUAL, Cold Spring Harbor Laboratory Press (1982); Sambrook, Fritsch & Maniatis, MOLECULAR CLONING: A LABORATORY MANUAL, Second Edition, Cold Spring Harbor Laboratory Press (1989); Ausubel, et al., CURRENT PROTOCOLS IN MOLECULAR BIOLOGY, John Wiley & Sons (1987, 1988, 1989, 1990, 1991, 1992, 1993, 1994, 1995, 1996); Gait (ed.), OLIGONUCLEOTIDE SYNTHESIS: A PRACTICAL APPROACH, IRL Press (1984); Eckstein (ed.), OLIGONUCLEOTIDES AND ANALOGUES: A PRACTICAL APPROACH, IRL Press (1991).

General

The present invention resides in the discovery that a wide variety of fluorescent dyes (or fluorophores) can be prepared having a fused lactone functional group, providing reagents that are shelf-stable and that can be used to label essentially any biological agent (e.g., oligonucleotides, peptides, proteins, probes, and the like) due to their reactivity with suitable preferably nitrogen-containing (like in next scheme) nucleophiles. Accordingly, the invention provides new "lactone dyes" as well as methods of labeling biological agents using these "lactone dyes". The invention further provides reagents such as phosphoramidite-derivatized dyes that can be prepared from the lactone dyes described herein. Additionally, support-bound dyes, similarly prepared from the lactone dyes are also described.

The "lactone dye" approach to labeling as well as reagent (e.g., support-bound dyes and phosphoramidites) has been found to be compatible with, for example, coumarin dyes, benzocoumarin dyes, fluorescein dyes, rhodol dyes, phenoxazine dyes, benzophenoxazine dyes, xanthene dyes, benzoxanthene dyes, and cyanine dyes.

Examples of these and other suitable dye classes can be found in Haugland, et al., HANDBOOK OF FLUORESCENT PROBES AND RESEARCH CHEMICALS, SIXTH ED., Molecular Probes, Eugene, Ore. 1996; U.S. Pat. Nos. 5,187,288; 5,188,934; 5,227,487, 5,248,782; 5,304,645; 5,433,896; 5,442,045; 5,556,959; 5,583,236; 5,808,044; 5,986,086; 6,020,481; 6,162,931; and 6,221,604; Smith, et al., J. Chem. Soc. Perkin Trans. 2, 1993, 1195–1204; Whitaker, et al., Anal. Biochem. 207:267–279 (1992); and Hirschberg, et al., Biochemistry 37:10381–10385 (1998).

EMBODIMENTS OF THE INVENTION

Methods for Labeling Biological Agents

In one aspect, the present invention provides methods for preparing a fluorescent dye-labeled biological agent, the method comprising contacting an unlabeled biological agent with a fluorescent dye-fused lactone derivative under conditions sufficient to covalently attach the fluorescent dye to said biological agent and form a fluorescent dye-labeled biological agent. The term "fluorescent dye-fused lactone derivative" or more simply "lactone dye" as used herein refers to essentially any fluorescent dye which has a fused 5-, 6-, or 7-membered lactone (e.g., shares two carbon atoms and one oxygen with the dye) attached to the dye framework. In most instances below, a lactone is illustrated that is a preferred 6-membered lactone, although the invention is not so limited.

As noted above, the present invention finds broad application in labeling of nucleic acids (including nucleotides, nucleosides, DNA, RNA, PNA, locked nucleic acids, oligonucleotides and the like), peptides or proteins, oligosaccharides, glycosylated proteins, and other biological agents. Additionally, the nucleic acids can include modified bases (e.g., 5-substituted pyrimidines, 3-substituted purines, substituted deazapurines, substituted pyrazolo[3,4-d]pyrimidines, and the like). See, for example, co-pending application Ser. Nos. 09/724,988 and 09/447,936. The invention also finds utility in labeling of oligonucleotides and modified oligonucleotides having attached groups such as minor groove binders, intercalators, crosslinking groups, and the like.

Lactone Dyes

As noted above, the invention is broadly applicable to the preparation and use of new lactone derivatives of a variety of dyes. In many embodiments, lactone derivatives can be prepared based on any dye that can form a chroman-2-one fragment (fused lactone) as illustrated below. Reaction between a nitrogen-containing substrate or biological agent and a lactone forms a covalent bond on ring opening. Of course, one of skill in the art will appreciate that the lactone methodology (e.g., the synthesis of a lactone ring fused to a dye) described herein can be applied to essentially any dye having a ring structure and available valence sites for the lactone ring.

Typically, the nucleophiles are nitrogen nucleophiles (e.g., amines, hydrazines and the like) and the ligand ($R^M$) can be a biological compound (e.g., a nucleic acid, peptide, protein and the like) or a linking group that is used to attached the fluorescent molecule to, for example, a phosphoramidite group or a solid support.

In view of the above, the present invention provides methods for labeling biological materials and methods for preparing phosphoramidite reagents or solid support reagents by reacting a fluorescent dye fused-lactone derivative having a formula selected from:

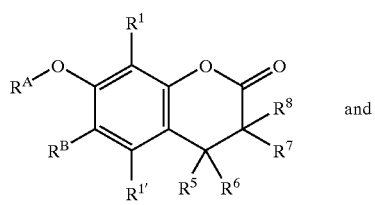

and

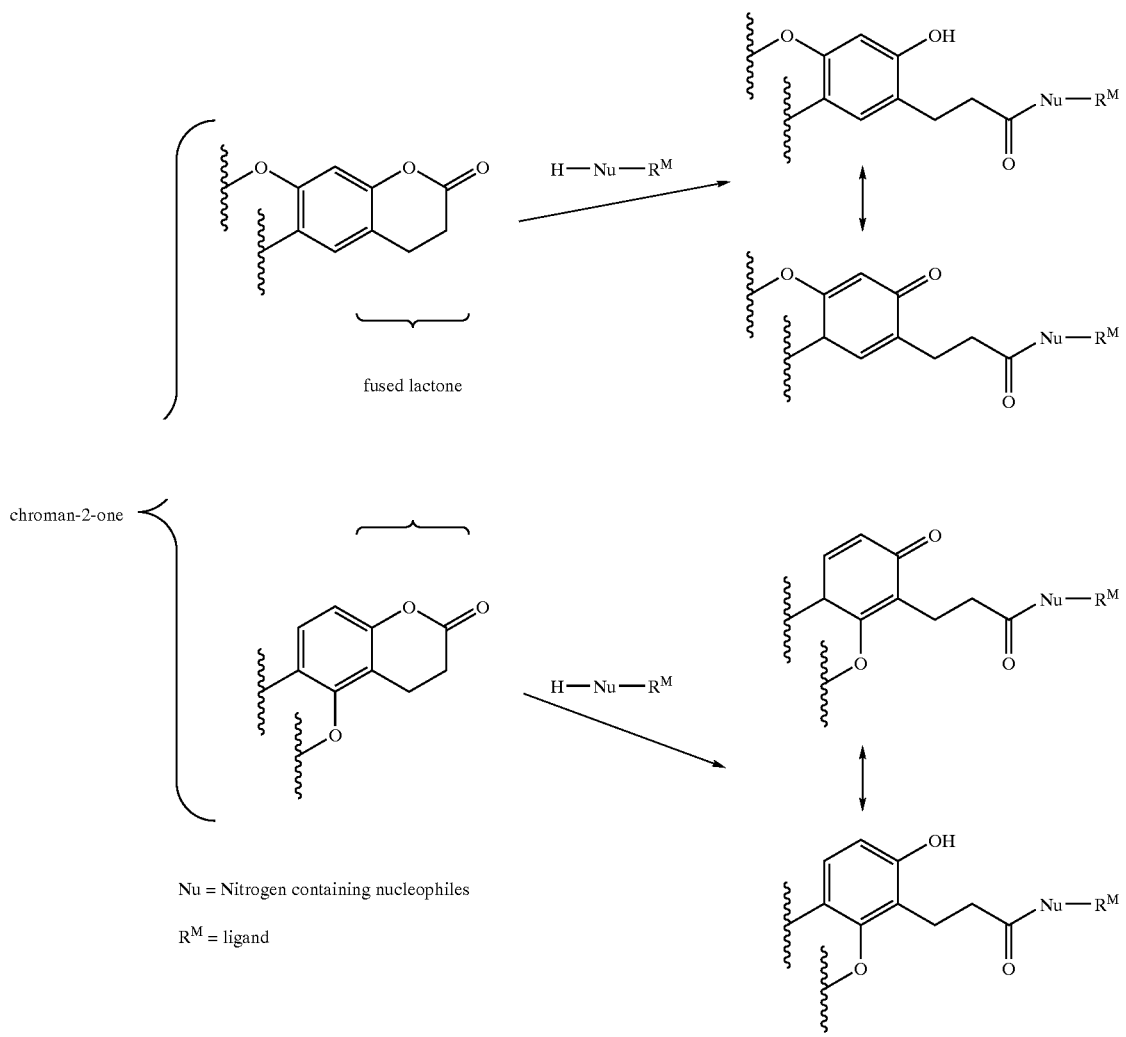

-continued

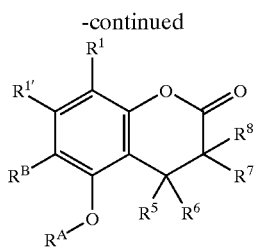

with a suitable nucleophile to attach the fluorescent dye to a linking group, solid support, or biological material. In the above formulae, $R^1$ and $R^{1'}$ are each members independently selected from the group consisting of H, halogen, cyano, $CF_3$, $(C_1–C_8)$alkyl, $(C_1–C_8)$alkylthio, $(C_1–C_8)$alkoxy, aryl and heteroaryl; $R^5$, $R^6$, $R^7$ and $R^8$ are each independently selected from the group consisting of H, $(C_1–C_8)$alkyl, aryl, heteroaryl, aryl$(C_1–C_4)$alkyl and heteroaryl$(C_1–C_4)$alkyl; wherein the alkyl portions of any of $R^1$, $R^{1'}$, or $R^5$ through $R^8$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and the aryl or heteroaryl portions of any of $R^1$, $R^{1'}$, and $R^5$ through $R^8$ are optionally substituted with from one to four substituents selected from the group consisting of halogen, cyano, carboxy, sulfo, hydroxy, amino, mono- or di$(C_1–C_6)$alkylamino, $(C_1–C_6)$alkyl, $(C_1–C_6)$alkylthio and $(C_1–C_6)$alkoxy. Additionally, the symbols $R^A$ and $R^B$ are combined to form a substituted or unsubstituted fused ring system having from 1 to 4 five- or six-membered rings; with the proviso that the compound has an emission wavelength of from 400 nm to 1200 nm, more preferably, 400 nm to about 850 nm.

While the present invention finds broad application to a number of chroman-2-one dyes, certain groups of dyes are preferred and are outlined below.

A. Xanthenes (Fluoresceins and Rhodols)

The methods of the present invention can be carried out using xanthene fused-lactone dyes having the formula:

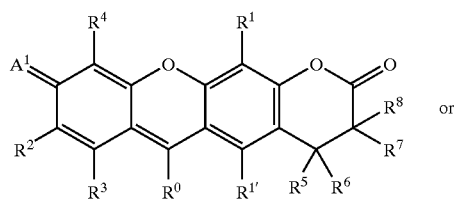

(I)

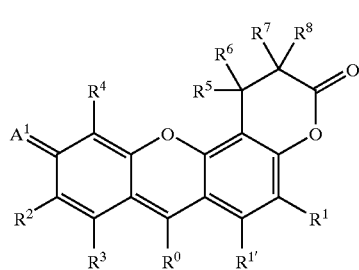

(I')

wherein $A^1$ represents O or N—Z in which Z is H or $(C_1–C_8)$alkyl, or is optionally combined with $R^2$ or $R^4$ to form a 5- or 6-membered ring or is combined with each of $R^2$ and $R^4$ to form two fused 6-membered rings; $R^1$, $R^{1'}$, $R^2$, $R^3$ and $R^4$ are each independently selected from H, halogen, cyano, $CF_3$, $(C_1–C_8)$alkyl, $(C_1–C_8)$alkylthio, $(C_1–C_8)$alkoxy, aryl and heteroaryl; $R^5$, $R^6$, $K^7$ and $R^8$ are each independently selected from the group consisting of H, $(C_1–C_8)$alkyl, aryl, heteroaryl, aryl$(C_1–C_4)$alkyl and heteroaryl$(C_1–C_4)$alkyl; wherein the alkyl portions of any of $R^{1'}$ or $R^1$ through $R^8$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and the aryl or heteroaryl portions of any of $R^{1'}$ and $R^1$ through $R^8$ are optionally substituted with from one to four substituents selected from the group consisting of halogen, cyano, carboxy, sulfo, hydroxy, amino, mono- or di$(C_1–C_6)$alkylamino, $(C_1–C_6)$alkyl, $(C_1–C_6)$alkylthio and $(C_1–C_6)$alkoxy; $R^0$ is halogen, cyano, $CF_3$, $(C_1–C_8)$alkyl, $(C_1–C_8)$alkenyl, $(C_1–C_8)$alkynyl, aryl or heteroaryl having the formula:

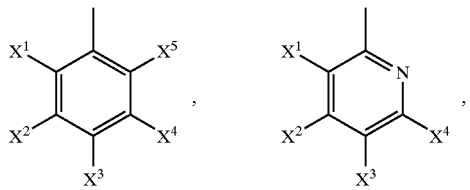

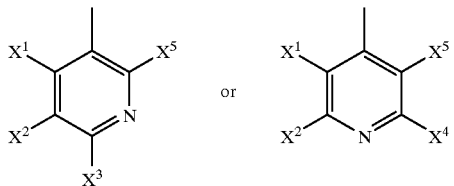

wherein $X^1$, $X^2$, $X^3$, $X^4$ and $X^5$ are each independently selected from the group consisting of H, halogen, cyano, $CF_3$, $(C_1–C_8)$alkyl, $(C_1–C_8)$alkoxy, $(C_1–C_8)$alkylthio, $(C_1–C_8)$alkenyl, $(C_1–C_8)$alkynyl, $SO_3H$ and $CO_2H$. Additionally, the alkyl portions of any of $X^1$ through $X^5$ can be further substituted with halogen, carboxy, sulfo, amino, mono- or dialkylamino, alkoxy, cyano, haloacetyl or hydroxy, and the alkyl portions of the substituents have from 1 to 6 carbon atoms. Optionally, any two adjacent substituents $X^1$ through $X^5$ can be taken together to form a fused aromatic ring that is optionally further substituted with from one to four substituents selected from halogen cyano, carboxy, sulfo, hydroxy, amino, mono- or di$(C_1–C_6)$alkylamino, $(C_1–C_6)$alkyl, $(C_1–C_6)$alkylthio and $(C_1–C_6)$alkoxy.

In certain embodiments, the lactone dyes of formula I (as well as other formulae herein) will be present in isomeric or tautomeric forms (e.g., spirolactones that result from compounds in which $R^0$ is substituted phenyl or pyridyl and $X^5$ is $CO_2H$ or $SO_3H$) and are included in this invention.

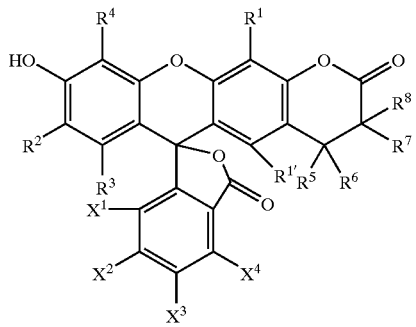
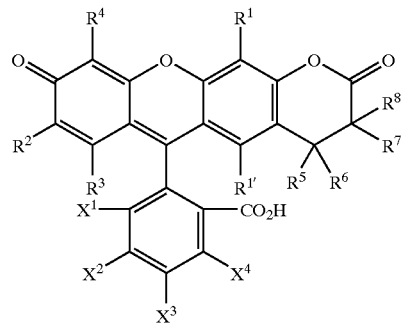

When the tautomeric form has a hydroxy (or amino) group positioned between $R^2$ and $R^4$, protected forms are also contemplated by the present invention. Thus, for those formulae in the present invention wherein $A^1$ is provided as O and NR, the invention further includes those compounds in which A is OH or a protected hydroxy group, and $NH_2$ or a protected amino group.

Accordingly, in one group of preferred embodiments, the xanthene fused-lactone dyes are fluorescein fused-lactone dyes selected from those having one of the following formulae:

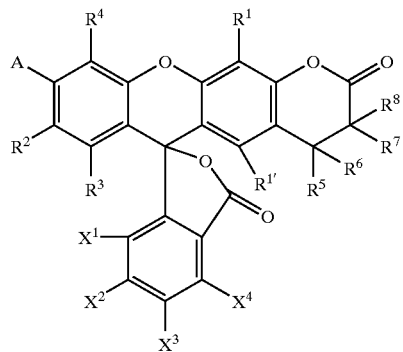

(Ia)

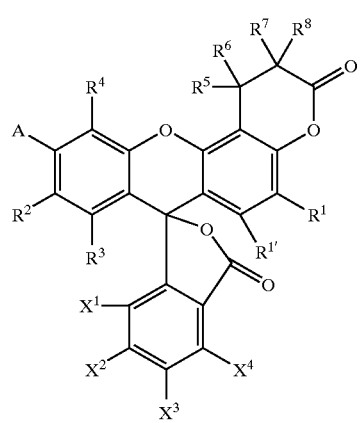

(Ib)

-continued

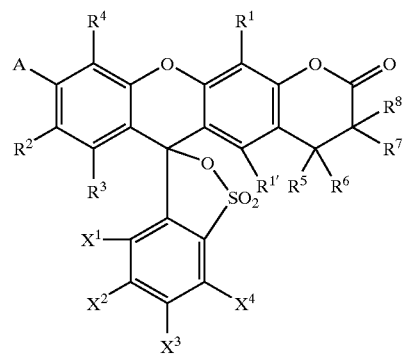

(Ic)

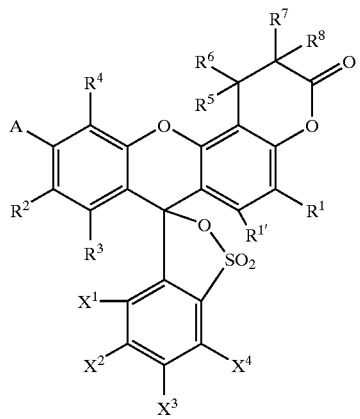

(Id)

wherein A represents a hydroxy, amino, protected hydroxy, or protected amino, or is optionally combined with $R^2$ or $R^4$ to form a 5- or 6-membered ring or is combined with each of R and $R^4$ to form two fused 6-membered rings; $R^{1'}$, $R^1$, $R^2$, $R^3$ and $R^4$ are each independently selected from H, halogen, cyano, $CF_3$, $(C_1-C_8)$alkyl, $(C_1-C_8)$alkylthio and $(C_1-C_8)$alkoxy; $R^5$, $R^6$, $R^7$ and $R^8$ are each independently selected from H, $(C_1-C_8)$alkyl, aryl and aryl$(C_1-C_4)$alkyl; wherein the alkyl portions of any of $R^1$ through $R^8$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and the aryl portions of any of $R^5$ through $R^8$ are optionally substituted with from one to four substituents selected from the group consisting of halogen, cyano, carboxy, sulfo, hydroxy, amino, mono- or di$(C_1-C_6)$ alkylamino, $(C_1–C_6)$alkyl, $(C_1–C_6)$alkylthio and $(C_1–C_6)$alkoxy. Further preferred are those compounds of formulae Ia and Ib wherein A is hydroxy or a protected hydroxy. Preferred protecting groups are acyl groups derived from $(C_2–C_{20})$alkanoic acids (e.g., acetyl, propionyl, pivaloyl, isobutyryl, and the like). Still further preferred are those compounds having a formula above in which $R^{1'}$ and $R^1$ through $R^8$ are independently selected from H, halogen, $CF_3$ and cyano.

The fused-lactone fluorescein dyes of the present invention can generally be prepared according to the scheme below, in which a suitably substituted resorcinol (i) is reacted with a substituted benzophenone (ii), then lactonized to produce the desired compounds (iii). Certain substituents are not included in the formula below. A more detailed reaction scheme and a table of particularly preferred lactone dyes in this group are provided in the section entitled "General Synthesis of Lactone Dyes."

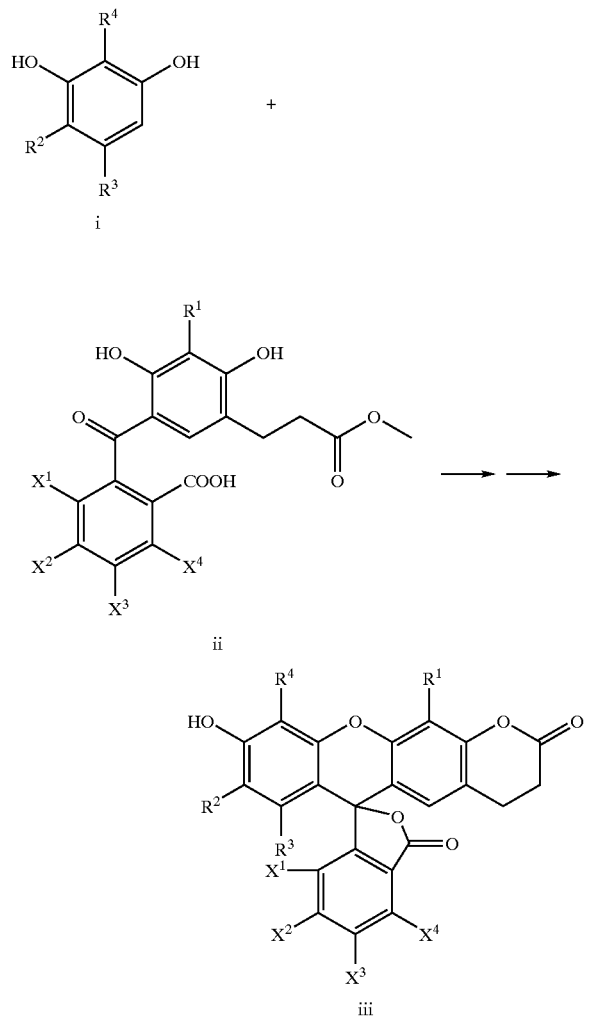

B. Benzo[a]xanthenes

Benzo[a]xanthene fused lactone dyes that are useful in the present methods are provided having the formula:

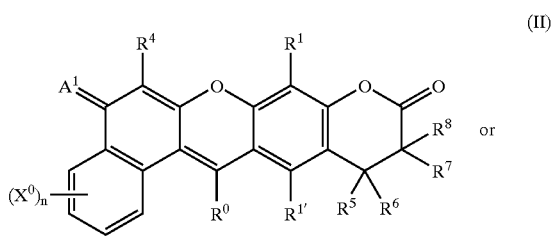

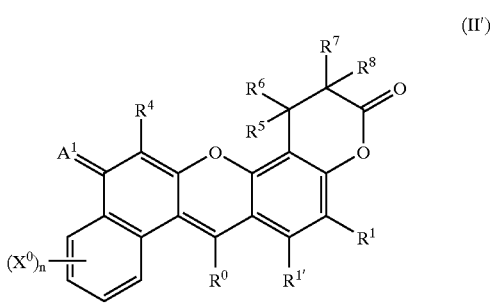

wherein $A^1$ represents O or N—Z in which Z is H or $(C_1–C_8)$alkyl, or is optionally combined with $R^4$ to form a 5- or 6-membered ring; $R^1$, $R^{1'}$ and $R^4$ are each independently selected from H, halogen, cyano, $CF_3$, $(C_1–C_8)$alkyl, $(C_1–C_8)$alkylthio, $(C_1–C_8)$alkoxy, aryl and heteroaryl; the subscript n is 0 to 4 and each $X^0$ is independently selected from the group consisting of H, halogen, cyano, $CF_3$, $(C_1–C_8)$alkyl, $(C_1–C_8)$alkoxy, $(C_1–C_8)$alkylthio, $(C_1–C_8)$alkenyl, $(C_1–C_8)$alkynyl, aryl, heteroaryl, $SO_3H$ and $CO_2H$; $R^5$, $R^6$, $R^7$ and $R^8$ are each independently selected from the group consisting of H, $(C_1–C_8)$alkyl, aryl, heteroaryl, aryl$(C_1–C_4)$alkyl and heteroaryl$(C_1–C_4)$alkyl; wherein the alkyl portions of any of $X^0$, $R^{1'}$ or $R^1$ through $R^8$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and the aryl or heteroaryl portions of any of $X^0$, $R^{1'}$ and $R^1$ through $R^8$ are optionally substituted with from one to four substituents selected from the group consisting of halogen, cyano, carboxy, sulfo, hydroxy, amino, mono- or di$(C_1–C_6)$alkylamino, $(C_1–C_6)$alkyl, $(C_1–C_6)$alkylthio and $(C_1–C_6)$alkoxy; $R^0$ is halogen, cyano, $CF_3$, $(C_1–C_8)$alkyl, $(C_1–C_8)$alkenyl, $(C_1–C_8)$alkynyl, aryl or heteroaryl having the formula:

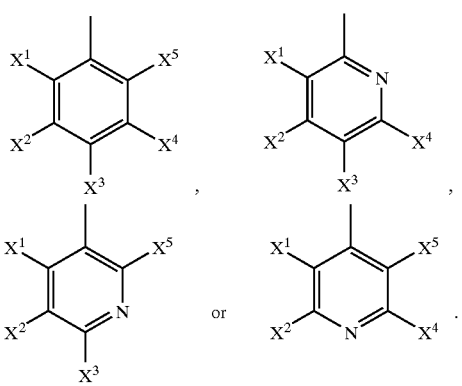

In formula II, as well as the aryl and heteroaryl substituents above, each $X^1$, $X^2$, $X^3$, $X^4$ and $X^5$ is independently selected from the group consisting of H, halogen, cyano, $CF_3$, $(C_1-C_8)$alkyl, $(C_1-C_8)$alkoxy, $(C_1-C_8)$alkylthio, $(C_1-C_8)$alkenyl, $(C_1-C_8)$alkynyl, $SO_3H$ and $CO_2H$. Additionally, the alkyl portions of any of $X^1$ through $X^5$ can be further substituted with halogen, carboxy, sulfo, amino, mono- or dialkylamino, alkoxy, cyano, haloacetyl or hydroxy, and the alkyl portions of the substituents have from 1 to 6 carbon atoms. Optionally, any two adjacent substituents $X^1$ through $X^5$, or two adjacent $X^0$ groups can be taken together to form a fused aromatic ring that is optionally further substituted with from one to four substituents selected from halogen cyano, carboxy, sulfo, hydroxy, amino, mono- or di$(C_1-C_6)$alkylamino, $(C_1-C_6)$alkyl, $(C_1-C_6)$alkylthio and $(C_1-C_6)$alkoxy. The subscript n is an integer of from 0 to 4.

In a preferred group of embodiments, the fused-lactone benzo[a]xanthene dyes are those having a formula:

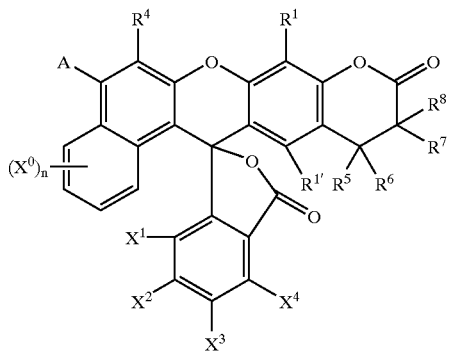

(IIa)

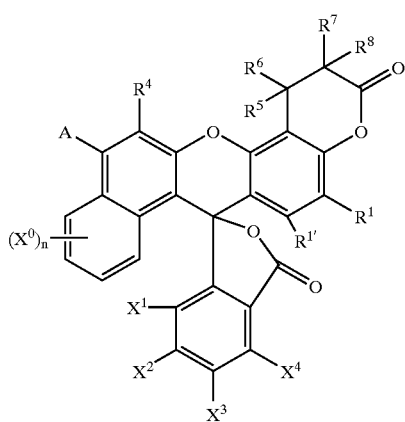

(IIb)

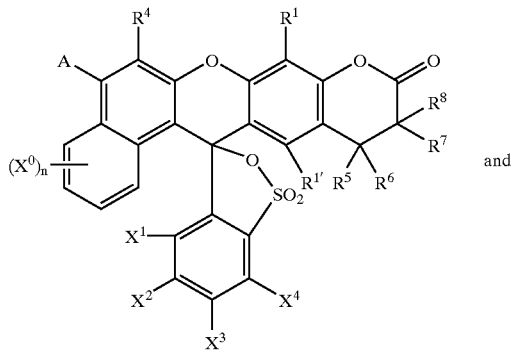

(IIc)

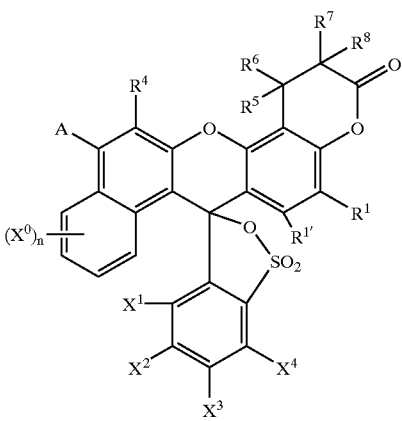

(IId)

wherein A is hydroxy or protected hydroxy, or amino or protected amino; each $X^0$ and n has the meaning given with reference to formula II, and each of $X^1$, $X^2$, $X^3$, $X^4$, $R^1$, $R^{1'}$, $R^4$, and $R^5$ through $R^8$ have the meanings provided above with reference to formulae I. Further preferred are those compounds of formulae IIa and IIc wherein A is hydroxy or a protected hydroxy. Preferred protecting groups are acyl groups derived from $(C_2-C_{20})$alkanoic acids (e.g., acetyl, propionyl, pivaloyl, isobutyryl, and the like). More preferably, $R^{1'}$ and $R^1$ through $R^8$ are independently selected from H, halogen, $CF_3$ and cyano; and each $X^0$ is H, halogen, $CF_3$ or cyano. In other preferred embodiments, two of $X^1$ through $X^4$ are combined to form a six-membered aromatic ring. In other particularly preferred embodiments, in the compounds of IIa and IIc, each of $R^5$ through $R^8$ is H. Most preferred are those embodiments in which A is hydroxy or protected hydroxy; each of $R^5$ through $R^8$ is H; each of $X^1$ through $X^4$ is H, F or Cl; and $R^1$, $R^{1'}$, and $R^4$ are each independently selected from H, F, Cl, CN and $CF_3$.

In general, these compounds can be prepared according to the procedure in Reaction Scheme 2.

Reaction Scheme 2

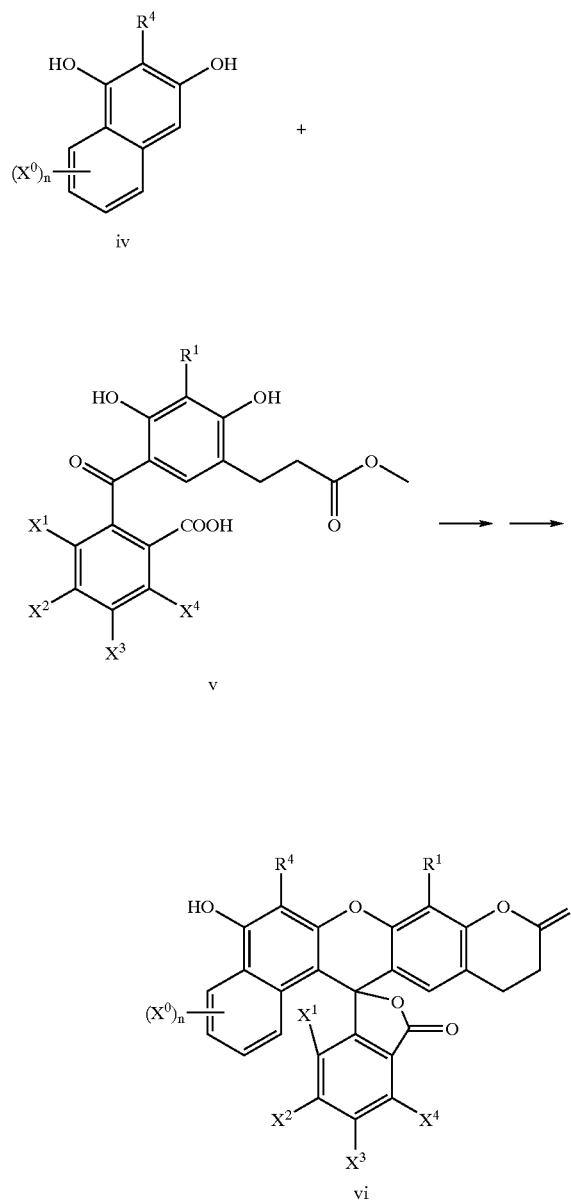

C. Benzo[b]xanthenes

Still other compounds useful in the present invention are the fused-lactone benzo[b]xanthenes provided in formulae (III) and (III') below.

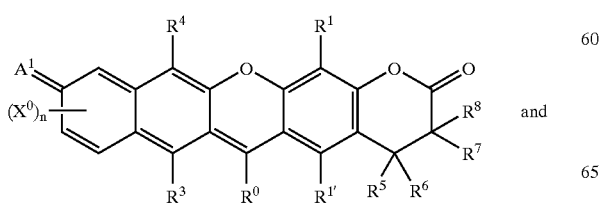

(III)

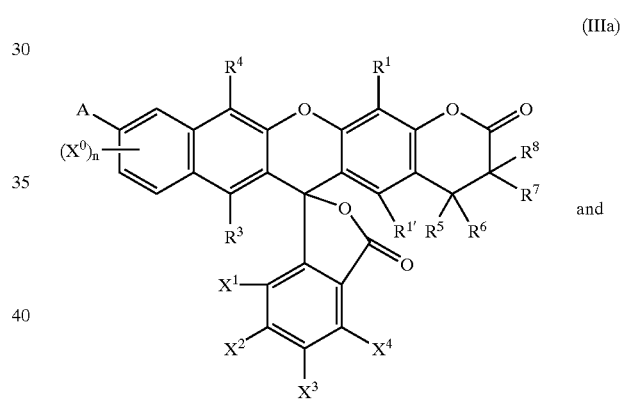

(III')

In each of these formulae, $A^1$, $R^0$ through $R^8$, $X^0$ are as described above with reference to formula II and the subscript n is an integer of from 0 to 3. Optionally $A^1$ can be combined with an adjacent $X^0$ group to form a 5- or 6-membered ring or can be combined with two adjacent $X^0$ groups to form two fused 6-membered rings.

Particularly preferred fused-lactone benzo[b]xanthenes are provided in formula (IIIa) and (IIIb):

(IIIa)

and (IIIb)

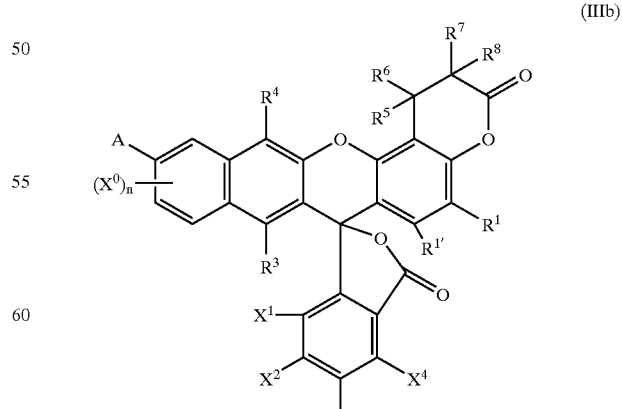

(IIIc)

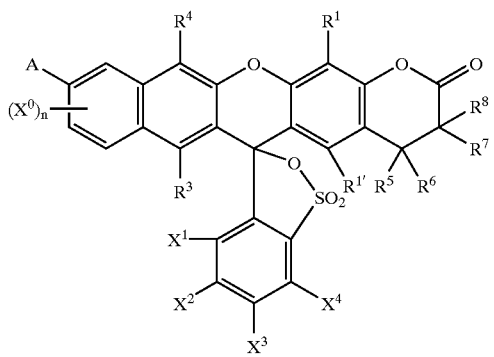

stituents ($X^0$, $X^1$ through $X^4$) have the meanings provided with reference to general formulae III and III'.

In further preferred embodiments, the present methods employ those compounds of formulae IIa or IIIb wherein A is hydroxy or a protected hydroxy. Preferred protecting groups are acyl groups derived from ($C_2$–$C_{20}$)alkanoic acids (e.g., acetyl, propionyl, pivaloyl, isobutyryl, and the like). Still further preferred are those compounds of formulae IIa or IIIb in which $R^{1'}$ and $R^1$ through $R^8$ are independently selected from H, halogen, $CF_3$ and cyano. More preferably, each $X^0$ is H, halogen, $CF_3$ or cyano. In other preferred embodiments, two of $X^1$ through $X^4$ are combined to form a six-membered aromatic or heteroaromatic ring. In other particularly preferred embodiments, in the compounds of IIIa and IIIb, each of $R^5$ through $R^8$ is H.

D. Benzo[c]xanthenes

Still other fused-lactone benzo[c]xanthenes that are useful in the present invention are provided in formulae (IV) and (IV'):

(IIId)

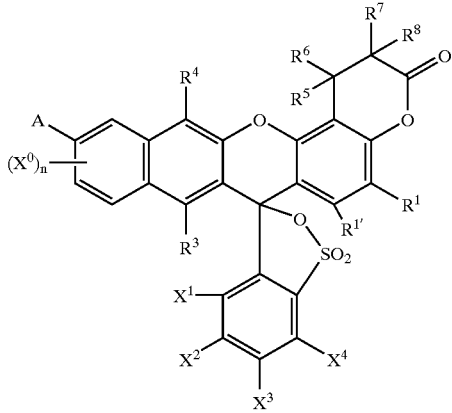

(IV)

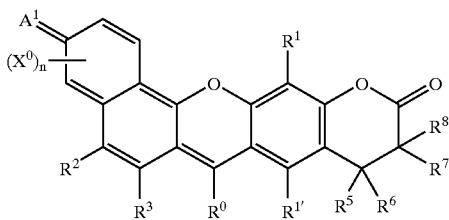

and (IV')

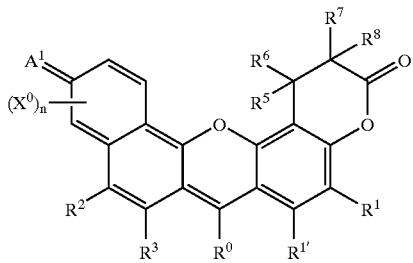

wherein A represents a hydroxy, amino, protected hydroxy, protected amino; $R^{1'}$, $R^1$, $R^3$ and $R^4$ are each independently selected from H, halogen, cyano, $CF_3$, ($C_1$–$C_8$)alkyl, ($C_1$–$C_8$)alkylthio and ($C_1$–$C_8$)alkoxy; $R^5$, $R^6$, $R^7$ and $R^8$ are each independently selected from H, ($C_1$–$C_8$)alkyl, aryl and aryl($C_1$–$C_4$)alkyl; wherein the alkyl portions of any of $R^{1'}$, and $R^1$ through $R^8$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and the aryl portions of any of $R^5$ through $R^8$ are optionally substituted with from one to four substituents selected from the group consisting of halogen, cyano, carboxy, sulfo, hydroxy, amino, mono- or di($C_1$–$C_6$)alkylamino, ($C_1$–$C_6$)alkyl, ($C_1$–$C_6$)alkylthio and ($C_1$–$C_6$)alkoxy. The remaining subwherein $A^1$, $R^0$ through $R^8$ are as described with reference to formula I and $X^0$ and n are as described above with reference to formulae II and III. Optionally $A^1$ can be combined with an adjacent $X^0$ group to form a 5- or 6-membered ring or can be combined with two adjacent $X^0$ groups to form two fused 6-membered rings.

Particularly preferred fused-lactone benzo[b]xanthenes are provided in formulae (IVa) through (IVd):

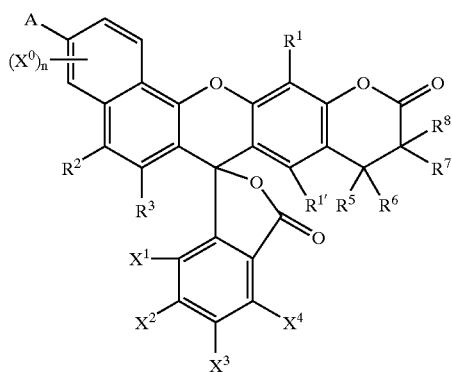

(IVa)

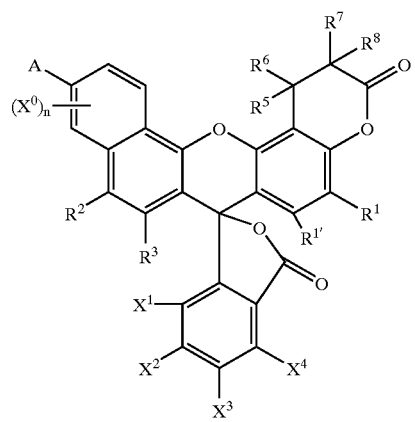

(IVb)

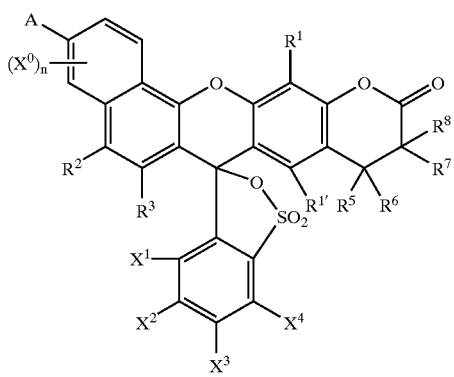

(IVc)

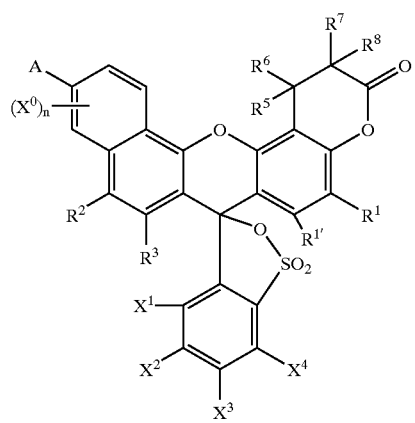

(IVd)

wherein A represents a hydroxy, amino, protected hydroxy, protected amino; $R^{1'}$, $R^1$, $R^2$, $R^3$ and $R^4$ are each independently selected from H, halogen, cyano, $CF_3$, $(C_1-C_8)$alkyl, $(C_1-C_8)$alkylthio and $(C_1-C_8)$alkoxy; $R^5$, $R^6$, $R^7$ and $R^8$ are each independently selected from H, $(C_1-C_8)$alkyl, aryl and aryl$(C_1-C_4)$alkyl; wherein the alkyl portions of any of $R^{1'}$, and $R^1$ through $R^8$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and the aryl portions of any of $R^5$ through $R^8$ are optionally substituted with from one to four substituents selected from the group consisting of halogen, cyano, carboxy, sulfo, hydroxy, amino, mono- or di$(C_1-C_6)$alkylamino, $(C_1-C_6)$alkyl, $(C_1-C_6)$alkylthio and $(C_1-C_6)$alkoxy. The remaining substituents ($X^0$, $X^1$ through $X^4$) have the meanings provided with reference to general formula IV and IV'.

In further preferred embodiments, the present methods employ those compounds of formulae IVa or IVb wherein A is hydroxy or a protected hydroxy. Preferred protecting groups are acyl groups derived from $(C_2-C_{20})$alkanoic acids (e.g., acetyl, propionyl, pivaloyl, isobutyryl, and the like). Still further preferred are those compounds of formulae IVa or IVb in which $R^{1'}$ and $R^1$ through $R^8$ are independently selected from H, halogen, $CF_3$ and cyano. More preferably, each $X^0$ is H, halogen, $CF_3$ or cyano. In other preferred embodiments, two of $X^1$ through $X^4$ are combined to form a six-membered aromatic or heteroaromatic ring. In other particularly preferred embodiments, in the compounds of IVa and IVb, each of $R^5$ through $R^8$ is H.

E. Phenoxazines

In still another group of embodiments, the fused-lactone dyes are represented by the formulae (V) and (V'):

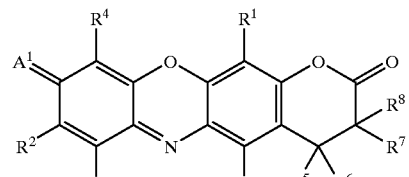

(V)

and

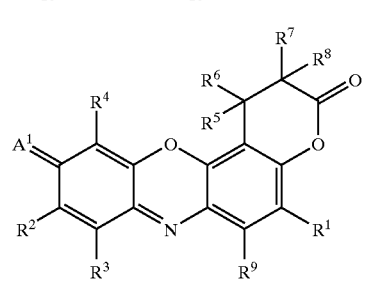

(V')

in which the symbols $A^1$, and $R^1$ through $R^8$ have the meanings provided above with respect to compounds of formula II, III and IV. Optionally $A^1$ can be combined with $R^2$ or $R^4$ to form a 5- or 6-membered ring or can be combined with each of $R^2$ and $R^4$ to form two fused 6-membered rings. Additionally, $R^9$ can be any of the groups provided for $R^{1'}$.

In certain preferred embodiments, $R^1$, $R^2$, $R^3$, $R^4$ and $R^9$ are each independently selected from H, halogen, cyano, $CF_3$, $(C_1-C_8)$alkyl, $(C_1-C_8)$alkylthio and $(C_1-C_8)$alkoxy; $R^5$, $R^6$, $R^7$ and $R^8$ are each independently selected from H, $(C_1-C_8)$alkyl, aryl and aryl$(C_1-C_4)$alkyl; wherein the alkyl portions of any of $R^1$ through $R^9$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and the aryl portions of any of $R^5$ through $R^8$ are optionally substituted with from one to four substituents selected from the group consisting of halogen, cyano, carboxy, sulfo, hydroxy, amino, mono- or di$(C_1-C_6)$alkylamino, $(C_1-C_6)$alkyl, $(C_1-C_6)$alkylthio and $(C_1-C_6)$alkoxy. Still further preferred are those compounds of formula V in which $R^1$ through $R^9$ are independently selected from H, halogen, $CF_3$ and cyano. In other particularly preferred embodiments, in the compounds of V and V', each of $R^5$ through $R^8$ is H and each of $R^1$ through $R^4$ and $R^9$ is independently selected from the group consisting of hydrogen and halogen, more preferably, H, Cl and F.

The fused-lactone phenoxazine dyes of the present invention can generally be prepared according to the scheme below, in which a suitably substituted nitrosoresorcinol (vii) is reacted with a suitably substituted dihydroxy hydrocinnamic acid (viii), then lactonized to produce the desired compounds (ix). Certain substituents are not included in the formula below. A more detailed reaction scheme and a table of particularly preferred lactone dyes in this group are provided in the section entitled "General Synthesis of Lactone Dyes."

Reaction Scheme 3

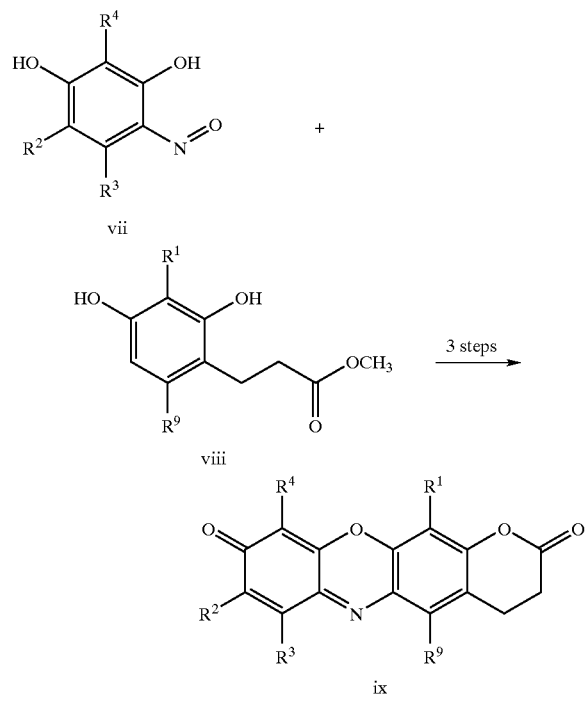

F. Benzo[a]phenoxazines

In a group of related embodiments, the fused lactone dyes are based on the benzo[a]phenoxazine dyes and are represented by the formulae (VI) and (VI'):

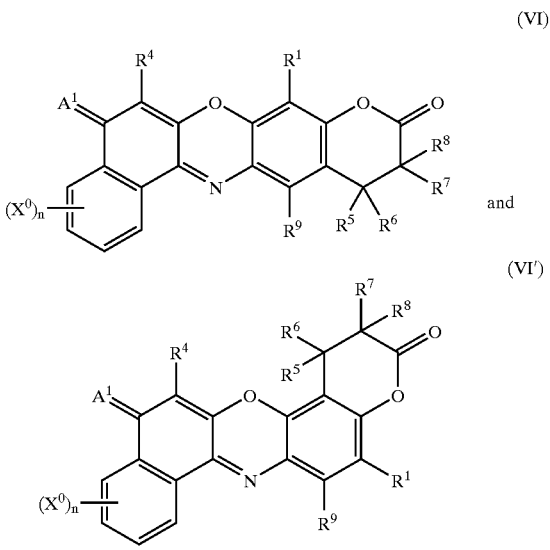

wherein $A^1$ represents O or N—Z in which Z is H or $(C_1-C_8)$alkyl, or is optionally combined with $R^4$ to form a 5- or 6-membered ring; $R^1$, $R^4$ and $R^9$ are each independently selected from H, halogen, cyano, $CF_3$, $(C_1-C_8)$alkyl, $(C_1-C_8)$alkylthio, $(C_1-C_8)$alkoxy, aryl and heteroaryl; $R^5$, $R^6$, $R^7$ and $R^8$ are each independently selected from the group consisting of H, $(C_1-C_8)$alkyl, aryl, heteroaryl, aryl $(C_1-C_4)$alkyl and heteroaryl$(C_1-C_4)$alkyl; wherein the alkyl portions of any of $R^1$ or $R^4$ through $R^9$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and the aryl or heteroaryl portions of any of $R^1$ and $R^4$ through $R^9$ are optionally substituted with from one to four substituents selected from the group consisting of halogen, cyano, carboxy, sulfo, hydroxy, amino, mono- or di$(C_1-C_6)$alkylamino, $(C_1-C_6)$alkyl, $(C_1-C_6)$alkylthio and $(C_1-C_6)$alkoxy; each $X^0$ is independently selected from the group consisting of H, halogen, cyano, $CF_3$, $(C_1-C_8)$alkyl, $(C_1-C_8)$alkoxy, $(C_1-C_8)$alkylthio, $(C_1-C_8)$alkenyl, $(C_1-C_8)$ alkynyl, aryl, heteroaryl, $SO_3H$ and $CO_2H$. Additionally, the alkyl or aryl portions of any $X^0$ can be further substituted with halogen, carboxy, sulfo, amino, mono- or dialkylamino, alkoxy, cyano, haloacetyl or hydroxy, and the alkyl portions of the substituents have from 1 to 6 carbon atoms. Optionally, any two adjacent $X^0$ groups can be taken together to form a fused aromatic or heteroaromatic ring that is optionally further substituted with from one to four substituents selected from halogen cyano, carboxy, sulfo, hydroxy, amino, mono- or di$(C_1-C_6)$alkylamino, $(C_1-C_6)$alkyl, $(C_1-C_6)$alkylthio and $(C_1-C_6)$alkoxy. The subscript n is an integer of from 0 to 4.

G. Benzo[b]phenoxazines

Still other compounds useful in the present methods are provided in formulae VII and VII':

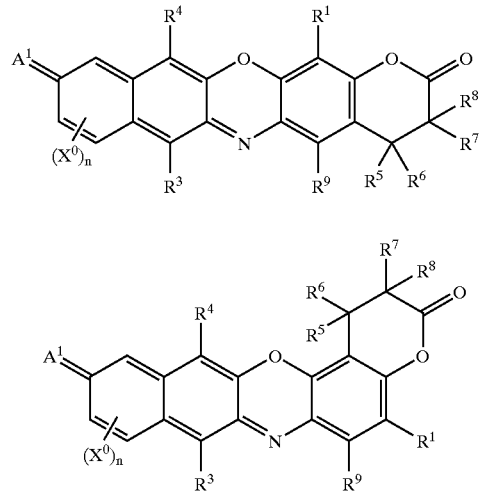

(VII)

and (VII')

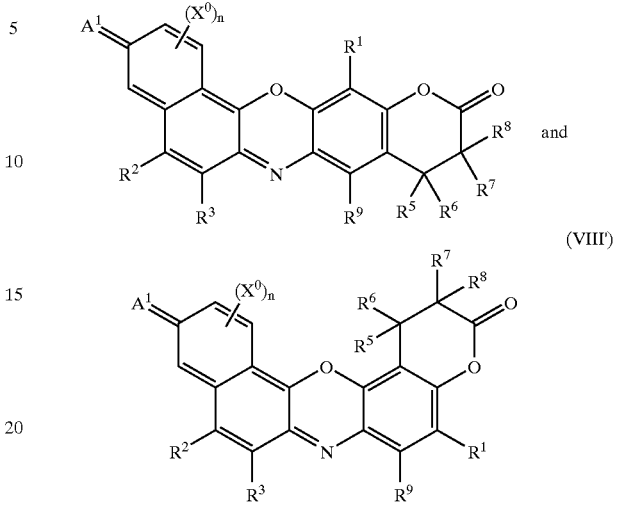

(VIII)

and (VIII')

wherein $A^1$ represents O or N—Z in which Z is H or $(C_1-C_8)$alkyl, or is combined with an adjacent $X^0$ group to form a 5- or 6-membered ring or can be combined with two adjacent $X^0$ groups to form two fused 6-membered rings; $R^1$, $R^3$, $R^4$ and $R^9$ are each independently selected from H, halogen, cyano, $CF_3$, $(C_1-C_8)$alkyl, $(C_1-C_8)$alkylthio, $(C_1-C_8)$alkoxy, aryl and heteroaryl; $R^5$, $R^6$, $R^7$ and $R^8$ are each independently selected from the group consisting of H, $(C_1-C_8)$alkyl, aryl, heteroaryl, aryl$(C_1-C_4)$alkyl and heteroaryl$(C_1-C_4)$alkyl; wherein the alkyl portions of any of $R^1$ or $R^3$ through $R^9$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and the aryl or heteroaryl portions of any of $R^1$ and $R^3$ through $R^9$ are optionally substituted with from one to four substituents selected from the group consisting of halogen, cyano, carboxy, sulfo, hydroxy, amino, mono- or di$(C_1-C_6)$alkylamino, $(C_1-C_6)$alkyl, $(C_1-C_6)$alkylthio and $(C_1-C_6)$alkoxy; each $X^0$ is independently selected from the group consisting of H, halogen, cyano, $CF_3$, $(C_1-C_8)$alkyl, $(C_1-C_8)$alkoxy, $(C_1-C_8)$alkylthio, $(C_1-C_8)$alkenyl, $(C_1-C_8)$alkynyl, aryl, heteroaryl, $SO_3H$ and $CO_2H$. Additionally, the alkyl or aryl portions of any $X^0$ can be further substituted with halogen, carboxy, sulfo, amino, mono- or dialkylamino, alkoxy, cyano, haloacetyl or hydroxy, and the alkyl portions of the substituents have from 1 to 6 carbon atoms. Optionally, any two adjacent $X^0$ groups can be taken together to form a fused aromatic or heteroaromatic ring that is optionally further substituted with from one to four substituents selected from halogen cyano, carboxy, sulfo, hydroxy, amino, mono- or di$(C_1-C_6)$alkylamino, $(C_1-C_6)$alkyl, $(C_1-C_6)$alkylthio and $(C_1-C_6)$alkoxy. The subscript n is an integer of from 0 to 3.

H. Benzo[c]phenoxazines

Still other compounds useful in the present methods are provided in formulae VIII and VIII':

wherein $A^1$ represents O or N—Z in which Z is H or $(C_1-C_8)$alkyl, or is combined with an adjacent $X^0$ group to form a 5- or 6-membered ring or can be combined with two adjacent $X^0$ groups to form two fused 6-membered rings; $R^1$, $R^2$, $R^3$ and $R^9$ are each independently selected from H, halogen, cyano, $CF_3$, $(C_1-C_8)$alkyl, $(C_1-C_8)$alkylthio, $(C_1-C_8)$alkoxy, aryl and heteroaryl; $R^5$, $R^6$, $R^7$ and $R^8$ are each independently selected from the group consisting of H, $(C_1-C_8)$alkyl, aryl, heteroaryl, aryl$(C_1-C_4)$alkyl and heteroaryl$(C_1-C_4)$alkyl; wherein the alkyl portions of any of $R^1$, $R^2$, $R^3$ or $R^5$ through $R^9$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and the aryl or heteroaryl portions of any of $R^1$, $R^2$, R or $R^5$ through $R^9$ are optionally substituted with from one to four substituents selected from the group consisting of halogen, cyano, carboxy, sulfo, hydroxy, amino, mono- or di$(C_1-C_6)$alkylamino, $(C_1-C_6)$alkyl, $(C_1-C_6)$alkylthio and $(C_1-C_6)$alkoxy; each $X^0$ is independently selected from the group consisting of H, halogen, cyano, $CF_3$, $(C_1-C_8)$alkyl, $(C_1-C_8)$alkoxy, $(C_1-C_8)$alkylthio, $(C_1-C_8)$alkenyl, $(C_1-C_8)$alkynyl, aryl, heteroaryl, $SO_3H$ and $CO_2H$. Additionally, the alkyl or aryl portions of any $X^0$ can be further substituted with halogen, carboxy, sulfo, amino, mono- or dialkylamino, alkoxy, cyano, haloacetyl or hydroxy, and the alkyl portions of the substituents have from 1 to 6 carbon atoms. Optionally, any two adjacent $X^0$ groups can be taken together to form a fused aromatic or heteroaromatic ring that is optionally further substituted with from one to four substituents selected from halogen cyano, carboxy, sulfo, hydroxy, amino, mono- or di$(C_1-C_6)$alkylamino, $(C_1-C_6)$alkyl, $(C_1-C_6)$alkylthio and $(C_1-C_6)$alkoxy. The subscript n is an integer of from 0 to 3.

I. Coumarins and Benzocoumarins

The methods of the present invention can be carried out using coumarin or benzocoumarin fused-lactone dyes.

Coumarin fused-lactone dyes useful in the invention, have the formula:

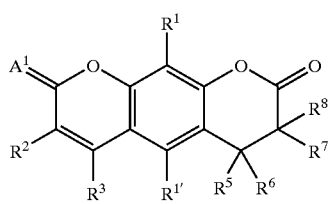

(IX)

wherein $R^1$, $R^{1'}$, $R^2$ and $R^3$ are each independently selected from the group consisting of H, halogen, cyano, $CF_3$, $(C_1-C_8)$alkyl, $(C_1-C_8)$alkylthio, $(C_1-C_8)$alkoxy, aryl and heteroaryl; $R^5$, $R^6$, $R^7$ and $R^8$ are each independently selected from the group consisting of H, $(C_1-C_8)$alkyl, aryl, heteroaryl, aryl$(C_1-C_4)$alkyl and heteroaryl$(C_1-C_4)$alkyl; wherein the alkyl portions of any of $R^{1'}$ or $R^1$ through $R^8$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and the aryl or heteroaryl portions of any of $R^{1'}$ and $R^1$ through $R^8$ are optionally substituted with from one to four substituents selected from the group consisting of halogen, cyano, carboxy, sulfo, hydroxy, amino, mono- or di$(C_1-C_6)$alkylamino, $(C_1-C_6)$alkyl, $(C_1-C_6)$alkylthio and $(C_1-C_6)$alkoxy. In certain embodiments, $R^2$ and $R^3$ are taken together to form a fused aromatic ring. The symbol $A^1$ represents O or N—Z, in which Z is H or $(C_1-C_8)$alkyl.

In certain embodiments, $R^2$ and $R^3$ are independently selected from halogen, cyano, $CF_3$, $(C_1-C_8)$alkyl, and aryl or heteroaryl having the formula:

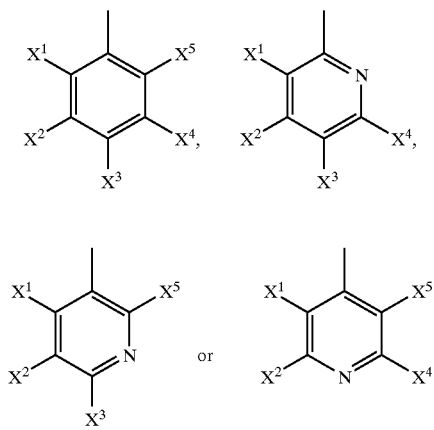

wherein $X^1$, $X^2$, $X^3$, $X^4$ and $X^5$ are each independently selected from the group consisting of H, halogen, cyano, $CF_3$, $(C_1-C_8)$alkyl, $(C_1-C_8)$alkoxy, $(C_1-C_8)$alkylthio, $(C_1-C_8)$alkenyl, $(C_1-C_8)$alkynyl, $SO_3H$ and $CO_2H$. Additionally, the alkyl portions of any of $X^1$ through $X^5$ can be further substituted with halogen, carboxy, sulfo, amino, mono- or dialkylamino, alkoxy, cyano, haloacetyl or hydroxy, and the alkyl portions of the substituents have from 1 to 6 carbon atoms. Optionally, any two adjacent substituents $X^1$ through $X^5$ can be taken together to form a fused aromatic ring that is optionally further substituted with from one to four substituents selected from halogen cyano, carboxy, sulfo, hydroxy, amino, mono- or di$(C_1-C_6)$alkylamino, $(C_1-C_6)$alkyl, $(C_1-C_6)$alkylthio and $(C_1-C_6)$alkoxy.

The benzocoumarin series of dyes are those of formula IX in which $R^2$ and $R^3$ are combined to form a fused benzene ring, optionally substituted with one to four substituents selected from halogen cyano, carboxy, sulfo, hydroxy, amino, mono- or di$(C_1-C_6)$alkylamino, $(C_1-C_6)$alkyl, $(C_1-C_6)$alkylthio and $(C_1-C_6)$alkoxy.

Certain coumarin fused-lactone dyes can be prepared as outlined in Reaction Scheme 4.

Reaction Scheme 4

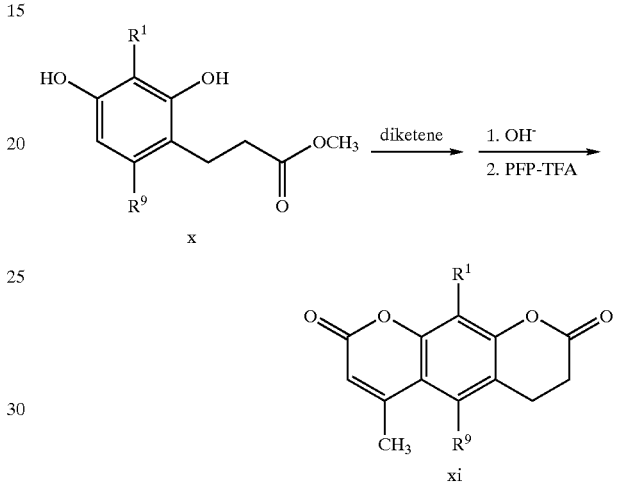

General Synthesis of Lactone Dyes

Many of the fused-lactone dyes can be prepared from common intermediate that are readily available to one of skill in the art. Two groups of particularly useful intermediates are the 2-substituted 1,3-dihydroxyphenylpropionates and the isomeric, 4-substituted 2,6-dihydroxyphenylpropionates. These compounds can be prepared as outlined below.

2-Substituted 1,3-dihydroxyphenylpropionates 5a–c were synthesized in 4 steps (Reaction Scheme 5A) in good total yields starting from either 2-chloro-1,3-dimethoxybenzene (1a) (Kovacic, P.; Kurz, M. E. *J. Org. Chem.* 1966, 31, 2459–2467; Wada, M.; Wakamori, H.; Hirawa, A.; Erabi, T. *Bull. Chem. Soc. Jpn.*, 1992, 65 (5), 1389–1391) or 2-fluoro-1,3-dimethoxybenzene (1b) (W. -C. Sun et al. *J. Org. Chem.* 1997, 62, 6469–6475) or 2-phenyl-1,3-dimethoxybenzene (1c) (U.S. Pat. No. 6,221,604). Formylation with α,α-dichloromethyl methyl ether in the presence of $TiCl_4$ afforded aldehydes 2 in high yields (95%). These compounds were quantitatively converted into the cinnamic acids 3 by reaction with malonic acid in the presence of catalytic amount of piperidine. Catalytic hydrogenation (10% Pd/C, 40 psi) gave acids 4 in greater than 95% yields. Deprotection of the methoxy groups using acetic acid/aqueous hydrobromic acid mixture followed by esterification of the carboxy group (methanol/HCl gas) afforded the desired 2-substituted methyl 1,3-dihydroxyphenylpropionates 5. Compound 5d was prepared by an alternative synthetic route in accordance with Blickenstaff, R. T., et al. (Tetrahedron, 24: 2495–2498 (1968)).

Reaction Scheme 5

A. Preparation of 2-substituted methyl 1,3-dihydroxyphenylpropionates

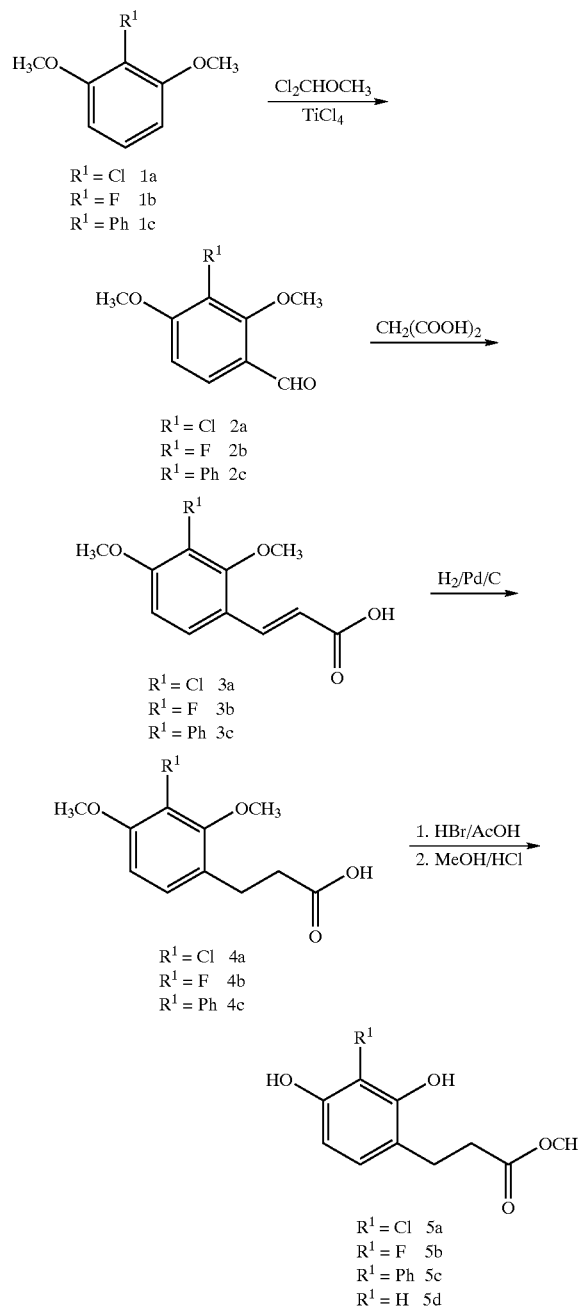

B. Preparation of 4-substituted methyl 2,6-dihydroxyphenylpropionates

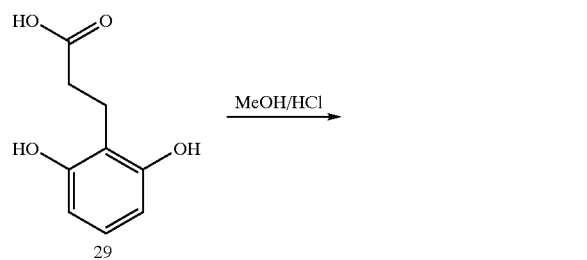

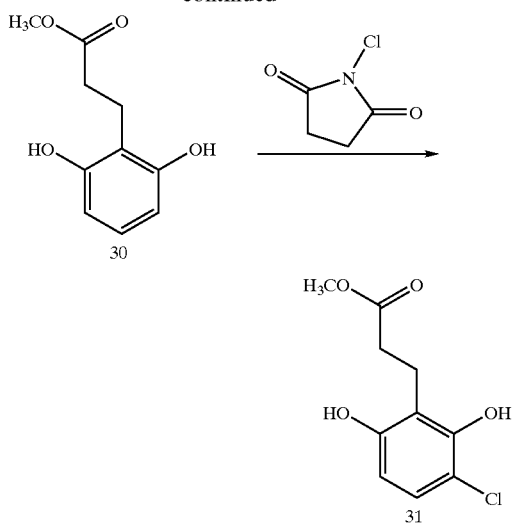

The isomeric methyl 2,6-dihydroxyphenylpropionates 30 and 31 were synthesized starting from 3-(2,6-dihydroxyphenyl)propionic acid (Mitoshi K. et al. *Syn. Lett.*, 12:1472–1474 (1997)) as shown above.

The dihydroxyphenylpropionates have been implemented into the synthesis of several classes of chromanone dye precursors. The synthetic approaches herein are based on utilizing the versatile substituted methyl dihydroxyphenylpropionates in conjunction with known synthetic routes for dye assembly. The application of the intermediates is not limited to the classes described below, but finds broad application to any resorcinol based dye chemistry. Moreover, the intermediates described above can be prepared using a variety of other art-recognized methods.

Coumarin Lactone Dye Synthesis

Resorcinol analogs 5 were reacted with diketene to afford 8-halocoumarins 6 in high yields. Hydrolysis of the ester group generated free acids 7 which were lactonized in the presence of pentafluorophenyl trifluoroacetate (PFP-TFA) to give chromanones 8. See Reaction Scheme 6.

Reaction Scheme 6

Synthesis of 8-substituted coumarin lactones

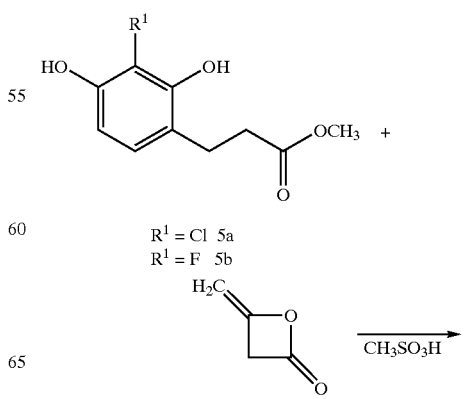

-continued

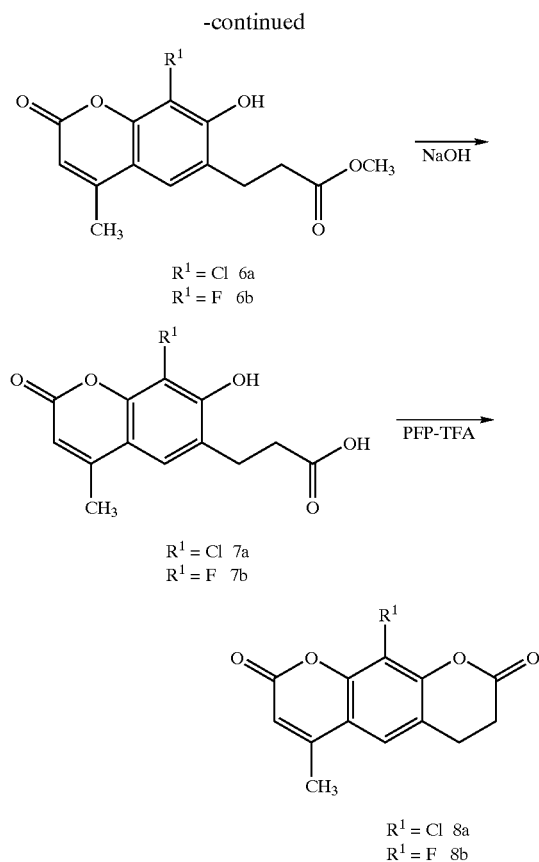

R¹ = Cl  6a
R¹ = F   6b

R¹ = Cl  7a
R¹ = F   7b

R¹ = Cl  8a
R¹ = F   8b

Phenoxazine Lactone Dye Synthesis

Phenoxazine lactone dyes can be prepared as generally outlined in Reaction Scheme 3 and more specifically provided in Reaction Scheme 7, below.

Reaction Scheme 7

Synthesis of substituted phenoxazine lactones

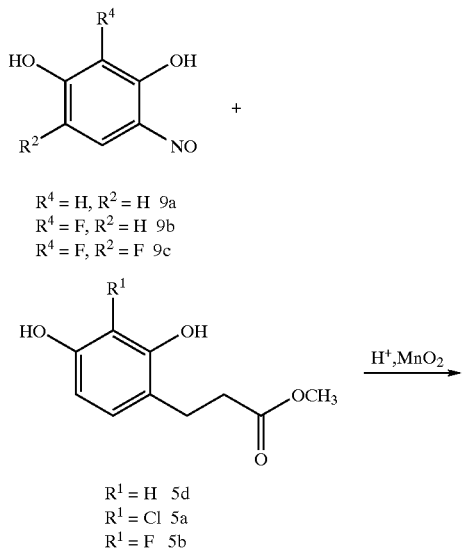

R⁴ = H, R² = H  9a
R⁴ = F, R² = H  9b
R⁴ = F, R² = F  9c

R¹ = H   5d
R¹ = Cl  5a
R¹ = F   5b

-continued

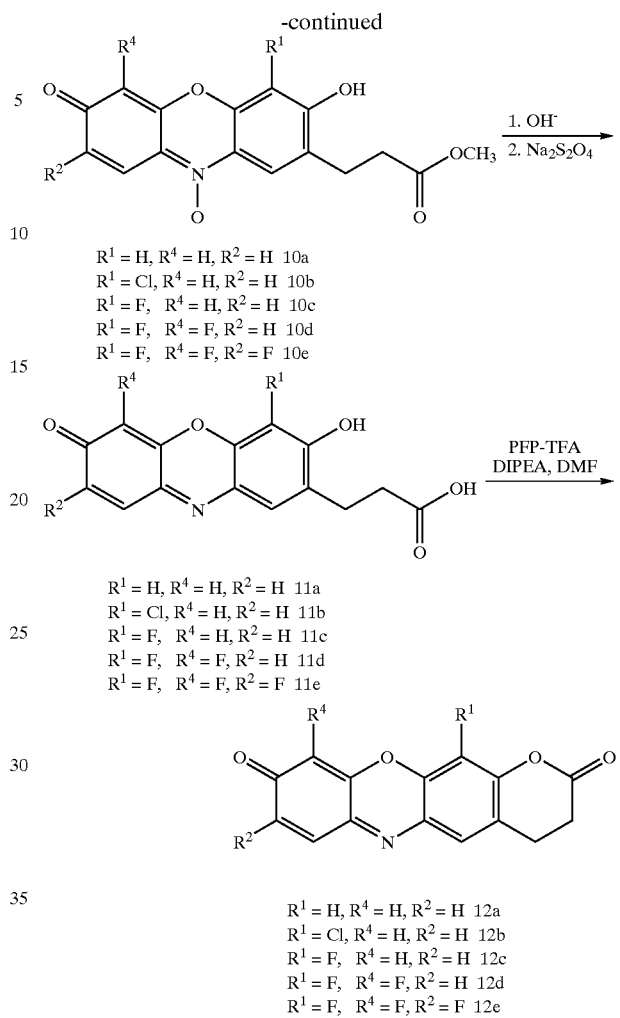

R¹ = H,  R⁴ = H, R² = H  10a
R¹ = Cl, R⁴ = H, R² = H  10b
R¹ = F,  R⁴ = H, R² = H  10c
R¹ = F,  R⁴ = F, R² = H  10d
R¹ = F,  R⁴ = F, R² = F  10e

R¹ = H,  R⁴ = H, R² = H  11a
R¹ = Cl, R⁴ = H, R² = H  11b
R¹ = F,  R⁴ = H, R² = H  11c
R¹ = F,  R⁴ = F, R² = H  11d
R¹ = F,  R⁴ = F, R² = F  11e

R¹ = H,  R⁴ = H, R² = H  12a
R¹ = Cl, R⁴ = H, R² = H  12b
R¹ = F,  R⁴ = H, R² = H  12c
R¹ = F,  R⁴ = F, R² = H  12d
R¹ = F,  R⁴ = F, R² = F  12e

Reaction of 4-nitrosorecorcinol derivatives 9 (commercially available or synthesized in accordance with the state-of-the-art) and 5 in the presence of $MnO_2$ and using methanol as a solvent gave crystalline precipitates of sufficiently pure N-oxides 10 in satisfactory yields (20–40%). The ester functions were hydrolyzed with NaOH followed by reduction of the N-oxide groups by a treatment with sodium diothionite to yield resorufin derivatives 11. Treatment of acids 11 with PFP/TFA catalyzed the formation of lactones 12.

Xanthene Dye Lactone Synthesis

Synthesis of asymmetrical xanthene dyes (Reaction Scheme 8a) was accomplished in two stages. At the first stage benzophenones 14 were prepared in good to excellent yields by Friedel-Crafts acylation of resorcinol analogs 5 with phthalic anhydrides 13 in the presence of $AlCl_3$. At the second stage ketones 14 were reacted with resorcinols 15 using either methanesulfonic or trifluoroacetic (plus catalytic methanesulfonic acid) acid as a solvent. Depending on the solvent either esters 16 or free acids 17 were obtained. The acid route was preferred for consequent conversion into lactones 18, the latest was achieved by treatment of acids 17 with PFP-TFA.

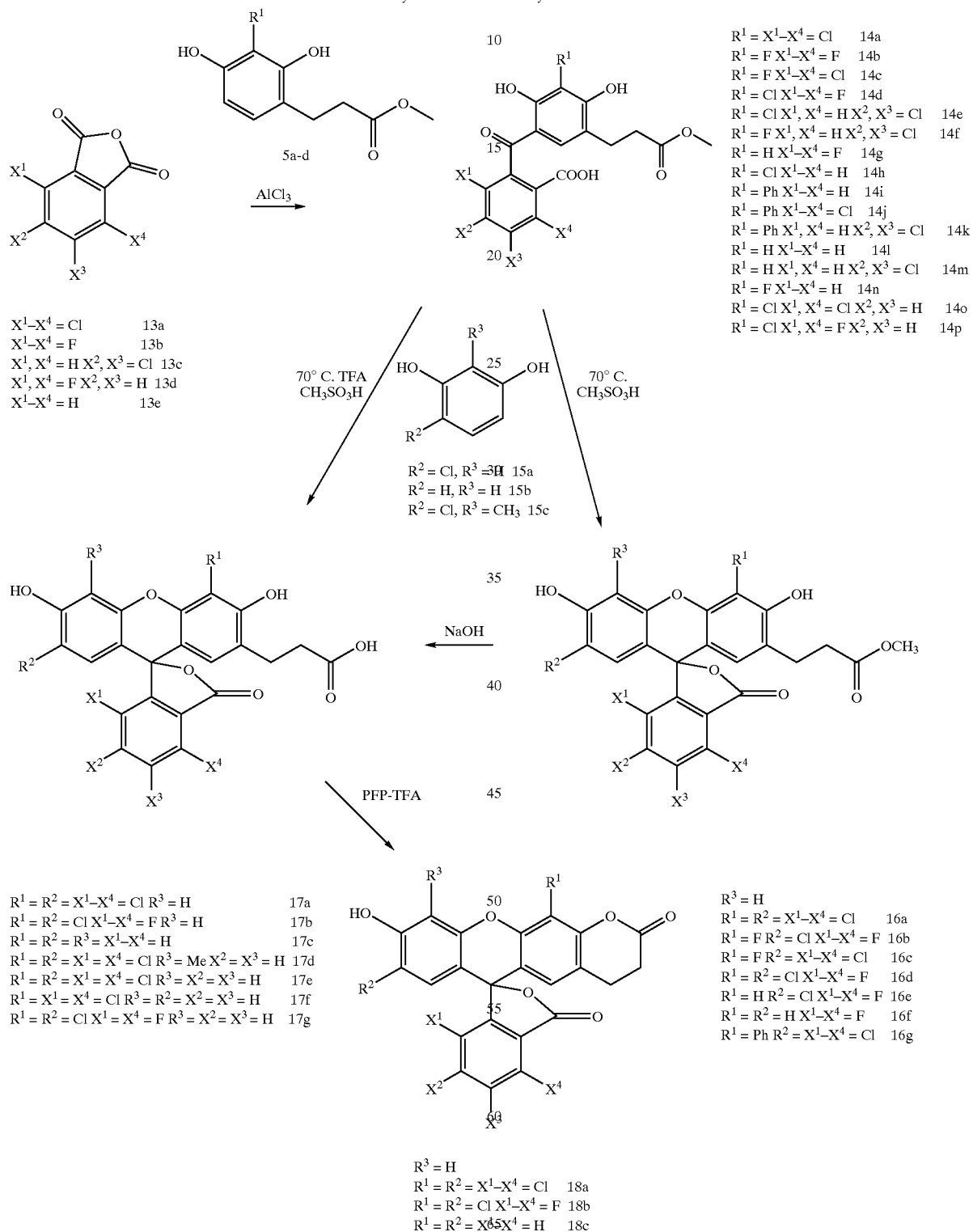

An alternative synthesis is provided in Scheme 8b for asymmetric 4,7-unsubstituted xanthenes (compounds of Scheme 8a, wherein $X^1$ and $X^4$ are H). While the two-step condensation method is illustrated for the 4,7-unsubstituted class of xanthene dyes, one of skill in the art will appreciate that the method is not so limited and can be applied to more efficient preparation of many xanthene dyes.

The synthesis of asymmetric 4,7-unsubstituted ($X^1$ and $X^4$=H Scheme 8a) using Scheme 8a provides compounds such as 17c ($X^1$—$X^4$=H) in about 20% yield and requires laborious chromatography purification. The related 5,6-dichlorosubstituted fluoresceins synthesized by the same method (Scheme 8a) gave only 20–60% of the desired product. Still other conventional synthetic procedures such as fusion with $ZnCl_2$, sulfuric acid or methanesulfonic acid produced similar unsatisfactory results. By-products of the reaction were determined to be symmetric fluoresceins of structures 33 and 34 (Scheme 8b). Without intending to be bound by theory, these compounds appear to be formed due to the reversibility of the triphenylmethane intermediate at elevated temperatures. It should be noted that that same side products but in smaller amounts (5–10%) were also observed during the preparation of 4,7-chloro- or fluorosubstituted fluoresceines (17a–17f).

An alternative, and preferred, synthetic procedure was used for the synthesis of 4,7-unsubstituted asymmetric xanthene dyes (Scheme 8b). The reaction between benzophenone 14 and resorcinol 15 was first carried out at low temperatures (0–20° C.) in the presence of methanesulfonic acid as a catalyst and trifluoroacetic acid as a solvent. Under these conditions only the desired triphenylmethane intermediate is formed which can be isolated as a colorless spirolactone 32 (Scheme 8b). The following cyclization step was performed under neutral or mild basic conditions in aqueous solutions at 20–60° C. Finally, the acids 17 were precipitated by acidification. This approach allowed the preparation of 4,7-unsubstituted asymmetric fluoresceins in excellent yields.

The new method provides a universal way of synthesizing asymmetric xanthene dyes under very mild conditions (e.g., at temperatures of from about 0–20° C.) and therefore, is useful for the introduction of more labile functional groups. The method is particularly useful for the preparation of asymmetric 4,7-unsubstituted xanthenes which are practically inaccessible by conventional approaches.

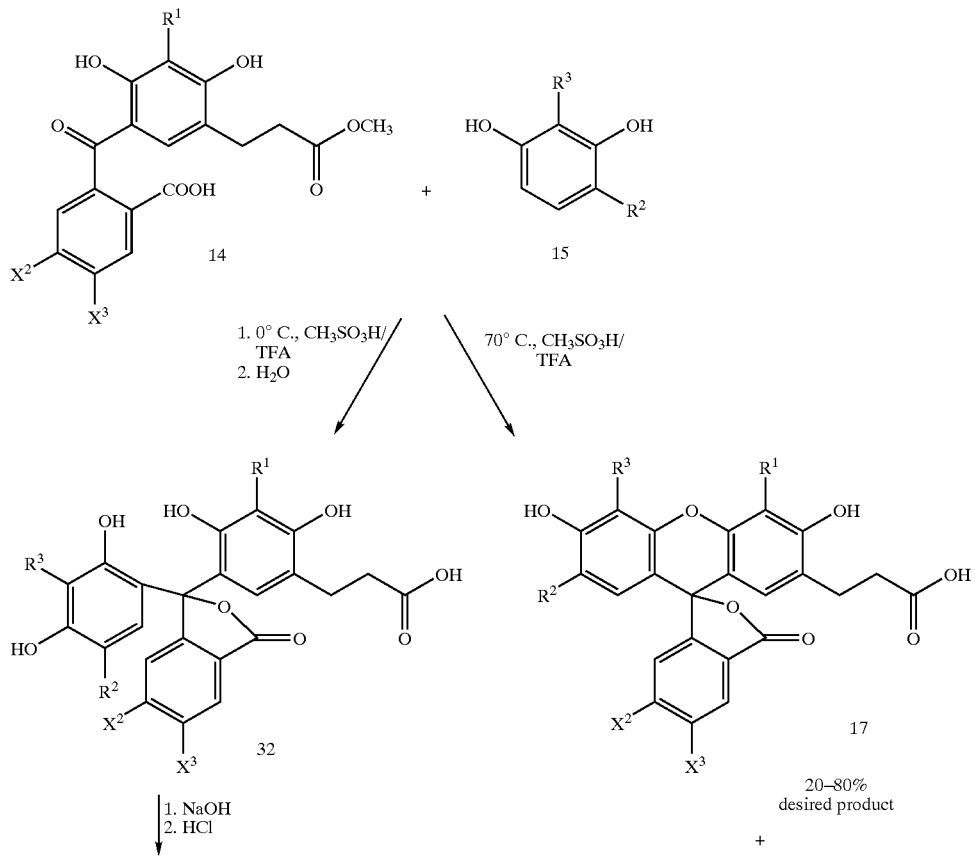

Reaction Scheme 8b

Synthesis of asymmetric 4,7-unsubstituted fluoresceins using the two-step condensation method.

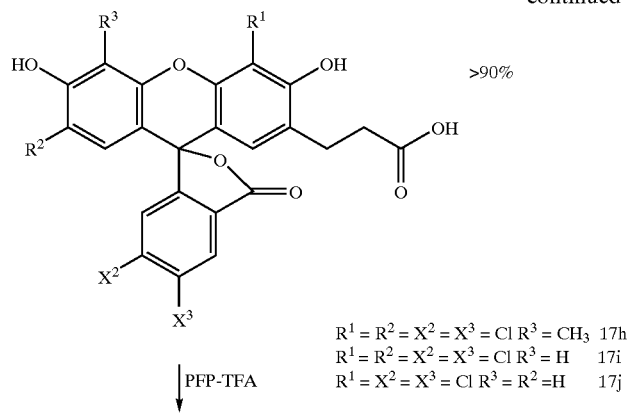

R¹ = R² = X² = X³ = Cl R³ = CH₃  17h
R¹ = R² = X² = X³ = Cl R³ = H     17i
R¹ = X² = X³ = Cl R³ = R² = H     17j

↓ PFP-TFA

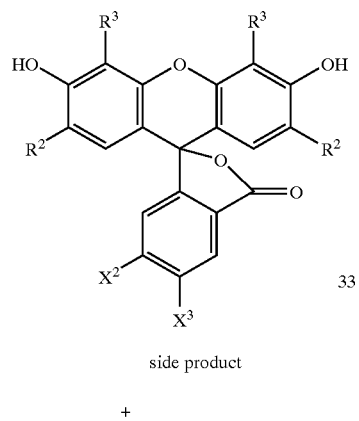

33
side product

+

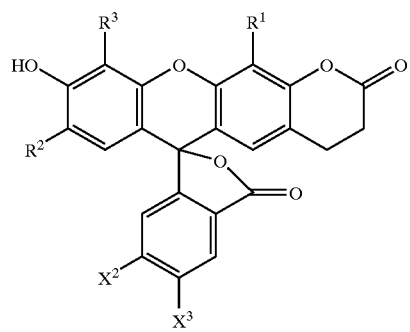

R¹ = R² = X² = X³ = Cl R³ = CH₃  18d

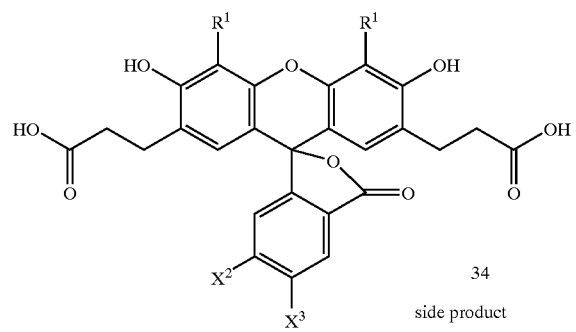

34
side product

Compounds 16 and 17 synthesized according to the process shown in Reaction Scheme 8a and 8b are listed in Table 1 with absorbance maximum (Abs), emission maximum (Em) and Stokes shift (St) in nm.

TABLE 1

| No | R¹ | R² | R³ | X¹ and X⁴ | X² and X³ | Abs (nm) | Em (nm) | St (nm) |
|---|---|---|---|---|---|---|---|---|
| 16c | F | Cl | H | Cl | Cl | 530 | 546 | 16 |
| 16b | F | Cl | H | F | F | 528 | 546 | 18 |
| 16a | Cl | Cl | H | Cl | Cl | 527 | 544 | 17 |
| 16d | Cl | Cl | H | F | F | 527 | 543 | 16 |
| 16e | H | Cl | H | F | F | 518 | 534 | 16 |
| 16f | H | H | H | F | F | 512 | 530 | 18 |
| 17d | Cl | Cl | CH₃ | Cl | H | 531 | 549 | 18 |
| 17e | Cl | Cl | H | Cl | H | 524 | 540 | 16 |
| 17f | Cl | H | H | Cl | H | 519 | 534 | 15 |

TABLE 1-continued

| No | R¹ | R² | R³ | X¹ and X⁴ | X² and X³ | Abs (nm) | Em (nm) | St (nm) |
|---|---|---|---|---|---|---|---|---|
| 17g | Cl | Cl | H | F | H | 522 | 539 | 17 |
| 17h | Cl | Cl | CH₃ | H | Cl | 520 | 543 | 23 |
| 17i | Cl | Cl | H | H | Cl | 514 | 535 | 21 |
| 17j | Cl | H | H | H | Cl | 508 | 530 | 22 |

Fluorescence and absorbance spectra were recorded in 0.1 M phosphate buffer pH 7.5

Reaction Scheme 8c illustrates the preparation of an isomeric xanthene dye (a lactone dye of formula Ib, above.

Reaction Scheme 8c

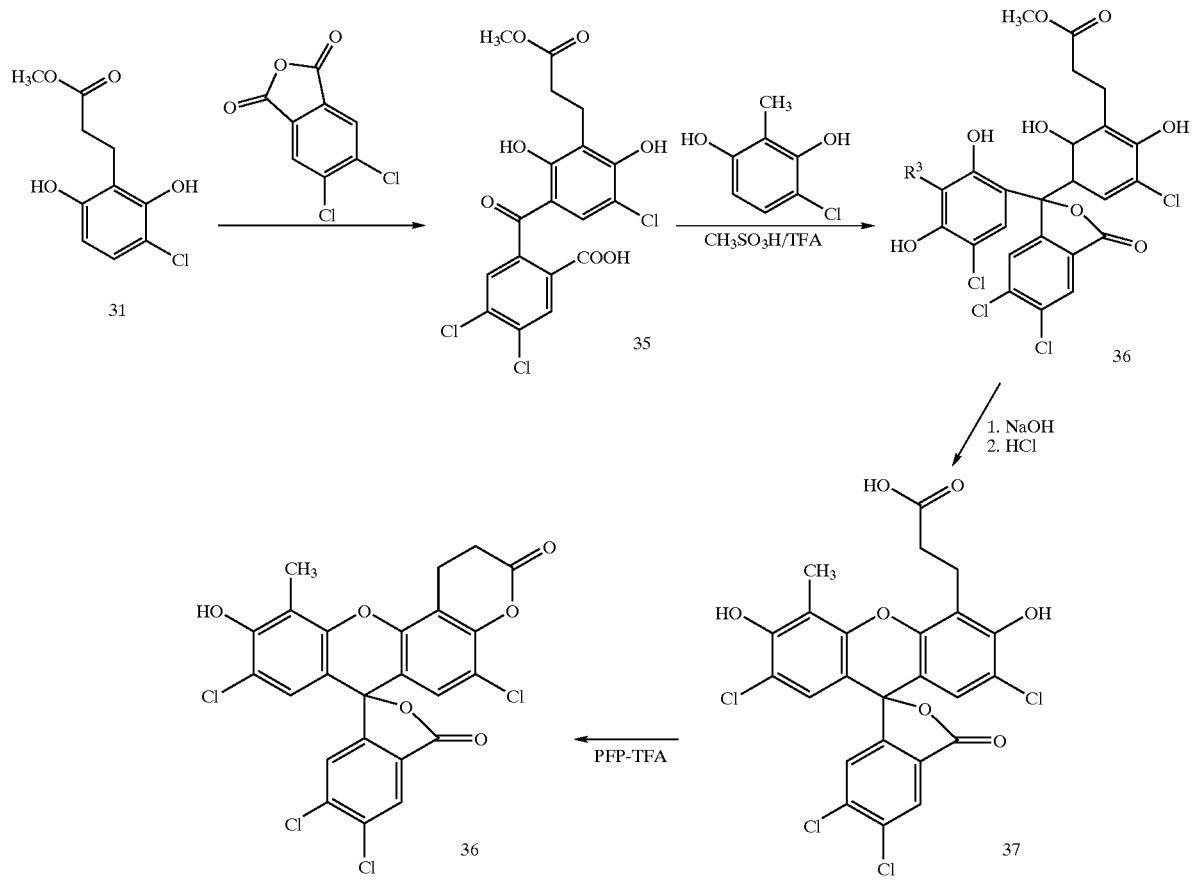

Benzo[a]- and Benzo[c]xanthene Dye Lactone Synthesis

Benzo[a]- and benzo[c]xanthene dyes 19 (Reaction Scheme 9) and 23 (Reaction Scheme 10) were synthesized analogously to xanthene dyes (Reaction Scheme 8) using condensation of benzophenones 14 either with 1,3- or 1,6-dihydroxynaphthalene. Two of the esters 19 were hydrolyzed to acids 20 and then converted into lactones 21. Spectral properties of esters 19 summarized in Table 2.

Reaction Scheme 9

Synthesis of benzo[a]xanthene dye lactones

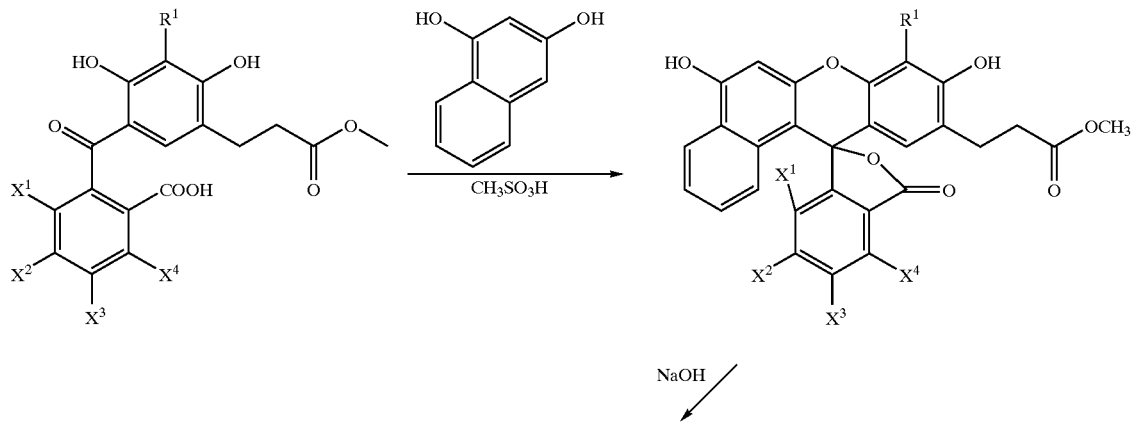

-continued

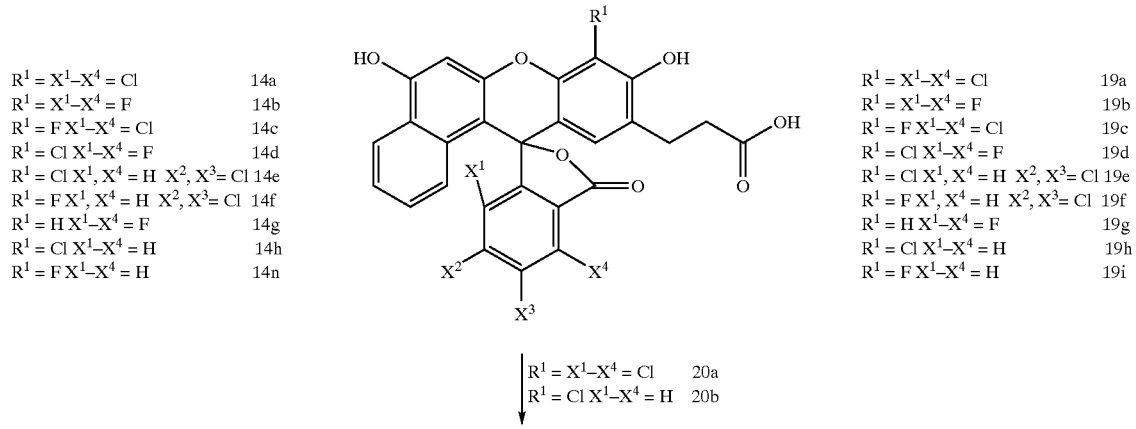

| | 14a |
|---|---|
| $R^1 = X^1-X^4 = Cl$ | 14a |
| $R^1 = X^1-X^4 = F$ | 14b |
| $R^1 = F X^1-X^4 = Cl$ | 14c |
| $R^1 = Cl X^1-X^4 = F$ | 14d |
| $R^1 = Cl X^1, X^4 = H \ X^2, X^3 = Cl$ | 14e |
| $R^1 = F X^1, X^4 = H \ X^2, X^3 = Cl$ | 14f |
| $R^1 = H X^1-X^4 = F$ | 14g |
| $R^1 = Cl X^1-X^4 = H$ | 14h |
| $R^1 = F X^1-X^4 = H$ | 14n |

| | |
|---|---|
| $R^1 = X^1-X^4 = Cl$ | 19a |
| $R^1 = X^1-X^4 = F$ | 19b |
| $R^1 = F X^1-X^4 = Cl$ | 19c |
| $R^1 = Cl X^1-X^4 = F$ | 19d |
| $R^1 = Cl X^1, X^4 = H \ X^2, X^3 = Cl$ | 19e |
| $R^1 = F X^1, X^4 = H \ X^2, X^3 = Cl$ | 19f |
| $R^1 = H X^1-X^4 = F$ | 19g |
| $R^1 = Cl X^1-X^4 = H$ | 19h |
| $R^1 = F X^1-X^4 = H$ | 19i |

$R^1 = X^1-X^4 = Cl$    20a
$R^1 = Cl X^1-X^4 = H$    20b

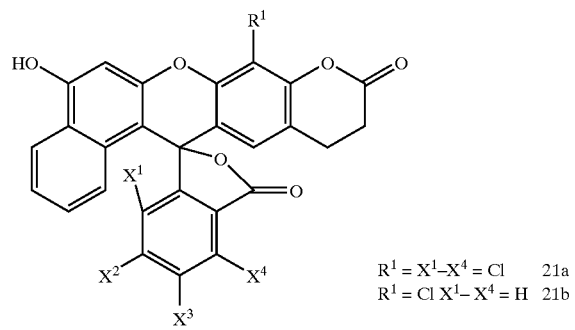

$R^1 = X^1-X^4 = Cl$    21a
$R^1 = Cl X^1-X^4 = H$    21b

Particular compounds prepared according to this Scheme are provided in Table 2 along with absorption, emission and Stokes shift wavelengths.

TABLE 2

Physical Characteristics of Compounds Synthesized by Reaction Scheme 9

| No | $R^1$ | $R^4$ | $X^1$ and $X^4$ | $X^2$ and $X^3$ | Abs (nm) | Em (nm) | St (nm) |
|---|---|---|---|---|---|---|---|
| 19b | F | H | F | F | 535 | 570 | 35 |
| 19c | F | H | Cl | Cl | 537 | 571 | 34 |
| 19d | Cl | H | F | F | 535 | 567 | 32 |
| 19a | Cl | H | Cl | Cl | 538 | 565 | 27 |
| 19f | F | H | H | Cl | 522 | 562 | 40 |
| 19g | H | H | F | F | 529 | 560 | 31 |
| 19e | Cl | H | H | Cl | 522 | 557 | 35 |
| 19h | Cl | H | H | H | 516 | 546 | 30 |
| 19i | F | H | H | H | 517 | 551 | 34 |

Reaction Scheme 10

Example of a benzo[c]xanthene dye lactone synthesis

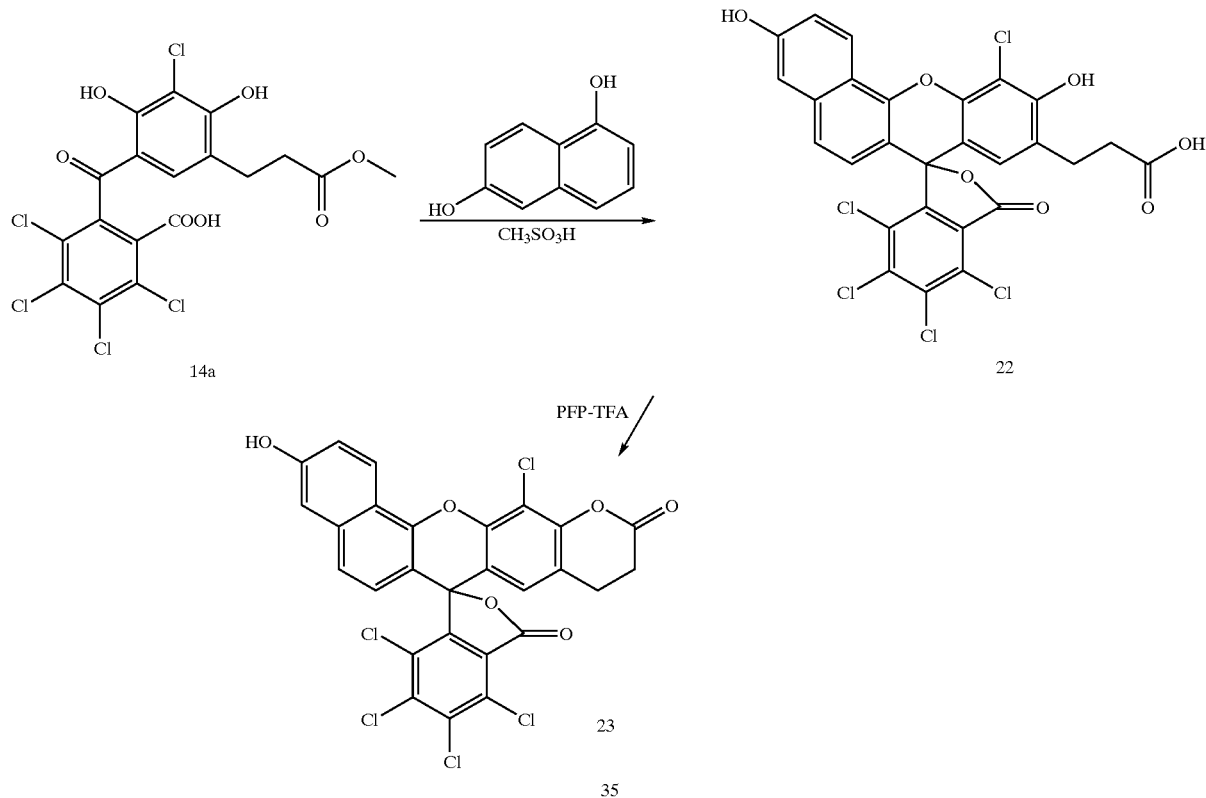

Derivation of Amino-Tailed Oligonucleotides Using Lactone Dyes.

In order to evaluate the utility of chromanone dye precursors as amine derivatizing agents post-synthetic modification of aminohexyl-tailed oligonucleotides (ODNs) was tested. Four classes of the chromanones, which varied in both chromaphore structure and acidity of leaving phenolic hydroxy group, were used. The reactions between the reagents and triethylammonium salts of aminohexyl-modified ODNs were done in organic (DMSO) solvent. Small (2–5×) molar excesses of the reactive dyes led to essentially quantitative (90+%) labeling of the amine-containing ligand. The conjugates were purified by gel-electrophoresis and reverse-phase HPLC. Analysis of absorbance and fluorescence spectra (Table 3) of the conjugates demonstrated successful dye incorporation into the amine-containing ligand and expected spectral characteristics.

Reaction Scheme 11

Derivatization of aminohexyl-octathymidylate with various dyes using lactone dyes

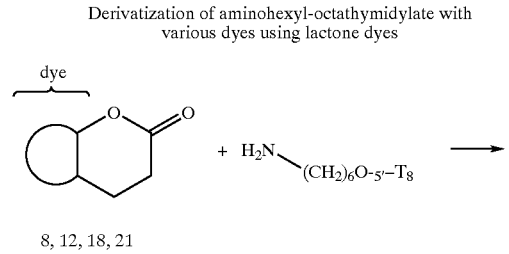

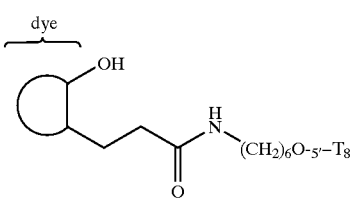

8, 12, 18, 21-T$_8$

TABLE 3

Absorbance and fluorescence properties of dye-modified octathymidylates.

| | Absorbance max (nm) | Extinction coefficient* | Emission max (nm) | Signal Strength** | Stokes shift (nm) |
|---|---|---|---|---|---|
| 8a-T$_8$ | 375 | 20000 | 451 | 0.13 | 76 |
| 8b-T$_8$ | 371 | 20000 | 461 | 0.12 | 90 |
| 18c-T$_8$ | 495 | 85000 | 518 | 1.0 | 23 |
| 18a-T$_8$ | 532 | 100000 | 548 | 0.6 | 16 |
| 18b-T$_8$ | 530 | 100000 | 546 | 0.6 | 16 |
| 21b-T$_8$ | 520 | 65000 | 552 | 0.3 | 32 |
| 21a-T$_8$ | 542 | 65000 | 570 | 0.25 | 28 |
| 12a-T$_8$ | 581 | 70000 | 594 | 0.125 | 13 |
| 12b-T$_8$ | 591 | 70000 | 604 | 0.06 | 13 |
| 12c-T$_8$ | 592 | 70000 | 603 | 0.06 | 11 |

TABLE 3-continued

Absorbance and fluorescence properties of dye-modified octathymidylates.

| | Absorbance max (nm) | Extinction coefficient* | Emission max (nm) | Signal Strength** | Stokes shift (nm) |
|---|---|---|---|---|---|
| 12d-T$_8$ | 601 | 65000 | 616 | 0.03 | 15 |
| 12e-T$_8$ | 601 | 60000 | 616 | 0.015 | 15 |

*The extinction coefficients were estimated by subtracting absorbance spectra of free dyes from the spectra of corresponding dye-labeled octathymidylates. The estimate assumes that absorbance at 260 nm is a sum of T$_8$ (molar extinction coefficient at 260 nm = 65000) and dye absorbances.
**Signal strength was determined as a relative molar fluorescence measured at the emission maximum (slit 2.5 nm) with excitation at the corresponding absorbance maximum (slit 2.5 nm). Fluorescence spectra were recorded on LS-50B (Perkin-Elmer) luminescence spectrophotometer in 0.15 M borate buffer pH 8.5.

In view of the broadly applicable synthetic methodology provided above, the present invention further provides a fused-lactone dye having the formula:

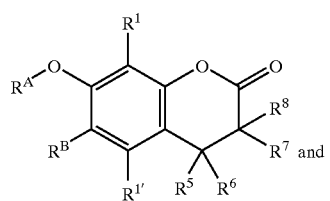

(X)

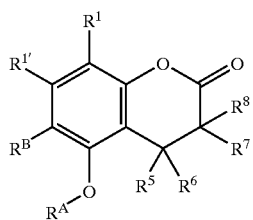

(X')

In the above formulae, $R^1$ and $R^{1'}$ are each members independently selected from the group consisting of H, halogen, cyano, $CF_3$, $(C_1-C_8)$alkyl, $(C_1-C_8)$alkylthio, $(C_1-C_8)$alkoxy, aryl and heteroaryl; $R^5$, $R^6$, $R^7$ and $R^8$ are each independently selected from the group consisting of H, $(C_1-C_8)$alkyl, aryl, heteroaryl, aryl$(C_1-C_4)$alkyl and heteroaryl$(C_1-C_4)$alkyl; wherein the alkyl portions of any of $R^1$, $R^{1'}$, or $R^5$ through $R^8$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and the aryl or heteroaryl portions of any of $R^1$, $R^{1'}$, and $R^5$ through $R^8$ are optionally substituted with from one to four substituents selected from the group consisting of halogen, cyano, carboxy, sulfo, hydroxy, amino, mono- or di$(C_1-C_6)$alkylamino, $(C_1-C_6)$alkyl, $(C_1-C_6)$alkylthio and $(C_1-C_6)$alkoxy. Additionally, the symbols $R^A$ and $R^B$ are combined to form a substituted or unsubstituted fused ring system having from 1 to 4 five- or six-membered rings; with the proviso that the compound has an emission wavelength of from 400 nm to 1200 nm, more preferably, 400 nm to about 850 nm.

Preferred groups of fused-lactone dyes are those provided in any of formula I, II, III, IV, V, VI, VII, VIII, IX or X, as well as the preferred fused-lactone dyes of formula Ia, Ib, IIa, IIb, IIIa, IIIb, IVa and IVb. Particularly preferred fused-lactone dyes are the preferred dyes listing in each of these formulae. Still further preferred are those fused-lactone dyes prepared and described in detail herein in any of Reaction Schemes 1 through 10.

Dye Reagents

The fused-lactone dyes provided above can be used to directly label biological materials or can be used to prepare a number of dye reagents that are useful in the methods described herein, as well as other labeling processes.

The scheme below illustrates both the opening of a "dye lactone" (abbreviated as a benzene fused lactone) with an amino ligand, and with a prolinol based linking group that is further elaborated to prepare phosphoramidite reagents or solid support bound reagents.

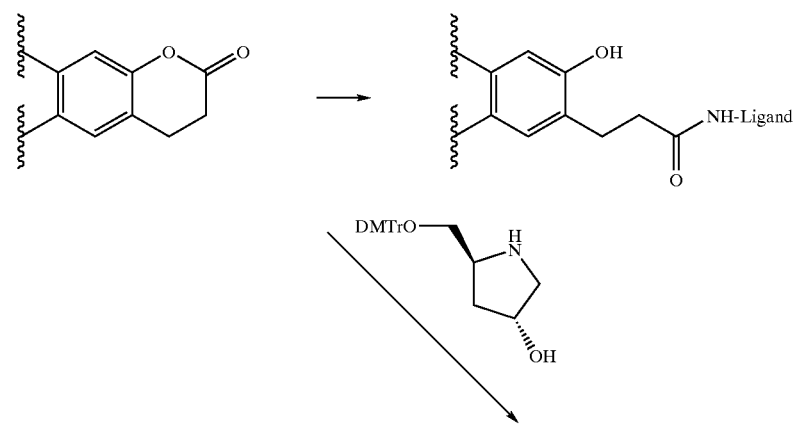

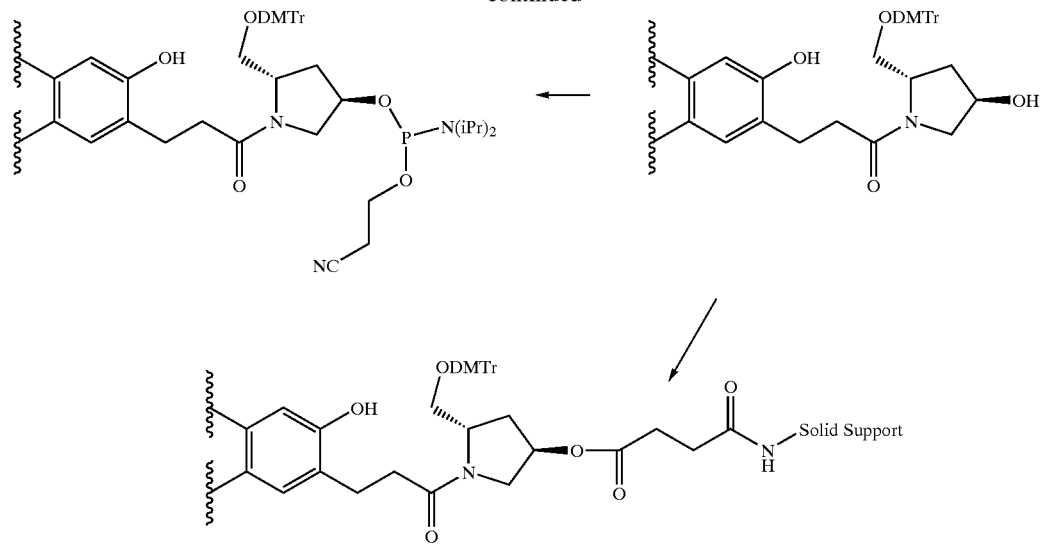

In view of the above, the present invention further provides a method for preparing a fluorescent dye-labeled phosphoramidite reagent, said method comprising:

(a) contacting a fluorescent dye-fused lactone derivative with a linking group component to form an intermediate fluorescent dye-labeled linking group; and (b) contacting said intermediate fluorescent dye-labeled linking group with a phosphoramidite moiety under conditions sufficient to covalently attach the phosphoramidite moiety to said fluorescent dye-labeled linking group and form said fluorescent dye-labeled phosphoramidite reagent. In preferred embodiments, the fluorescent dye-fused lactone derivative has a formula selected from the group consisting of I, II, III, IV, V, VI, VII, VIII, and IX. More preferably, the fluorescent dye-fused lactone derivative has a formula selected from the group consisting of Ia, Ib, IIa, IIb, IIIa, IIIb, IVa, IVb, V and VI. In other preferred embodiments, the linking group component comprises two reactive functional groups selected from amino, hydroxy, hydrazino and thiol, and is either linear or cyclic, or a combination of linear and cyclic. Still further preferred are those embodiments in which the linking group comprises a $(C_2-C_{20})$alkylene or $(C_2-C_{20})$heteroalkylene group. In related and preferred embodiments, the linking group is cyclic and comprises a five-membered heterocycle, more preferably the linking group is a prolinol linker.

In view of the facility with which these phosphoramidite reagents can be prepared, and the further application of this type of methodology to preparing solid support bound dye reagents, the present invention provides, in another aspect, dye reagents represented by a formula selected from:

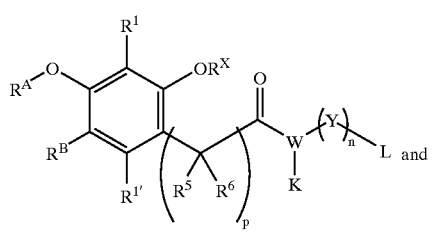 and

-continued

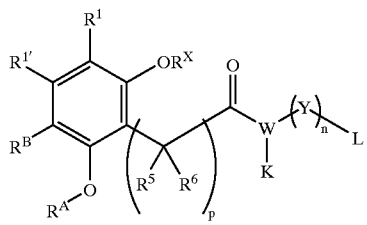 (XI')

In the above formulae, $R^1$ and $R^{1'}$ are each members independently selected from the group consisting of H, halogen, cyano, $CF_3$, $(C_1-C_8)$alkyl, $(C_1-C_8)$alkylthio, $(C_1-C_8)$alkoxy, aryl and heteroaryl; each $R^5$ and $R^6$ is independently selected from the group consisting of H, $(C_1-C_8)$alkyl, aryl, heteroaryl, aryl$(C_1-C_4)$alkyl and heteroaryl$(C_1-C_4)$alkyl; wherein the alkyl portions of any of $R^1$, $R^{1'}$, $R^5$ and $R^6$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and the aryl or heteroaryl portions of any of $R^1$, $R^{1'}$, $R^5$ and $R^6$ are optionally substituted with from one to four substituents selected from the group consisting of halogen, cyano, carboxy, sulfo, hydroxy, amino, mono- or di$(C_1-C_6)$alkylamino, $(C_1-C_6)$alkyl, $(C_1-C_6)$alkylthio and $(C_1-C_6)$alkoxy. Additionally, the symbols $R^A$ and $R^B$ are combined to form a substituted or unsubstituted fused ring system having from 1 to 4 five- or six-membered rings, optionally substituted with from 1 to 6 substituents selected from halogen, cyano, carboxy, sulfo, hydroxy, amino, mono- or di$(C_1-C_6)$alkylamino, $(C_1-C_6)$alkyl, $(C_1-C_6)$alkylthio and $(C_1-C_6)$alkoxy; $R^x$ is selected from the group consisting of H and hydroxy protecting groups; the subscript p is an integer of from 1 to 3; W, or W and K taken together is a linking group which can be a bifunctional linker, trifunctional linker or polyfunctional linker (see, for example, di- and tri-functional linkers described in detail in the literature, as well as a 3'-alkylamine linker in U.S. Pat. No. 5,419,966 and a prolinol-based linker, described in U.S. Pat. No. 5,512,667; tri- and tetrafunctional linkers have also been described in U.S. Pat. Nos. 5,451,463, 5,942,610 and 5,696,251; photocleavable linking groups for use in solid phase synthesis have been described in U.S. Pat. No. 5,739,386; trifunctional linkers are also available from Glen Research, Sterling, Va.). Additionally, the linking group W can be acyclic, cyclic, aromatic or a combination thereof, having from 4 to 50 atoms selected from the group consisting of C, N, O, P and S and exclusive of hydrogen atoms that fill available valences, and further having a nitrogen atom directly connected to the adjacent carbonyl group; K is selected from the group consisting of H, OH, SH, NH, $(C_1-C_8)$alkyl, aryl and a nitrogen or hydroxy protecting group, or is combined with W as noted above (such that in some embodiments, K represents a lone pair of electrons); the subscript n is 0 or 1; and when n is 1, Y is a cleavable linking group and L is a solid support; and when n is 0, L is a phosphoramidite or reactive functional group. The dye reagent will preferably have an emission wavelength of from 400 nm to 1200 nm, more preferably, 400 nm to about 850 nm.

In one group of preferred embodiments, n is 1 and Y is a cleavable linking group selected from the group consisting of:

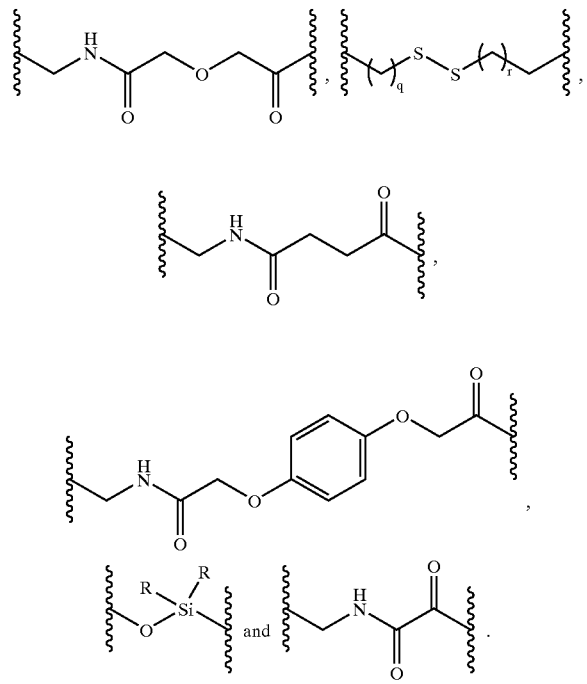

wherein the subscripts q and r are independently integers of from 1 to 15; and each R is independently $(C_1-C_8)$alkyl or $(C_1-C_8)$alkoxy.

In another group of preferred embodiments, $R^A$, $R^B$ and the ring to which each is attached forms a dye selected from the group consisting of a coumarin, a benzocoumarin, a xanthene, a benzo[a]xanthene, a benzo[b]xanthene, a benzo[c]xanthene, a phenoxazine, a benzo[a]phenoxazine, a benzo[b]phenoxazine and a benzo[c]phenoxazine.

In one particularly preferred group of embodiments, the dye reagent has the formula:

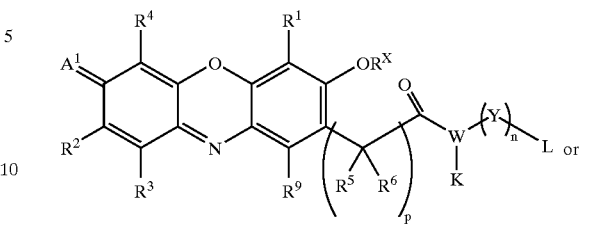

(XIIa)

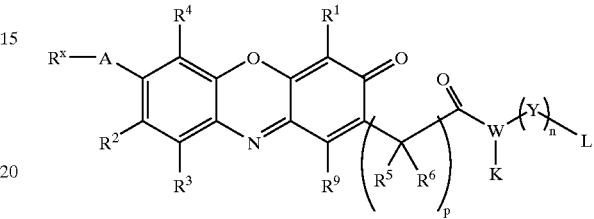

(XIIb)

wherein $A^1$ is O or N—Z in which Z is H or $(C_1-C_8)$alkyl; A is O or NH; $R^x$ is a protecting group; $R^1$, $R^2$, $R^3$, $R^4$ and $R^9$ are each independently selected from the group consisting of H, halogen, cyano, $CF_3$, $(C_1-C_8)$alkyl, $(C_1-C_8)$alkylthio, $(C_1-C_8)$alkoxy, aryl and heteroaryl; each $R^5$ and $R^6$ is independently selected from the group consisting of H, $(C_1-C_8)$alkyl, aryl, heteroaryl, aryl$(C_1-C_4)$alkyl and heteroaryl$(C_1-C_4)$alkyl; wherein the alkyl portions of any of $R^1$ through $R^6$ and $R^9$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and the aryl portions of any of $R^1$ through $R^6$ and $R^9$ are optionally substituted with from one to four substituents selected from the group consisting of halogen, cyano, carboxy, sulfo, hydroxy, amino, mono- or di$(C_1-C_6)$alkylamino, $(C_1-C_6)$alkyl, $(C_1-C_6)$alkylthio and $(C_1-C_6)$alkoxy; optionally, $R^2$ taken together with $R^3$ form a fused aromatic or heteroaromatic ring that is optionally substituted with from one to four substituents selected from halogen cyano, carboxy, sulfo, hydroxy, amino, mono- or di$(C_1-C_6)$alkylamino, $(C_1-C_6)$alkyl, $(C_1-C_6)$alkylthio and $(C_1-C_6)$alkoxy; and tautomeric forms thereof. The letters W, K, Y and L, as well as the subscripts p and n have the meaning provided above with reference to the dye reagents in their general interpretation.

Within this group of embodiments noted above, the dye reagent will more preferably have the formula:

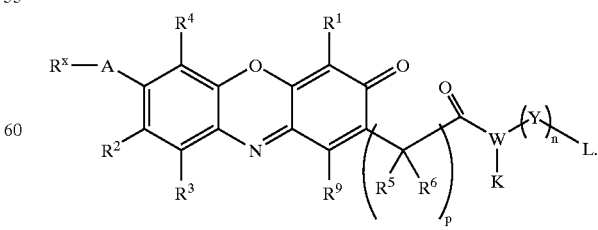

(XIIb)

Reaction Scheme 12 illustrates the preparation of phosphoramidite reagents using chromanone dye precursors.

Reaction Scheme 12

Synthesis of Resorufin-containing phosphoramidite

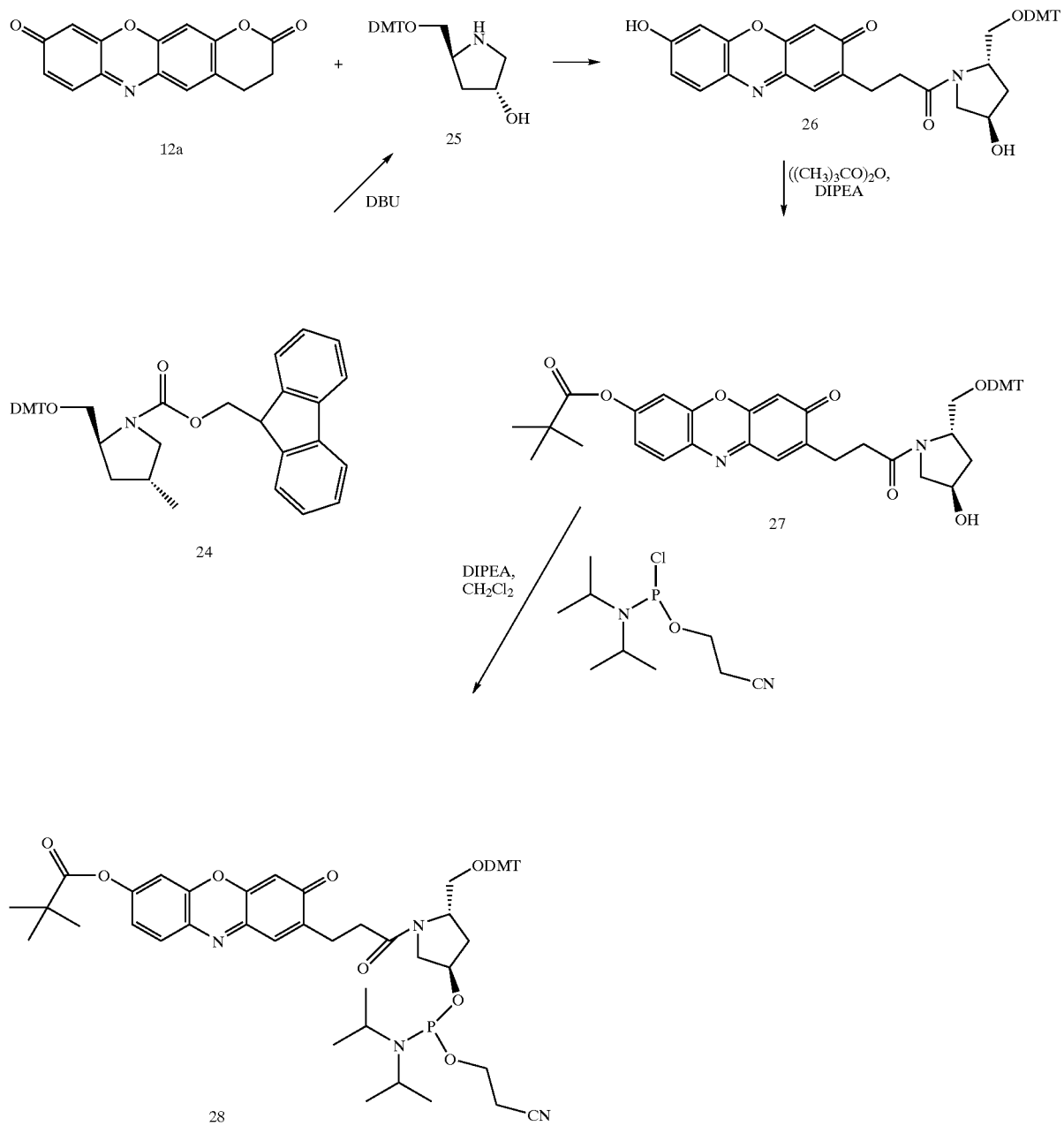

Resorufin phosphoramidite 28 was prepared from 12a in 2 steps in 50% total yield. At the first step, DMT-protected hydroxyprolinol (synthesized from Fmoc-DMT-hydroxyprolinol) was first efficiently reacted with lactone 12a to give DMT-hydroxyprolinol resorufin intermediate 26, which was then directly reacted with trimethylacetic anhydride affording the pivaloyl-protected intermediate 27. At the second step, the secondary hydroxy group of 27 was phosphitylated using 2-cyanoethyldiisopropyl chlorophosphoramidite in the presence of a tertiary amine.

In view of the methodology outlined in Reaction Scheme 12, preferred dye reagents are those having a protected phenoxazine dye attached via a linear or cyclic linking group (e.g., an alkylene, heteroalkylene or prolinol-type linker) to a phosphoramidite moiety. Most preferred is a dye reagent having the formula:

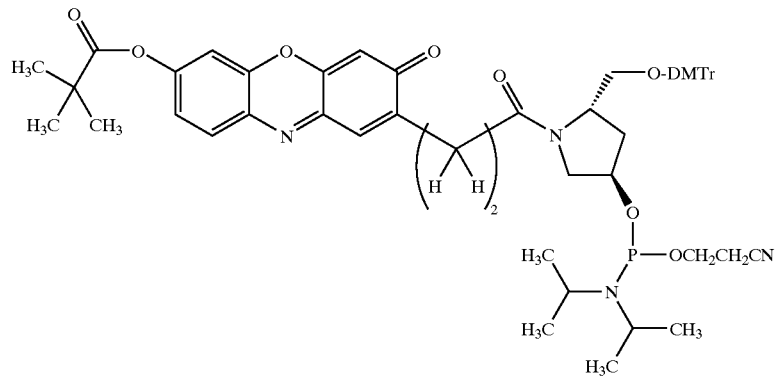

In related embodiments, the present invention provides leuco phenoxazine dye reagents in which the phenoxazine portion is present in a protected form illustrated below.

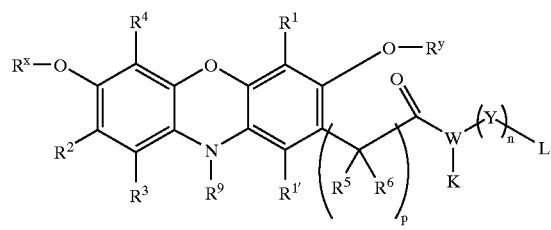

in which each of $R^x$, $R^y$ and $R^z$ are protecting groups, preferably ($C_2$–$C_{20}$)acyl groups (e.g., acetyl, propionyl, pivaloyl, t-butoxycarbonyl, and the like) and the remaining features are as described for the phenoxazine dye reagents above.

In another group of preferred embodiments, the dye reagents are xanthene dye reagents and are represented by the formula:

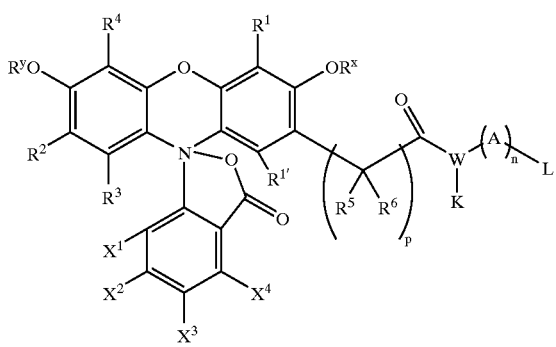

wherein $R^x$ and $R^y$ are independently selected protecting groups; $R^{1'}$, $R^1$, $R^2$, $R^3$ and $R^4$ are each independently selected from the group consisting of H, halogen, cyano, $CF_3$, ($C_1$–$C_8$)alkyl, ($C_1$–$C_8$)alkylthio, ($C_1$–$C_8$)alkoxy, aryl and heteroaryl; each $R^5$ and $R^6$ is independently selected from the group consisting of H, ($C_1$–$C_8$)alkyl, aryl, heteroaryl, aryl($C_1$–$C_4$)alkyl and heteroaryl($C_1$–$C_4$)alkyl; wherein the alkyl portions of any of $R^{1'}$ and $R^1$ through $R^6$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and the aryl portions of any of $R^{1'}$ and $R^1$ through $R^6$ are optionally substituted with from one to four substituents selected from the group consisting of halogen, cyano, carboxy, sulfo, hydroxy, amino, mono- or di($C_1$–$C_6$)alkylamino, ($C_1$–$C_6$)alkyl, ($C_1$–$C_6$)alkylthio and ($C_1$–$C_6$)alkoxy; optionally, $R^2$ taken together with $R^3$ form a fused aromatic or heteroaromatic ring that is optionally substituted with from one to four substituents selected from halogen cyano, carboxy, sulfo, hydroxy, amino, mono- or di($C_1$–$C_6$)alkylamino, ($C_1$–$C_6$)alkyl, ($C_1$–$C_6$)alkylthio and ($C_1$–$C_6$)alkoxy; and tautomeric forms thereof. The letters W, K, Y and L, as well as the subscripts p and n have the meaning provided above with reference to the dye reagents in their general interpretation.

Reaction Scheme 13 illustrates the preparation of a xanthene-containing phosphoramidite reagents. One of skill in the art will appreciate that compound 18d can be replaced by other lactone dyes in the xanthene series (e.g., xanthene, benzo[a]xanthene, benzo[b]xanthene, benzo[c]xanthene) and the linking group (5-aminopentanol) can be substituted with other linear or cyclic linking groups are described herein and in the examples. Use of such substitutions provides access to the full scope of phosphoramidite reagents contemplated by the present invention.

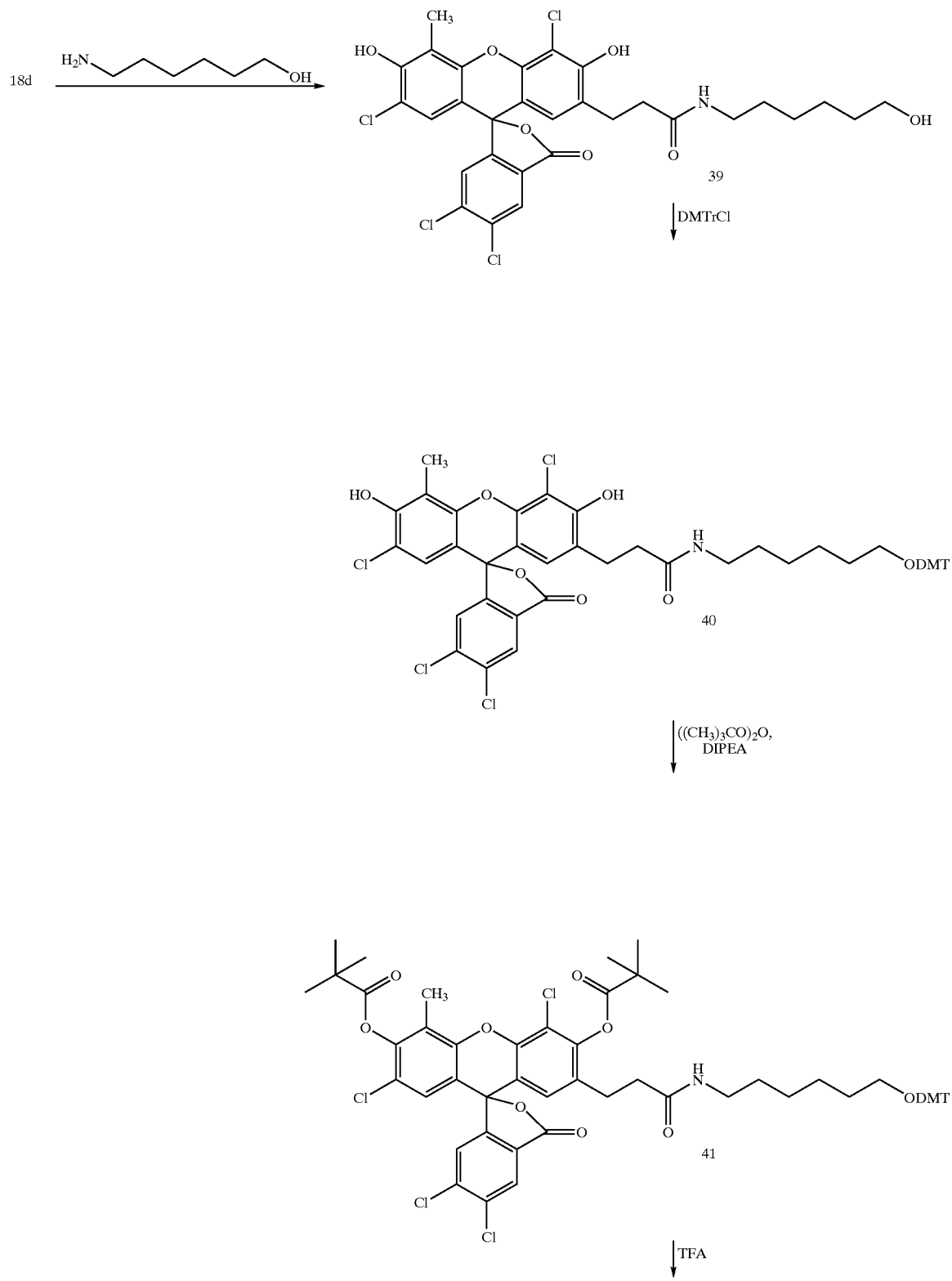

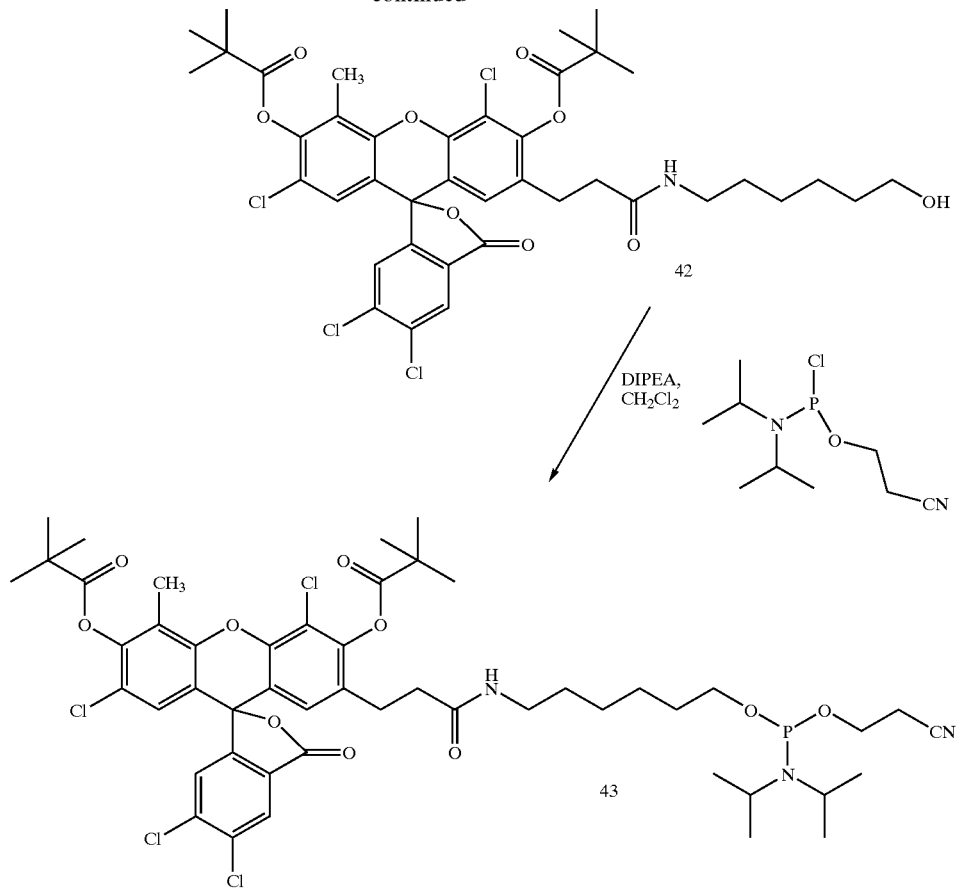

Xanthene-containing phosphoramidite 43 was prepared similarly to amidite 28 starting from lactone 18d. However, in contrast to the synthetic route in Reaction Scheme 12, the primary hydroxy group of 39 was blocked with a transitory protecting DMT group to provide 40 and avoid a competitive reaction with trimethylacetic anhydride during the protection of phenol groups (see compound 41). The DMT group was readily removed from 41 using dilute trifluoroacetic acid solution in 10% methanol in dichloromethane. The resultant dipivaloyl intermediate 42 was converted into phosphoramidite 43 using standard procedures.

Within the xanthene-based dye reagents, the dye reagent is most preferably one selected from the formulae:

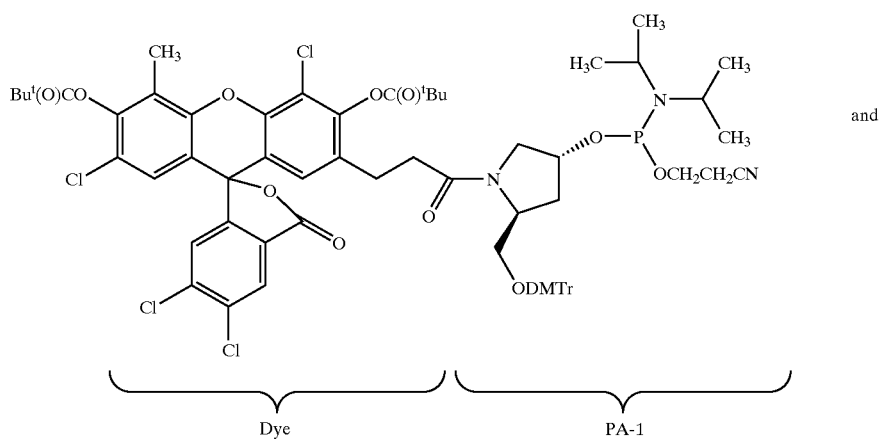

-continued
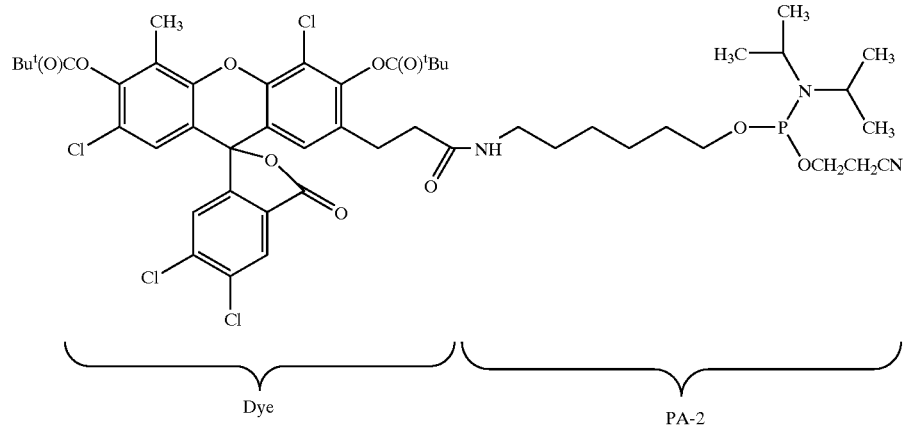
20
Other preferred reagents are those wherein PA-1 or PA-2 are attached to each of the following dyes:
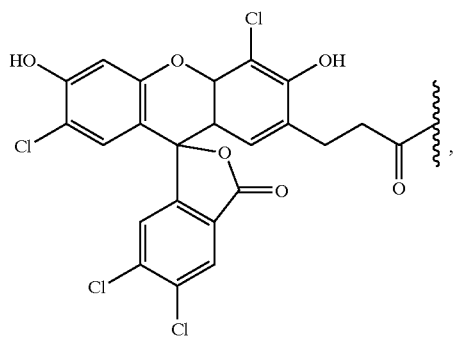
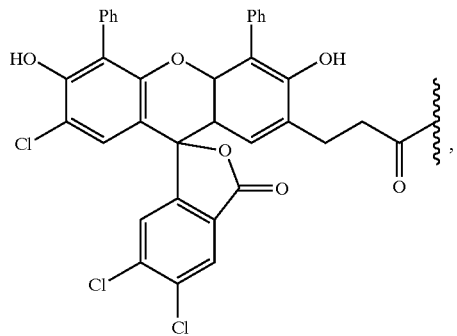
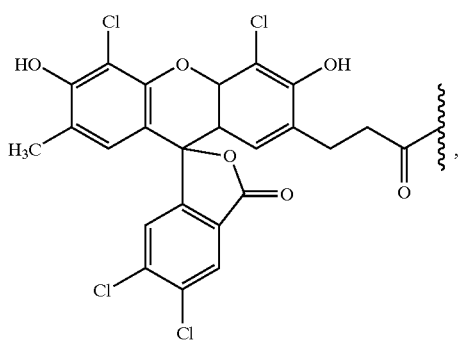
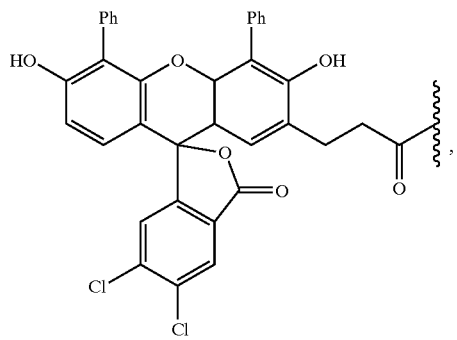
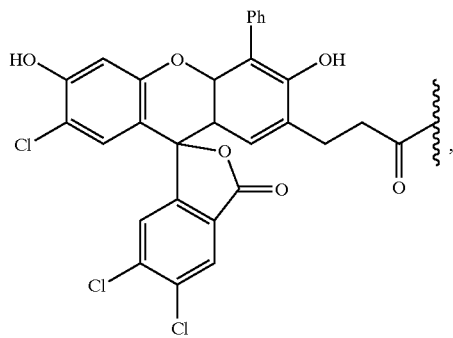
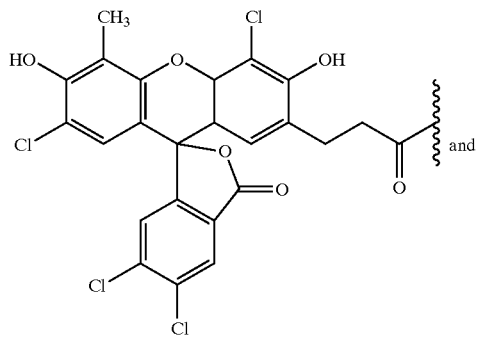

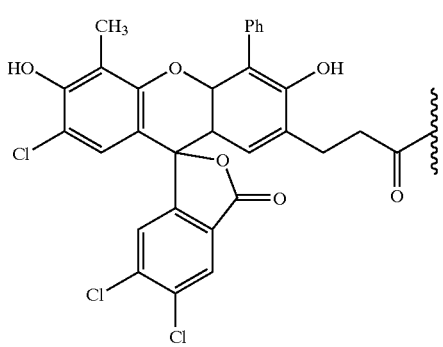

wherein the dyes are shown without protecting groups (e.g., pivaloyl esters) and the wavy line indicates the point of attachment to PA-1 and PA-2.

More generally, one representation of preferred phosphoramidite reagents is provided as:

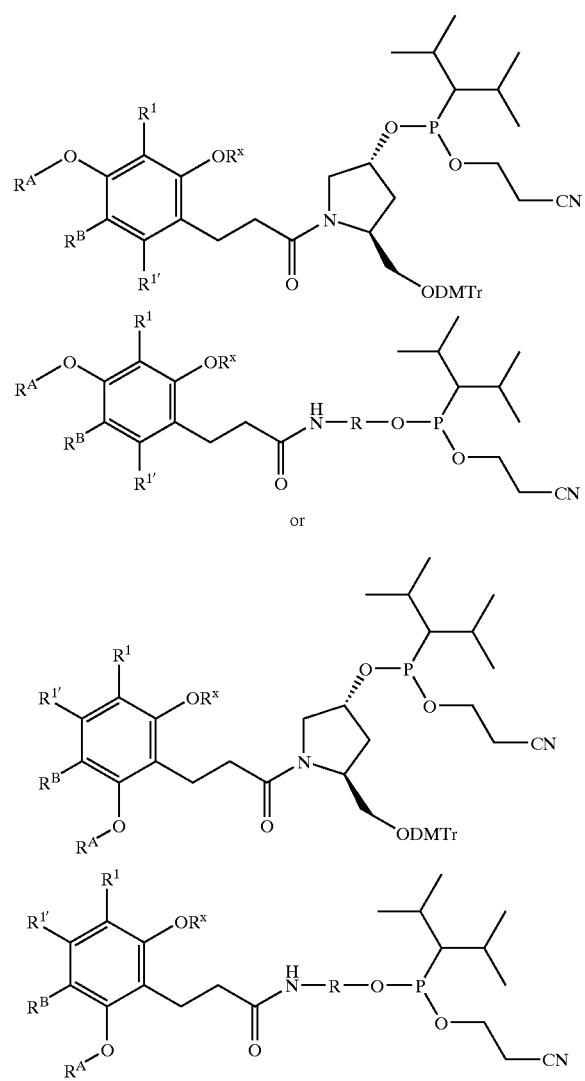

wherein $R^A$, $R^B$, $R^1$, $R^{1'}$ and $R^x$ have the meanings provided above and R is a $(C_2-C_{12})$alkylene or $(C_5-C_{12})$heteroalkylene linking group.

In related embodiments, 5,6-dichlorofluorescein dye reagents are provided. More specifically, these reagents have the formula:

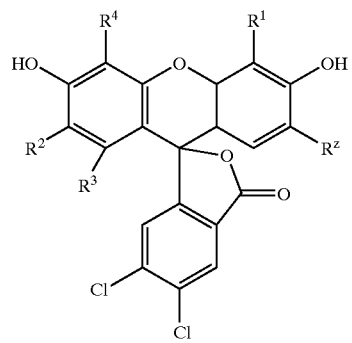

wherein $R^1$, $R^2$, $R^3$ and $R^4$ represent substituents as described above, particularly with reference to formula Ic; $R^z$ represents a substituent selected from the group consisting of H, halogen, cyano, $CF_3$, $(C_1-C_8)$alkyl, $(C_1-C_8)$alkylthio and $(C_1-C_8)$alkoxy; with the additional feature that at least one of $R^z$, $R^1$, $R^2$, $R^3$ and $R^4$ is a linking group.

The present invention further provides oligonucleotide probes having attached dye reagents, preferably 5,6-dichlorofluorescein dye reagents as described above. In some embodiments, the oligonucleotide probe will further comprise an attached quencher for use in assays such as linear beacon assays. In still other embodiments, the oligonucleotide probe will have an attached minor groove binder. A variety of quenchers and minor groove binders are known in the art along with methods for their attachment to oligonucleotide probes (see, for example, co-pending application Ser. Nos. 09/447,936; 09/457,616; and 09/876,830). In the most preferred embodiments, the quencher and minor groove binder components are attached to the 5'-end of the oligonucleotide probe with the 5,6-dichlorofluorescein dye attached at the 3'-end; or alternatively, the quencher and minor groove binder components are attached to the 3'-end of the oligonucleotide probe with the 5,6-dichlorofluorescein dye attached at the 5'-end.

Labeled Modified Bases

The present invention further provides modified bases that are labeled using the fused-lactone dyes described above. A variety of modified bases can be used and are known to those of skill in the art. Essentially, any nucleotide base having an appended reactive functional group can be used, as well as nucleotide analogs (e.g., pyrimidines, purines, pyrazolopyrimidines, deazapurines, and the like). Without intending any limitation on this aspect of the invention, Reaction Scheme 14 illustrates the reaction of a lactone dye with each of two modified bases. These reactions are readily adapted for all lactone dyes herein.

Examples of the reaction of a chromanone dye precursor with amine ligands are shown in Reaction Scheme 14. The 3-substituted pyrazolo[3,4-d]pyrimidines or 5 substituted pyrimidines containing an amino group can be converted to related phophoramidite reagents.

Reaction Scheme 14

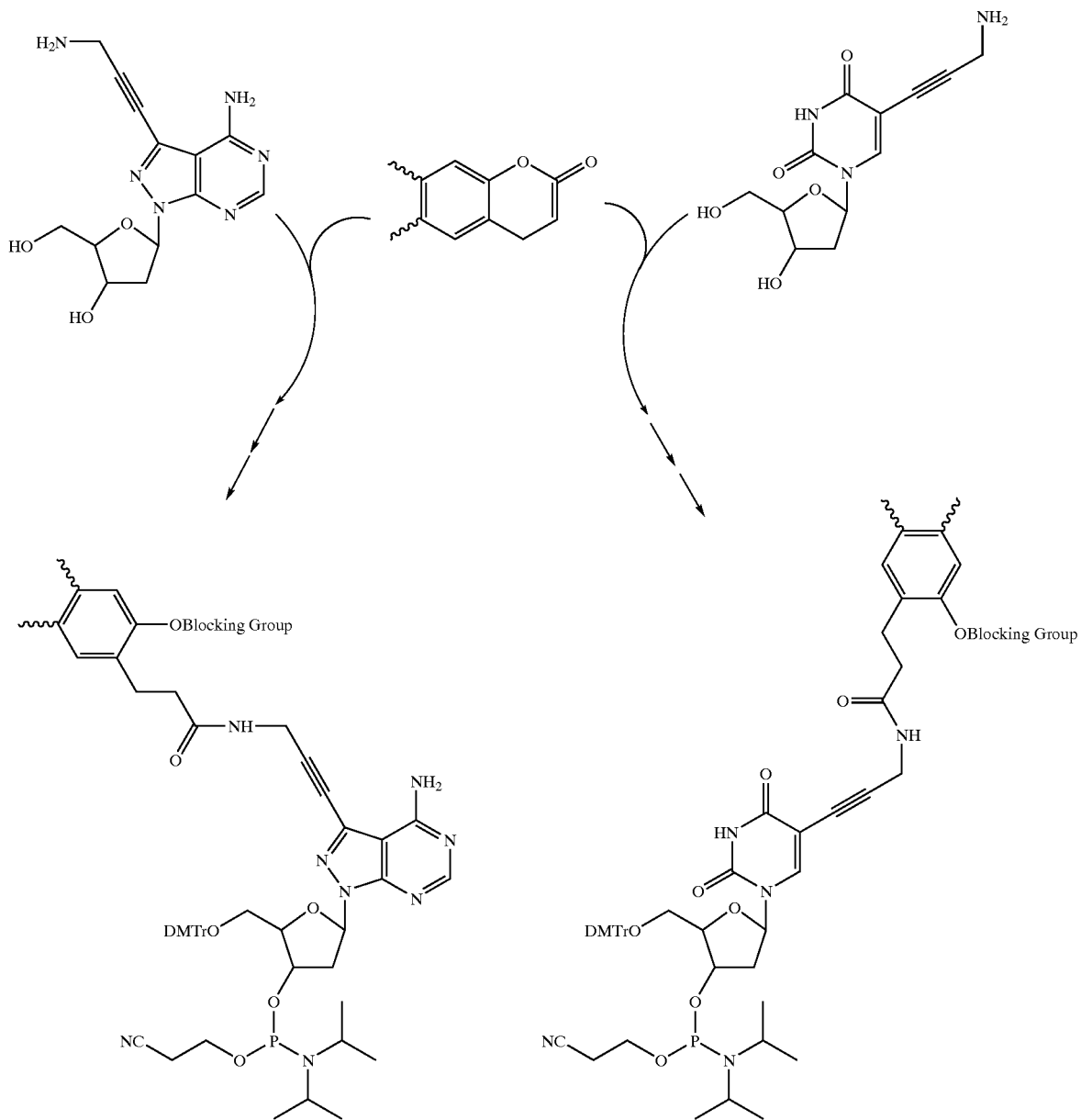

Synthetic Intermediates

Certain intermediates useful in preparing the lactone dyes are also contemplated as an aspect of the present invention. These intermediates have the formula:

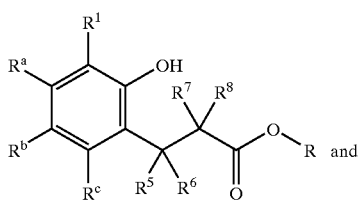

-continued

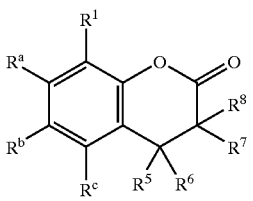

In these formulae, R is an ester group (e.g., lower alkyl, aryl, arylalkyl, and the like); $R^1$, $R^a$, $R^b$ and $R^c$=H, hydroxy, alkyloxy, aryloxy, alkyl, aryl, substituted aryl, heterocyclyl heterocyclic aromatic ring, sulfonyl, sulfamido, amino, amido, halogen, trifluoromethyl, halomethyl, or optionally two adjacent members of $R^1$, $R^a$, $R^b$ and $R^c$ are combined to form a 5–7 membered ring; and $R^5$, $R^6$, $R^7$, $R^8$=H, alkyl, aryl, arylalkyl or optionally, two of $R^5$, $R^6$, $R^7$ and $R^8$ are combined to form a 5–7 membered ring, with the proviso that at least one of $R^a$ or $R^c$ is hydroxy, and at least one of $R^1$ or $R^b$ is hydrogen.

Preferably, $R^1$ and $R^a$, or $R^a$ and $R^b$ or $R^b$ and $R^c$ form an aromatic or non-aromatic ring, or a heterocyclic structure.

In other preferred embodiments, $R^5$ through $R^8$ are H, and $R^a$ is OH. More preferably, $R^c$ is H and R is methyl or ethyl. Still more preferably, $R^1$ is Cl, F or phenyl (see below).

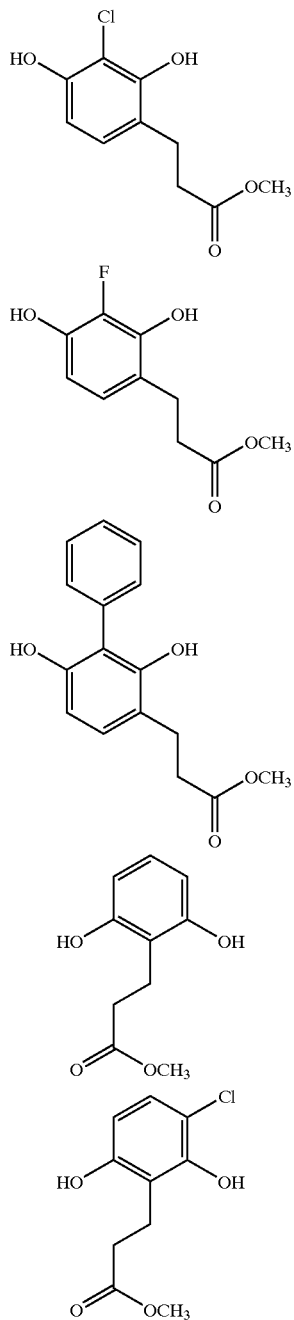

EXAMPLES

Instrumentation: HPLC system equipped with photo diode array (PDA) detector. Column-Rainin C18, Dynamax-100A, SHORT-ONE (4.6×100 mm). Mobile phase was a gradient of acetonitrile (0–100%) in 0.1 M triethylammonium acetate (pH 7.5) in 10 min followed by 10 min 100% acetonitrile wash. Flow rate was 1 ml/min. Sample loop was 20 µl.

Example 1

3-Chloro-2,4-dimethoxybenzaldehyde (2a) was prepared from 1,3-dimethoxybenzene (1a) according to Plattner, J. J. et al. *J. Med. Chem.* 1984, 27-(8), 1016–1026.

3-(3-Chloro-2,4-dimethoxyphenyl)acrylic acid (3a). A solution of compound (2a) (11.07 g, 55.2 mmol), malonic acid (8.639 g, 83 mmol) and piperidine (2 ml, 1.722 g, 20.2 mmol) in 80 ml of anhydrous pyridine was refluxed (bath temperature 110° C.) for 2 h. Reaction mixture was cooled, concentrated under vacuum and acidified 250 ml of 5% aqueous citric acid to a pH of 3. Resulted heterogeneous mixture was sonicated for a few minutes. The precipitated material was filtered off, washed with water (2×20 ml) and dried in vacuum over KOH to give 12.7 g (52.3 mmol, 95% yield) of pure (HPLC, $^1$H NMR) desired acid 3a as a white solid. $^1$H NMR (DMSO-$d_6$): δ 7.77 (d, J=9.0 Hz, 1H), 7.67 (d, J=16.0 Hz, 1H), 7.01 (d, J=9.0 Hz, 1H), 6.51 (d, J=16.0 Hz, 1H), 3.90 (s, 3H), 3.77 (s, 3H).

3-(3-Chloro-2,4-dimethoxyphenyl)propionic acid (4a). A suspension of 3a (12.57 g, 51.88 mmol) in a mixture of MeOH (50 ml) and THF (200 ml) was hydrogenated at 50 psi in the presence of 10% Pd/C (0.3 g) for 4 h. The catalyst was removed by filtration through Celite and the filtrate was concentrated to afford 12.6 g (51.5 mmol, 99% yield) of analytically pure (HPLC, $^1$H NMR) 4a as a white solid. $^1$H NMR (DMSO-$d_6$): δ 7.15 (d, J=8.6 Hz, 1H), 6.86 (d, J=8.6 Hz, 1H), 3.81 (s, 3H), 3.75 (s, 3H), 2.78 (t, J=7.5 Hz, 2H), 2.49 (t, J=7.5 Hz, 2H).

Methyl 3-(3-chloro-2,4-dihydroxyphenyl)propanoate (5a). A solution of 1 (10.0 g, 40.9 mmol) in a mixture of acetic acid (75 ml, 78.67 g, 1.3 mol) and 48% aqueous hydrobromic acid (75 ml, 111.75 g, 0.66 mol) was refluxed (bath temperature +120° C.) for 15 h. Reaction mixture was cooled and concentrated under vacuum. The obtained solid material was dried by co-evaporation with toluene (3×100 ml) and dissolved in 100 ml of methanol. Hydrogen chloride was bubbled for 5 min. The resultant hot solution was allowed to cool to room temperature and then concentrated. The crude product was chromatographed on silica gel eluting with 1:4 EtOAc-hexane. Concentration of the pure product fractions afforded 9.2 g (98%) of the title compound as a pale tan oil, which slowly solidified during drying in vacuo. $^1$H NMR (DMSO-$d_6$): δ 9.80 (s, 1H), 8.95 (s, 1H), 6.81 (d, J=8.4 Hz, 1H), 6.38 (d, J=8.4 Hz, 1H), 3.57 (s, 3H), 2.73 (t, J=7.5 Hz, 2H), 2.50 (t, J=7.5 Hz, 2H).

Compounds 2b, 3b, 4b and 5b were synthesized in similar yields using the procedures described for corresponding chloroanalogs.

3-Fluoro-2,4-dimethoxybenzaldehyde (2b). $^1$H NMR (DMSO-$d_6$): δ 10.11 (s, 1H), 7.56 (dd, J=9 Hz, J=2 Hz, 1H), 7.08 (t, J=8 Hz, 1H), 4.00 (d, J=2, 3H), 3.93 (s, 3H).

(2E)-3-(3-Fluoro-2,4-dimethoxyphenyl)prop-2-enoic acid (3b). $^1$H NMR (DMSO-$d_6$): δ 12.36 (s, 1H), 7.66 (d, J=16 Hz, 1H), 7.56 (d, J=8.5 Hz, 1H), 6.96 (t, J=8.5 Hz, 1H), 6.57 (d, J=16 Hz, 1H), 3.89 (s, 3H), 3.87 (s, 3H).

3-(3-Fluoro-2,4-dimethoxyphenyl)propanoic acid (4b). $^1$H NMR (DMSO-d$_6$): δ 11.8 (br s, 1H), 6.93 (d, J=8.5 Hz, 1H), 6.80 (t, J=8.5 Hz, 1H), 3.83 (s, 3H), 3.79 (s, 3H), 2.74 (t, J=7.5 Hz, 2H), 2.43 (t, J=7.5 Hz, 2H).

Methyl 3-(3-fluoro-2,4-dihydroxyphenyl)propanoate (5b). $^1$H NMR (DMSO-d$_6$): δ 9.47 (s, 1H), 9.33 (s, 1H), 6.62 (d, J=8.5 Hz, 1H), 6.29 (t, J=8.5 Hz, 1H), 3.56 (s, 3H), 2.70 (t, J=7.5 Hz, 2H), 2.49 (t, J=7.5 Hz, 2H).

2,4-Dimethoxy-3-phenylbenzaldehyde (2c). Compound 2c was synthesized from 1c in 95% yield using the procedure described for 2a. $^1$H NMR(acetone-d$_6$): δ 10.28 (s, 1H), 7.88 (d, J=8.8 Hz, 1H), 7.42–7.49 (m, 5H), 7.10 (d, J=8.8 Hz, 1H), 3.89 (s, 3H), 3.48 (s, 3H).

(2E)-3-(2,4-Dimethoxy-3-phenylphenyl)prop-2-enoic acid (3c). Compound 3c was synthesized from 2c in 96% yield using the procedure described for 3a. $^1$H NMR (DMSO-d$_6$): δ 7.81 (d, J=8.8 Hz, 1H), 7.74 (d, J=16.0 Hz, 1H), 7.28–7.42 (m, 5H), 6.97 (d, J=8.8 Hz, 1H), 6.47 (d, J=16.0 Hz, 1H), 3.73 (s, 3H), 3.25 (s, 3H).

3-(2,4-Dimethoxy-3-phenylphenyl)propanoic acid (4c). Compound 4c was synthesized from 3c in 98% yield using the procedure described for 4a. $^1$H NMR (DMSO-d$_6$): δ 12.0 (br s, 1H), 7.39 (m, 2H), 7.29 (m, 3H), 7.18 (d, J=8.5 Hz, 1H), 6.80 (d, J=8.5 Hz, 1H), 3.64 (s, 3H), 3.18 (s, 3H), 2.78 (t, J=7.5 Hz, 2H), 2.50 (t, J=7.5 Hz, 2H).

Methyl 3-(2,4-dihydroxy-3-phenylphenyl)propanoate (5c). BBr$_3$ (4.72 g, 1.78 ml, 18.9 mmol) was carefully added through a syringe over 5 min to a stirred solution of dimethoxy acid 4c (1.35 g, 4.7 mmol) in anhydrous CH$_2$Cl$_2$ (20 ml). Resulted mixture was magnetically stirred for 8 h and concentrated under vacuum. The residue was co-evaporated with toluene (2×20 ml), dissolved in methanol (20 ml) and HCl gas was bubbled into the solution for 2 min. The material obtained after evaporation of the solvent was partitioned between cold water (30 ml) and ethyl acetate (100 ml). The organic phase was washed with saturated NaHCO$_3$ (2×10 ml), brine (20 ml), dried over MgSO$_4$ and concentrated. The resultant crude product was chromatographed on a short silica gel column eluting with ethyl acetate. Pure product fractions were concentrated to afford 1.2 g (94%) of 5c as a tan oil. $^1$H NMR (DMSO-d$_6$): δ 8.95 (s, 1H), 7.82 (s, 1H), 7.24–7.36 (m, 5H), 6.83 (d, J=8.2 Hz, 1H), 6.38 (d, J=8.2 Hz, 1H), 3.59 (s, 3H), 2.75 (t, J=8.0 Hz, 2H), 2.52 (t, J=8.0 Hz, 2H).

Methyl 3-(8-chloro-7-hydroxy-4-methyl-2-oxo-2H-chromen-6-yl)propanoate (6a). Diketene (0.7 ml, 9.1 mmol) was added dropwise to a stirred solution of 5a (1.0 g, 4.3 mmol) in 7 ml of methanesulfonic acid. The resultant solution was heated at 70° C. for 5 min and cooled. Methanol (20 ml) was added and the reaction was heated to boiling; this treatment esterified small amount of free acid formed during the cyclization step. Methanol was evaporated and water was added to precipitate the product. The crude material was chromatographed on silica eluting with ethyl acetate. Concentration of the pure product fractions and drying under vacuum afforded 0.82 g (64%) of the desired product as a pale yellow solid. $^1$H NMR (DMSO-d$_6$): δ 10.45 (s, 1H), 7.50 (s, 1H), 6.24 (s, 1H), 3.59 (s, 3H), 2.93 (t, J=7.5 Hz, 2H), 2.62 (t, J=7.5 Hz, 2H), 2.38 (s, 3H).

3-(8-Chloro-7-hydroxy-4-methyl-2-oxo-2H-chromen-6-yl)propanoic acid (7a). Ester 6a (0.75 g, 2.5 mmol) was dissolved in 10 ml of 1N NaOH. After being kept at room temperature for 30 min the solution was acidified with 1N HCl to pH of 3. The precipitated material was collected by filtration and washed with water. Drying under vacuum over P$_2$O$_5$ afforded 0.705 g of acid 7a as an off-white solid. $^1$H NMR (DMSO-d$_6$): δ 12.2 (br s, 1H), 10.41 (br s, 1H), 7.50 (s, 1H), 6.23 (s, 1H), 2.89 (t, J=7.5 Hz, 2H), 2.53 (t, J=7.5 Hz, 2H), 2.38 (s, 3H).

10-Chloro-6-methyl-2H-pyrano[5,6-g]chromane-2,8-dione (8a). Pentafluorophenyl trifluoroacetate (PFP-TFA) (0.4 ml, 2.3 mmol) was added to a solution of 7a (0.65 g, 2.3 mmol) and triethylamine (0.5 ml) in 8 ml of anhydrous CH$_2$Cl$_2$ and the reaction was stirred for 1 h. The precipitated product was filtered off and washed with ethyl acetate. Drying under vacuum afforded 0.5 g (82%) of the desired lactone as a pale yellow solid. $^1$H NMR (DMSO-d$_6$): δ 7.73 (s, 1H), 6.43 (s, 1H), 3.13 (t, J=7.5 Hz, 2H), 2.89 (t, J=7.5, 2H), 2.43 (s, 3H).

10-Fluoro-6-methyl-2H-pyrano[5,6-g]chromane-2,8-dione (8b) was synthesized from compound 5b by analogy with chloro analog 8a with similar chemical yield.

Methyl 3-(8-fluoro-7-hydroxy-4-methyl-2-oxo-2H-chromen-6-yl)propanoate (6b). $^1$H NMR (DMSO-d$_6$): δ 10.85 (s, 1H), 7.33 (s, 1H), 6.21 (s, 1H), 3.59 (s, 3H), 2.89 (t, J=7.5 Hz, 2H), 2.62 (t, J=7.5 Hz, 2H), 2.36 (s, 3H).

3-(8-Fluoro-7-hydroxy-4-methyl-2-oxo-2H-chromen-6-yl)propanoic acid (7b). $^1$H NMR (DMSO-d$_6$): δ 12.2 (br s, 1H), 10.81 (br s, 1H), 7.33 (s, 1H), 6.21 (s, 1H), 2.88 (t, J=7.5 Hz, 2H), 2.52 (t, J=7.5 Hz, 2H), 2.36 (s, 3H).

10-Fluoro-6-methyl-2H-pyrano[5,6-g]chromane-2,8-dione (8b). $^1$H NMR (DMSO-d$_6$): δ 7.56 (s, 1H), 6.42 (s, 1H), 3.13 (t, J=7.5 Hz, 2H), 2.89 (t, J=7.5, 2H), 2.41 (s, 3H).

Compounds 9a, 9b, 9c were synthesized by the general procedure described for 4-nitrosoresorcinol (Kendall et. al. J. Amer. Chem. Soc. 82: 1853–4 (1960)).

Methyl 3-(7-hydroxy-10-oxido-3-oxo-3H-phenoxazin-8-yl)propanoate (10a). 4-Nitrosoresorcinol (9a) (33.13 g, 238 mmol), synthesized by the procedure of Kendall et. al. J. Amer. Chem. Soc. 82: 1853–4 (1960) was dissolved in 1.1 L of methanol at +40° C. with sonication. Resultant solution was transferred into a 3 L round bottom flask and cooled to +2° C. using an ice-water bath. A solution of ester 5d (46.8 g, 238 mmol) in methanol (100 ml) and MnO$_2$ (20.68 g, 238 mmol) were added and the mixture was allowed to cool to 0–2° C. Concentrated sulfuric acid (25.5 ml, 46.9 g, 478 mmol) was added over 2 min with cooling and intensive stirring. The resultant mixture was stirred at room temperature for 4 h and then diluted with ether (1.2 L). Precipitated material was collected by filtration, washed with MeOH/ether (1:1) mixture (2×100 ml) and ether (2×100 ml). Drying under vacuum afforded 26.32 g of 10a (35%) as a black-brown solid, m.p. 233° C. (dec.). $^1$H NMR (DMSO-d$_6$): δ 11.24 (bs, 1H), 8.00 (d, J=9.1 Hz, 1H), 7.83 (s, 1H), 6.88 (br d, J=9.1 Hz, 1H), 6.82 (br s, 1H), 6.20 (b s, 1H), 3.59 (s, 3H), 2.75 (t, J=7.3 Hz, 2H), 2.59 (t, J=7.3 Hz, 2H).

Compounds 10b, 10c, 10d, 10e were prepared by analogy with the non-halogenated analog 10a.

Methyl 3-(6-chloro-7-hydroxy-10-oxido-3-oxo-3H-phenoxazin-8-yl)propanoate (10b). $^1$H NMR (DMSO-d$_6$): δ 11.4 (br s, 1H), 8.05 (d, J=7 Hz, 1H), 7.87 (s, 1H), 6.88 (m, 2H), 3.59 (s, 3H), 2.80 (t, J=7.5 Hz, 2H), 2.61 (t, J=7.5 Hz, 2H).

Methyl 3-(6-fluoro-7-hydroxy-10-oxido-3-oxo-3H-phenoxazin-8-yl)propanoate (10c). $^1$H NMR (DMSO-d$_6$): δ 11.35 (br s, 1H), 8.05 (d, J=7 Hz, 1H), 7.81 (s, 1H), 6.95 (m, 2H), 3.59 (s, 3H), 2.79 (t, J=7.5 Hz, 2H), 2.61 (t, J=7.5 Hz, 2H).

Methyl 3-(6-fluoro-7-hydroxy-10-oxido-3-oxo-3H-phenoxazin-8-yl)propanoate (10d). $^1$H NMR (DMSO-d$_6$): δ 11.80 (br s, 1H), 7.86 (d, J=9 Hz, 1H), 7.83 (s, 1H), 7.07 (t, J=9 Hz, 1H), 3.59 (s, 3H), 2.79 (t, J=7.5 Hz, 2H), 2.62 (t, J=7.5 Hz, 2H).

3-(7-Hydroxy-3-oxo-3H-phenoxazin-8-yl)propanoic acid (11a). Methyl ester (10a) (22.83 g, 72.4 mmol) was dissolved in 400 ml of 0.5 M aqueous sodium hydroxide and the solution was stirred for 1 h. A solution of sodium dithionite solution (200 ml, 100 mmol) was added and reaction mixture was stirred for additional 15 minutes. To precipitate the product 3 M hydrochloric acid (80 ml) was carefully added and resultant suspension was stirred for 10 min and centrifuged. The supernatant was decanted and the residue was re-suspended in ~800 ml of water and centrifuged again. This operation was repeated one more time. Final supernatant had pH of 3–4. The centrifuged material was dried under vacuum overnight at 40° C. to afford 14.12 g (68%) of desired product (11a) as a brown solid. $^1$H NMR (CD$_3$OD, +40° C.): δ 7.64 (d, J=9.0 Hz, 1H), 7.39 (s, 1H), 6.89 (d, J=9.0 Hz, 1H), 6.74 (s, 1H), 6.34 (s, 1H), 2.63 (m, 2H), 2.51 (m, 2H).

Compounds 11b, 11c, 11d, 11e were prepared by analogy with the non-halogenated analog 11a.

3-(4-Chloro-7-hydroxy-3-oxophenoxazin-2-yl)propanoic acid (11b). $^1$H NMR (DMSO-d$_6$): δ 12.2 (br s, 1H), 11.2 (br s, 1H), 7.74 (d, J=9 Hz, 1H), 7.39 (s, 1H), 6.96 (d, J=9 Hz, 1H), 6.91 (s, 1H), 2.76 (t, J=7.5 Hz, 2H), 2.56 (t, J=7.5 Hz, 2H).

3-(4-Fluoro-7-hydroxy-3-oxophenoxazin-2-yl)propanoic acid (11c). $^1$H NMR (DMSO-d$_6$): δ 12.2 (br s, 1H), 11.2 (br s, 1H), 7.70 (d, J=8.5 Hz, 1H), 7.34 (s, 1H), 6.92 (d, J=8.5 Hz, 1H), 6.90 (s, 1H), 2.74 (t, J=7.5 Hz, 2H), 2.53 (t, J=7.5 Hz, 2H).

3-(4,6-Difluoro-7-hydroxy-3-oxophenoxazin-2-yl)propanoic acid (11d). $^1$H NMR (DMSO-$_6$): δ 12.2 (br s, 1H), 11.6 (br s, 1H), 7.54 (d, J=8.5 Hz, 1H), 7.35 (s, 1H), 6.92 (t, J=8.5 Hz, 1H), 2.75 (t, J=7.5 Hz, 2H), 2.54 (t, J=7.5 Hz, 2H).

3-(4,6,8-Trifluoro-7-hydroxy-3-oxophenoxazin-2-yl)propanoic acid (11e). $^1$H NMR (DMSO-d$_6$): δ 12.2 (br s, 1H), 11.6 (br s, 1H), 7.65 (d, J=10 Hz, 1H), 7.44 (s, 1H), 2.83 (t, J=7.5 Hz, 2H), 2.56 (t, J=7.5 Hz, 2H).

3,4-dihydro-2H-pyrano[3,2-b]phenoxazine-2,9-dione (12a)

To a suspension of acid 12a (10.36 g, 36.3 mmol) in anhydrous DMF (200 ml) was added N,N,-diisopropylethylamine (26.13 ml, 150 mmol) and resultant mixture was magnetically stirred for 10 min. The reaction flask was placed in water bath (t~+20° C.) and PFP-TFA (18.9 ml, 110 mmol) was added through a syringe during 5–10 min. After being stirred for 2 h, the reaction mixture was concentrated under vacuum and diluted with ether (200 ml). The precipitated material was filtered off and washed with ether (2×30 ml), 2-propanol (2×50 ml) and ether (3×30 ml). Drying under vacuum afforded 6.56 g (67%) of the desired lactone 12a as an orange solid m.p. 268° C. (dec.). $^1$H NMR (DMSO-d$_6$, +45° C.): δ 7.81 (s, 1H), 7.54 (d, J=9.8 Hz, 1H), 7.27 (s, 1H), 6.82 (dd, J=9.8 Hz, J=2.1 Hz, 1H), 6.29 (d, J=2.1 Hz, 1H), 3.12 (m, 2H), 2.88 (m, 2H).

Compounds 12b, 12c, 12d, 12e were prepared by analogy with the non-halogenated analog 12a.

12-Chloro-3,4-dihydro-2H-pyrano[3,2-b]phenoxazine-2,9-dione (12b). $^1$H NMR (DMSO-d$_6$, +45° C.): δ 7.80 (s, 1H), 7.57 (d, J=9.8 Hz, 1H), 6.85 (d, J=9.8 Hz, 1H), 6.39 (s, 1H), 3.16 (t, J=7.5 Hz, 2H), 2.91 (t, J=7.5 Hz, 2H).

12-Fluoro-3,4-dihydro-2H-pyrano[3,2-b]phenoxazine-2,9-dione (12c). $^1$H NMR (DMSO-d$_6$, +45° C.): δ 7.65 (s, 1H), 7.57 (d, J=9.8 Hz, 1H), 6.84 (d, J=9.8 Hz, 1H), 6.42 (s, 1H), 3.16 (t, J=7.5 Hz, 2H), 2.92 (t, J=7.5 Hz, 2H).

10,12-Difluoro-3,4-dihydro-2H-pyrano[3,2-b]phenoxazine-2,9-dione (12d). $^1$H NMR (DMSO-d$_6$): δ 7.70 (s, 1H), 7.61 (d, J=9.9 Hz, 1H), 6.84 (dd, J$_1$=9.9 Hz, J$_2$=1 Hz, 1H), 3.18 (t, J=7.5 Hz, 2H), 2.93 (t, J=7.5 Hz, 2H).

8,10,12-Trifluoro-3,4-dihydro-2H-pyrano[3,2-b]phenoxazine-2,9-dione (12e). $^1$H NMR (DMSO-d$_6$): δ 7.77 (s, 1H), 7.72 (d, J=10 Hz, 1H), 3.20 (t, J=7.5 Hz, 2H), 2.94 (t, J=7.5 Hz, 2H).

3,4,5,6-tetrachloro-2-({3-chloro-2,4-dihydroxy-5-[2-(methoxycarbonyl)ethyl]phenyl}carbonyl)benzoic acid (14a). Tetrachlorophthalic anhydride (17.4 g, 60.8 mmol) was suspended in 160 ml of anhydrous 1,2-dichloroethane and stirred for 30 min to dissolve most of the solid. AlCl$_3$ (21.0 g, 158 mmol) was added in one portion (light exotherm) followed by addition of ester 5a (14.0 g, 60.7 mmol) as a solution in anhydrous 1,2-dichloroethane (80 ml). The mixture was stirred for 15–20 min to give a clear solution. Then reaction mixture was stirred at room temperature for another 20 h. By that time the starting compounds were almost completely consumed according to the HPLC analysis.

The solvent was evaporated and the resulting gummy residue was partitioned between ethyl acetate (500 ml) and cold 5 N HCl (500 ml). The aqueous phase was extracted with more ethyl acetate, the combined organic solution was washed with 1 N HCl (300 ml), saturated NaCl (300 ml) and dried over MgSO$_4$. Concentration of the solution gave a pale yellow solid; it was triturated with CH$_2$Cl$_2$ (200 ml), cooled to 0° C. and then filtered off. Washing with CH$_2$Cl$_2$ (2×50 ml) and drying under vacuum afforded 21.0 g of the desired product as a white solid. The mother liquor afforded additional 2.1 g of the product. Total yield was 23.1 g (74%). $^1$H NMR (DMSO-d$_6$): δ 11.95 (bs, 1H), 11.05 (bs, 1H), 7.21 (s, 1H), 3.54 (s, 3H), 2.75 (m, 2H), 2.45 (m, 2H).

Compounds 14b–14n were synthesized analogously to 14a.

3,4,5,6-Tetrafluoro-2-({3-fluoro-2,4-dihydroxy-5-[2-(methoxycarbonyl)ethyl]phenyl}carbonyl)benzoic acid (14b). $^1$H NMR (DMSO-d$_6$): δ 12.0 (bs, 1H), 11.05 (bs, 1H), 7.02 (s, 1H), 3.54 (s, 3H), 2.72 (t, J=7.5 Hz, 2H), 2.45 (m, 2H).

3,4,5,6-Tetrachloro-2-({3-fluoro-2,4-dihydroxy-5-[2-(methoxycarbonyl)ethyl]phenyl}carbonyl)benzoic acid (14c). $^1$H NMR (DMSO-d$_6$): δ 11.3 (bs, 1H), 11.1 (bs, 1H), 7.17 (s, 1H), 3.55 (s, 3H), 2.72 (m, 2H), 2.45 (m, 2H).

2-({3-Chloro-2,4-dihydroxy-5-[2-(methoxycarbonyl)ethyl]phenyl}carbonyl)-3,4,5,6-tetrafluorobenzoic acid (14d). $^1$H NMR (DMSO-d$_6$): δ 11.94 (bs, 1H), 10.99 (bs, 1H), 7.19 (s, 1H), 3.54 (s, 3H), 2.74 (t, J=7.2 Hz, 2H), 2.46 (t, J=7.4 Hz, 2H).

4,5-Dichloro-2-({3-chloro-2,4-dihydroxy-5-[2-(methoxycarbonyl)ethyl]phenyl}carbonyl)benzoic acid (14e). $^1$H NMR (DMSO-d$_6$): δ 12.46 (s, 1H), 8.16 (s, 1H), 7.87 (s, 1H), 6.90 (s, 1H), 3.49 (s, 3H), 2.70 (t, J=7.3 Hz, 2H), 2.42 (t, J=7.3 Hz, 2H).

4,5-Dichloro-2-({3-fluoro-2,4-dihydroxy-5-[2-(methoxycarbonyl)ethyl]phenyl}carbonyl)benzoic acid (14f). $^1$H NMR (DMSO-d$_6$): δ 11.59 (bs, 1H), 11.13 (bs, 1H), 8.13 (s, 1H), 7.82 (s, 1H), 6.83 (s, 1H), (s, 1H), 3.50 (s, 3H), 2.67 (t, J=7.5 Hz, 2H), 2.43 (t, J=7.5 Hz, 2H).

2-({2,4-Dihydroxy-5-[2-(methoxycarbonyl)ethyl]phenyl}carbonyl)-3,4,5,6-tetrafluorobenzoic acid (14g). $^1$H NMR (DMSO-d$_6$): δ 11.2 (bs, 1H), 11.04 (bs, 1H), 7.02 (s, 1H), 6.37 (s, 1H), 3.54 (s, 3H), 2.65 (t, J=7.5 Hz, 2H), 2.46 (t, J=7.5 Hz, 2H).

2-({3-Chloro-2,4-dihydroxy-5-[2-(methoxycarbonyl)ethyl]phenyl}carbonyl)benzoic acid (14h). $^1$H NMR (DMSO-d$_6$): δ 11.75 (bs, 1H), 8.02 (d, J=7.2 Hz, 1H), 7.68 (m, 2H), 7.44 (d, J=7.2 Hz, 1H), 6.75 (s, 1H), 3.45 (s, 3H), 2.65 (t, J=7.5 Hz, 2H), 2.39 (t, J=7.5 Hz, 2H).

2-({2,4-Dihydroxy-5-[2-(methoxycarbonyl)ethyl]-3-phenylphenyl}carbonyl)benzoic acid (14i). $^1$H NMR (DMSO-d$_6$): δ 7.95 (m, 1H), 7.25–7.55 (m, 9H), 6.75 (s, 1H), 2.62 (t, J=7.4 Hz, 2H), 2.39 (t, J=7.3 Hz, 2H).

2-({2,4-Dihydroxy-5-[2-(methoxycarbonyl)ethyl]-3-phenylphenyl}carbonyl)-4,5-dichlorobenzoic acid (14j). $^1$H NMR (DMSO-d$_6$): δ 7.36–7.41 (m, 2H), 7.32–7.20 (m, 3H), 7.11 (bs, 1H), 3.54 (s, 3H), 2.73 (m, 2H), 2.49 (m, 2H).

2-({2,4-Dihydroxy-5-[2-(methoxycarbonyl)ethyl]-3-phenylphenyl}carbonyl)-3,4,5,6-tetrachlorobenzoic acid (14k). $^1$H NMR (DMSO-d$_6$): δ 12.25 (s, 1H), 9.55 (s, 1H), 8.17 (s, 1H), 7.88 (s, 1H), 7.20–7.47 (m, 5H), 6.90 (s, 1H), 3.50 (s, 3H), 2.70 (t, J=7.0 Hz, 2H), 2.43 (t, J=7.1 Hz, 2H).

2-({2,4-Dihydroxy-5-[2-(methoxycarbonyl)ethyl]phenyl}carbonyl)benzoic acid (14l). $^1$H NMR (DMSO-d$_6$): δ 12.14 (s, 1H), 10.89 (s, 1H), 8.00 (d, J=7.2 Hz, 1H), 7.62 (m, 2H), 7.39 (d, J=7.2 Hz, 1H), 6.76 (s, 1H), 6.37 (s, 1H), 3.45 (s, 3H), 2.56 (t, J=7.5 Hz, 2H), 2.38 (t, J=7.5 Hz, 2H).

2-({2,4-Dihydroxy-5-[2-(methoxycarbonyl)ethyl]phenyl}carbonyl)-4,5-dichlorobenzoic acid (14m). $^1$H NMR (DMSO-d$_6$): δ 11.71 (s, 1H), 10.93 (s, 1H), 8.12 (s, 1H), 7.77 (s, 1H), 6.92 (s, 1H), 6.37 (s, 1H), 3.49 (s, 3H), 2.60 (t, J=7.5 Hz, 2H), 2.41 (t, J=7.5 Hz, 2H).

2-({3-Fluoro-2,4-dihydroxy-5-[2-(methoxycarbonyl)ethyl]phenyl}carbonyl)benzoic acid (14n). $^1$H NMR (DMSO-d$_6$): δ 12.03 (s, 1H), 11.12 (s, 1H), 8.00 (d, J=7.2 Hz, 1H), 7.62 (m, 2H), 7.42 (d, J=7.2 Hz, 1H), 6.64 (s, 1H), 3.45 (s, 3H), 2.63 (t, J=7.5 Hz, 2H), 2.40 (t, J=7.5 Hz, 2H).

3,6-Dichloro-2-({3-chloro-2,4-dihydroxy-5-[2-(methoxycarbonyl)ethyl]phenyl}carbonyl)benzoic acid (14o). $^1$H NMR (DMSO-d$_6$): δ 12.15 (s, 1H), 11.00 (s, 1H), 7.78 (s, 2H), 6.97 (s, 1H), 3.51 (s, 3H), 2.73 (t, J=7.5 Hz, 2H), 2.44 (t, J=7.5 Hz, 2H).

3,6-Difluoro-2-({3-chloro-2,4-dihydroxy-5-[2-(methoxycarbonyl)ethyl]phenyl}carbonyl)benzoic acid (14p). $^1$H NMR (DMSO-d$_6$): δ 12.19 (br s, 1H), 10.95 (br s, 1H), 7.62 (m, 2H), 7.04 (s, 1H), 3.50 (s, 3H), 2.72 (t, J=7.5 Hz, 2H), 2.44 (t, J=7.5 Hz, 2H).

Methyl 3-(4,5,6,7,13,16-hexachloro-12,15-dihydroxy-1-oxospiro[3-hydroisobenzofuran-3,9'-xanthene]-11-yl)propanoate (16a). 4-Chlororesorcinol (15a) (0.56 g, 3.9 mmol) and 14a (1.0 g, 1.93 mmol) were suspended in 10 ml of methanesulfonic acid. The suspension was stirred at 70° C. under argon for 1 h and cooled. A mixture of ice and water (50 g) was added to precipitate the product. Ethyl acetate (50 ml) was added to extract the precipitate. The product from organic layer was extracted with sodium bicarbonate solution. The aqueous phase was washed with ether to remove excess 4-chlororesorcinol and acidified with concentrated hydrochloric acid. The precipitated material, pure product 16a, was taken up in ethyl acetate and dried over Na$_2$SO$_4$. Concentration of the solution and drying under vacuum afforded 1.18 g (97%) of the title compound 16a as an orange solid. $^1$H NMR (DMSO-d$_6$): δ 11.20 (s, 1H), 10.17 (s, 1H), 7.37 (s, 1H), 6.91 (s, 1H), 6.82 (s, 1H), 3.47 (s, 3H), 2.75 (t, J=7.2 Hz, 2H), 2.45 (t, J=7.2 Hz, 2H).

Compounds 16b–16g were synthesized from corresponding intermediates 14 and 15 using procedure described for 16a.

Methyl 3-(16-chloro-4,5,6,7,13-pentafluoro-12,15-dihydroxy-1-oxospiro[3-hydroisobenzofuran-3,9'-xanthene]-11-yl)propanoate (16b). $^1$H NMR (DMSO-d$_6$): δ 11.27 (s, 1H), 10.64 (s, 1H), 7.37 (s, 1H), 6.96 (s, 1H), 6.75 (s, 1H), 3.50 (s, 3H), 2.71 (t, J=7.2 Hz, 2H), 2.49 (t, J=7.2 Hz, 2H).

Methyl 3-(4,5,6,7,16-pentachloro-13-fluoro-12,15-dihydroxy-1-oxospiro[3-hydroisobenzofuran-3,9'-xanthene]11-yl)propanoate (16c). $^1$H NMR (DMSO-d$_6$): δ 11.23 (s, 1H), 10.55 (s, 1H), 7.35 (s, 1H), 6.96 (s, 1H), 6.66 (s, 1H), 3.46 (s, 3H), 2.71 (t, J=7.2 Hz, 2H), 2.43 (t, J=7.2 Hz, 2H).

Methyl 3-(13,16-dichloro-4,5,6,7-tetrafluoro-12,15-dihydroxy-1-oxospiro[3-hydroisobenzofuran-3,9'-xanthene]-11-yl)propanoate (16d). $^1$H NMR (DMSO-d$_6$): δ 11.28 (bs, 1H), 10.27 (bs, 1H), 7.38 (s, 1H), 6.95 (s, 1H), 6.91 (s, 1H), 3.50 (s, 3H), 2.76 (t, J=7.2 Hz, 2H), 2.49 (t, J=7.2 Hz, 2H).

Methyl 3-(16-chloro-4,5,6,7-tetrafluoro-12,15-dihydroxy-1-oxospiro[3-hydroisobenzofuran-3,9'-xanthene]-11-yl)propanoate (16e). $^1$H NMR (DMSO-d$_6$): δ 11.75 (s, 1H), 10.48 (s, 1H), 7.31 (s, 1H), 6.90 (s, 1H), 6.84 (s, 1H), 6.73 (s, 1H), 3.50 (s, 3H), 2.67 (t, J=7.5 Hz, 2H), 2.45 (t, J=7.5 Hz, 2H).

Methyl 3-(4,5,6,7-tetrafluoro-12,15-dihydroxy-1-oxospiro[3-hydroisobenzofuran-3,9'-xanthene]-11-yl)propanoate (16f). $^1$H NMR (DMSO-d$_6$): δ 10.42 (s, 1H), 10.27 (s, 1H), 6.98 (d, J=9 Hz, 1H), 6.86 (s, 1H), 6.72 (s, 1H), 6.69 (d, J=2 Hz, 1H), 6.57 (dd, J$_1$=9 Hz, J$_2$=2 Hz, 1H), 3.50 (s, 3H), 2.68 (t, J=7.5 Hz, 2H), 2.47 (t, J=7.5 Hz, 2H).

Methyl 3-(4,5,6,7,16-pentachloro-12,15-dihydroxy-1-oxo-13-phenylspiro[3-hydroisobenzofuran-3,9'-xanthene]-11-yl)propanoate (16g). $^1$H NMR (DMSO-d$_6$): δ 10.90 (s, 1H), 8.92 (s, 1H), 7.40–7.53 (m, 5H), 7.32 (s, 1H), 6.79 (s, 1H), 6.50 (s, 1H), 3.49 (s, 3H), 2.76 (t, J=7.4 Hz, 2H), 2.50 (t, J=7.4 Hz, 2H).

3-(4,5,6,7,13,16-Hexachloro-12,15-dihydroxy-1-oxospiro[3-hydroisobenzofuran-3,9'-xanthene]-11-yl)propanoic acid (17a). A suspension of 14a (20.0 g, 39 mmol) and 4-chlororesorcinol (15a) (20.0 g, 138 mmol) in 200 ml of trifluoroacetic acid was heated at 70° C. with stirring for 5 min to dissolve the solids. Methanesulfonic acid (10 ml) was added in one portion and the reaction was stirred at 70° C. for 2 h. The mixture was cooled and concentrated under vacuum. The oily residue was triturated with water (500 ml) and extracted with ethyl acetate (300 ml). The organic phase was washed with 5% sodium bicarbonate solution to extract the product; the aqueous phase was washed with ether and then acidified with hydrochloric acid to pH of 3. The fine precipitate was collected by filtration on sintered glass funnel and washed with water. Drying under vacuum (over P$_2$O$_5$) afforded 21.6 g (90%) of the title acid 17a as an orange solid. $^1$H NMR (DMSO-d$_6$): δ 11.20 (s, 1H), 10.16 (s, 1H), 7.37 (s, 1H), 6.91 (s, 1H), 6.82 (s, 1H), 2.75 (t, J=7.5 Hz, 2H), 2.45 (t, J=7.5 Hz, 2H).

3-(13,16-Dichloro-4,5,6,7-tetrafluoro-12,15-dihydroxy-1-oxospiro[3-hydroisobenzofuran-3,9'-xanthene]-11-yl)propanoic acid (17b). $^1$H NMR (DMSO-d$_6$): δ 11.95 (br s, 1H), 11.27 (br s, 1H), 10.21 (br s, 1H), 7.37 (s, 1H), 7.21 (s, 1H), 6.93 (s, 1H), 2.70 (t, J=7.5 Hz, 2H), 2.35 (t, J=7.5 Hz, 2H).

3-(12,15-Dihydroxy-1-oxospiro[3-hydroisobenzofuran-3,9'-xanthene]-11-yl)propanoic acid (17c). $^1$H NMR (DMSO-d$_6$): δ 10.3 (br s, 1H), 10.2 (br s, 1H), 8.00 (d, J=7.2 Hz, 1H), 7.75 (m, 2H), 7.23 (d, J=7.2 Hz, 1H), 6.71 (s, 1H), 6.66 (s, 1H), 6.51 (m, 2H), 6.44 (s, 1H), 2.57 (t, J=7.5 Hz, 2H), 2.30 (t, J=7.5 Hz, 2H).

3-(4,7,13,16-Tetrachloro-12,15-dihydroxy-14-methyl-1-oxospiro[3-hydroisobenzofuran-3,9'-xanthene]-11-yl)propanoic acid (17d). $^1$H NMR (DMSO-d$_6$): δ 12.02 (br s, 1H), 10.09 (s, 1H), 9.96 (s, 1H), 7.81 (s, 2H), 6.97 (s, 1H), 6.75 (s, 1H), 2.69 (m, 2H), 238 (s, 3H), 2.35 (t, J=7.5 Hz, 2H).

3-(4,7,13,16-Tetrachloro-12,15-dihydroxy-1-oxospiro[3-hydroisobenzofuran-3,9'-xanthene]-11-yl)propanoic acid (17e). $^1$H NMR (DMSO-d$_6$): δ 12.07 (br s, 1H), 11.14 (br s, 1H), 10.02 (br s, 1H), 7.79 (s, 2H), 7.14 (s, 1H), 6.91 (s, 1H), 6.75 (s, 1H), 2.70 (m, 2H), 2.34 (t, J=7.5 Hz, 2H).

3-(4,7,13-Trichloro-12,15-dihydroxy-1-oxospiro[3-hydroisobenzofuran-3,9'-xanthene]-11-yl)propanoic acid (17f). $^1$H NMR (DMSO-d$_6$): δ 12.08 (br s, 1H), 10.24 (br s, 1H), 10.02 (br s, 1H), 7.81 (s, 2H), 6.80 (s, 1H), 6.77 (d, J=9 Hz, 1H), 6.70 (d, J=2 Hz, 1H), 6.59 (dd, J$_1$=9 Hz, J$_2$=2 Hz, 1H), 2.71 (m, 2H), 2.35 (t, J=7.5 Hz, 2H).

3-(13,16-Dichloro-4,7-difluoro-12,15-dihydroxy-1-oxospiro[3-hydroisobenzofuran-3,9'-xanthene]-11-yl)propanoic acid (17g). $^1$H NMR (DMSO-d$_6$): δ 12.05 (br s, 1H), 11.19 (s, 1H), 10.11 (s, 1H), 7.64 (m, 2H), 7.24 (s, 1H), 6.93 (s, 1H), 6.86 (s, 1H), 2.70 (m, 2H), 3.36 (t, J=7.5 Hz, 2H).

3-(5,6,13,16-Tetrachloro-12,15-dihydroxy-14-methyl-1-oxospiro[3-hydroisobenzofuran-3,9'-xanthene]-11-yl)propanoic acid (17h). $^1$H NMR (DMSO-d$_6$): δ 12.08 (br s, 1H), 10.05 (br s, 1H), 9.98 (br s, 1H), 8.27 (s, 1H), 7.81 (s, 1H), 6.81 (s, 1H), 6.66 (s, 1H), 2.66 (m, 2H), 2.39 (s, 3H), 2.34 (m, 2H).

3-(5,6,13,16-Tetrachloro-12,15-dihydroxy-1-oxospiro[3-hydroisobenzofuran-3,9'-xanthene]-11-yl)propanoic acid (17i). $^1$H NMR (DMSO-d$_6$): δ 12.06 (br s, 1H), 11.14 (br s, 1H), 10.08 (br s, 1H), 8.26 (s, 1H), 7.81 (s, 1H), 6.97 (s, 1H), 6.91 (s, 1H), 6.65 (s, 1H), 2.67 (m, 2H), 2.34(m, 2H).

3-(5,6,13-Trichloro-12,15-dihydroxy-1-oxospiro[3-hydroisobenzofuran-3,9'-xanthene]-11-yl)propanoic acid (17j). $^1$HNMR (DMSO-d$_6$): δ12.07 (br s, 1H), 11.14 (br s, 1H), 10.05 (br s, 1H), 8.29 (s, 1H), 7.80 (s, 1H), 6.67 (m, 4H), 2.66 (m, 2H), 2.34 (m, 2H).

8,12,22,23,24,25-Hexachloro-9-hydroxyspiro[3,4-dihydro-2H-pyrano[3,2-b]xanthene-6,3'-3-hydroisobenzofuran]-2,19-dione (18a). Acid 17a (7.84 g, 12.9 mmol) was dissolved in 100 ml of anhydrous CH$_2$Cl$_2$ in the presence of 10 ml of triethylamine. PFP-TFA (9 ml, 52 mmol) was added with stirring and the reaction was allowed to proceed for 30 min. TLC analysis (9:1, CH$_2$Cl$_2$:MeOH) showed one major product with R$_f$~0.8. The solvent was evaporated to give a tan oil. Trituration with cold methanol (100 ml) produced a suspension of the desired lactone 18a. After being stirred for ~5 min the solid was collected by filtration and washed with cold methanol. Drying under vacuum afforded 6.8 g (88%) of 18a as an off-white solid. $^1$H NMR (DMSO-d$_6$): δ 11.27 (s, 1H), 7.43 (s, 1H), 7.20 (s, 1H), 6.95 (s, 1H), 2.92 (t, J=7.2 Hz, 2H), 2.82 (t, J=7.2 Hz, 2H).

8,12,22,23,24,25-Hexachloro-9-hydroxyspiro[3,4-dihydro-2H-pyrano[3,2-b]xanthene-6,3'-3-hydroisobenzofuran]-2,19-dione (18b). $^1$H NMR (DMSO-d$_6$): δ 11.36 (s, 1H), 7.44 (s, 1H), 7.24 (s, 1H), 6.97 (s, 1H), 2.95 (m, 2H), 2.82 (m, 2H).

9-Hydroxyspiro[3,4-dihydro-2H-pyrano[3,2-b]xanthene-6,3'-3-hydroisobenzofuran]-2,19-dione (18c). $^1$H NMR (DMSO-d$_6$): δ 10.21 (br s, 1H), 8.00 (d, J=7.2 Hz, 1H), 7.75 (m, 2H), 7.28 (d, J=7.2 Hz, 1H), 7.12 (s, 1H), 6.76 (s, 1H), 6.70 (s, 1H), 6.57 (s, 2H), 2.81 (t, J=7.5 Hz, 2H), 2.75 (m, 2H).

8,12,23,24-Tetrachloro-9-hydroxy-10-methylspiro[3,4-dihydro-2H-pyrano[3,2-b]xanthene-6,3'-3-hydroisobenzofuran]-2,19-dione (18d). $^1$H NMR (DMSO-d$_6$): δ 10.05 (s, 1H), 8.31 (s, 1H), 7.89 (s, 1H), 6.94 (s, 1H), 6.89 (s, 1H), 2.94 (t, J=7.5 Hz, 2H), 2.82 (t, J=7.5 Hz, 2H), 2.39 (s, 3H).

Methyl 3-(4,5,6,7,17-pentachloro-14,18-dihydroxy-1-oxospiro[3-hydroisobenzofuran-3,12'-benzo[a]xanthene]-19-yl)propanoate (19a). 1,3-Dihydroxynaphthalene (0.57 g, 3.56 mmol) and 14a (1.0 g, 1.93 mmol) were suspended in 10 ml of methanesulfonic acid. The suspension was stirred at 70° C. under argon for 1 h and cooled. A mixture of ice and water (50 g) was added to precipitate the product. Ethyl acetate (50 ml) was added to extract the precipitate. The product from organic layer was extracted with sodium bicarbonate solution. The aqueous phase was washed with ether to remove excess 4-chlororesorcinol and acidified with concentrated hydrochloric acid. The precipitated material, pure product 16a, was taken up in ethyl acetate and dried over Na$_2$SO$_4$. Concentration of the solution and drying under vacuum afforded 1.01 g (82%) of the title compound 19a as an orange solid. $^1$H NMR (DMSO-d$_6$): δ11.35 (s, 1H), 10.20 (s, 1H), 8.23 (m, 1H), 7.40 (m, 2H), 6.96 (m, 1H), 6.87 (s, 1H), 6.64 (s, 1H), 3.46 (s, 3H), 2.77 (t, J=7.2 Hz, 2H), 2.47 (t, J=7.2 Hz, 2H).

Esters 19b–19i were prepared by the procedure described for compound 19a.

Methyl 3-(4,5,6,7,17-pentafluoro-14,18-dihydroxy-1-oxospiro[3-hydroisobenzofuran-3,12'-benzo[a]xanthene]-19-yl)propanoate (19b). $^1$H NMR (DMSO-d$_6$): δ11.8 (br s, 1H), 10.8 (br s, 1H), 8.24 (m, 1H), 7.46 (m, 2H), 7.12 (m, 1H), 6.80 (s, 1H), 6.63 (s, 1H), 3.52 (s, 3H), 2.77 (t, J=7.2 Hz, 2H), 2.47 (t, J=7.2 Hz, 2H).

Methyl 3-(4,5,6,7-tetrachloro-17-fluoro-14,18-dihydroxy-1-oxospiro[3-hydroisobenzofuran-3,12'-benzo[a]xanthene]-19-yl)propanoate (19c). $^1$H NMR (DMSO-d$_6$): δ11.4 (br s, 1H), 10.6 (br s, 1H), 8.22 (m, 1H), 7.40 (m, 2H), 6.96 (m, 1H), 6.89 (s, 1H), 6.48 (s, 1H), 3.46 (s, 3H), 2.74 (t, J=7.2 Hz, 2H), 2.44 (t, J=7.2 Hz, 2H).

Methyl 3-(17-chloro-4,5,6,7-tetrafluoro-14,18-dihydroxy-1-oxospiro[3-hydroisobenzofuran-3,12'-benzo[a]xanthene]-19-yl)propanoate (19d). $^1$H NMR (DMSO-d$_6$): δ 12.00 (bs, 1H), 11.39 (bs, 1H), 10.24 (bs, 1H), 8.25 (m, 1H), 7.46 (bm, 2H), 7.10 (bm, 1H), 6.85 (bm, 1H), 6.78 (bs, 1H), 3.52 (s, 3H), 2.80 (t, J=7.6 Hz, 2H), 2.49 (t, J=7.6 Hz, 2H).

Methyl 3-(5,6,17-trichloro-14,18-dihydroxy-1-oxospiro[3-hydroisobenzofuran-3,12'-benzo[a]xanthene]-19-yl)propanoate (19e). $^1$H NMR (DMSO-d$_6$): δ 8.46 (s, 1H), 8.23 (d, J=8.5 Hz, 1H), 7.77 (s, 1H), 7.31–7.42 (m, 2H), 6.90 (d, J=9.0 Hz, 1H), 6.78 (bs, 1H), 6.47 (s, 1H), 3.45 (s, 3H), 2.73 (t, J=7.2 Hz, 2H), 2.44 (t, J=7.5 Hz, 2H).

Methyl 3-(5,6-dichloro-17-fluoro-14,18-dihydroxy-1-oxospiro[3-hydroisobenzofuran-3,12'-benzo[a]xanthene]-19-yl)propanoate (19f). $^1$H NMR (DMSO-d$_6$): δ 11.8 (br s, 1H), 10.7 (br s, 1H), 8.46 (s, 1H), 8.23 (d, J=8.5 Hz, 1H), 7.75 (s, 1H), 7.31–7.42 (m, 2H), 6.90 (d, J=9.0 Hz, 1H), 6.81 (bs, 1H), 6.30 (s, 1H), 3.45 (s, 3H), 2.70 (t, J=7.2 Hz, 2H), 2.44 (t, J=7.5 Hz, 2H).

Methyl 3-(4,5,6,7-tetrafluoro-14,18-dihydroxy-1-oxospiro[3-hydroisobenzofuran-3,12'-benzo[a]xanthene]-19-yl)propanoate (19g). $^1$H NMR (DMSO-d$_6$): δ 11.3 (br s, 1H), 10.5 (br s, 1H), 8.22 (d, J=8.5 Hz, 1H), 7.44 (m, 2H), 7.08 (m, 1H), 6.9–6.7 (m, 3H), 3.49 (s, 3H), 2.72 (m, 2H), 2.49 (m, 2H).

Methyl 3-(17-chloro-14,18-dihydroxy-1-oxospiro[3-hydroisobenzofuran-3,12'-benzo[a]xanthene]-19-yl)propanoate (19h). $^1$H NMR (DMSO-d$_6$): δ 11.3 (br s, 1H), 10.1 (br s, 1H), 8.19 (m, 2H), 7.70 (m, 3H), 7.30 (m, 1H), 7.25 (m, 2H), 6.85 (m, 2H), 6.30 (s, 1H), 3.40 (s, 3H), 2.70 (m, 2H), 2.38 (m, 2H).

Methyl 3-(17-fluoro-14,18-dihydroxy-1-oxospiro[3-hydroisobenzofuran-3,12'-benzo[a]xanthene]-19-yl)propanoate (19i). $^1$H NMR (DMSO-d$_6$): δ 11.23 (s, 1H), 10.44 (s, 1H), 8.17 (m, 2H), 7.71 (m, 3H), 7.30 (m, 1H), 7.21 (m, 2H), 6.86 (m, 2H), 6.15 (s, 1H), 3.41 (s, 3H), 2.66 (m, 2H), 2.38 (m, 2H).

3-(4,5,6,7,17-Pentachloro-14,18-dihydroxy-1-oxospiro[3-hydroisobenzofuran-3,12'-benzo[a]xanthene]-19-yl)propanoic acid (20a). Ester 19a (1.32 g, 2.06 mmol) was dissolved in 13 ml of 1N NaOH using sonication. After being stirred at room temperature for 1 h, the solution was acidified with 1N HCl to pH 3. The resultant precipitate was collected by filtration and washed with water. Drying under vacuum over $P_2O_5$ afforded 1.1 g (85%) of acid 20a as an orange solid. $^1$H NMR (DMSO-$d_6$): δ 12.1 (br s, 1H), 11.34 (br s, 1H), 10.15 (br s, 1H), 8.22 (m, 1H), 7.40 (m, 2H), 6.95 (m, 1H), 6.87 (s, 1H), 6.74 (s, 1H), 2.74 (m, 2H), 2.38 (m, 2H).

3-(17-Chloro-14,18-dihydroxy-1-oxospiro[3-hydroisobenzofuran-3,12'-benzo[a]xanthene]-19-yl)propanoic acid (20b). Acid 20b was prepared analogously to compound 20a. $^1$H NMR (DMSO-$d_6$): δ 12.1 (br s, 1H), 11.23 (s, 1H), 10.04 (s, 1H), 8.18 (m, 2H), 7.08 (m, 2H), 7.29 (m, 1H), 7.21 (m, 2H), 6.82 (m, 2H), 6.37 (s, 1H), 2.66 (m, 2H), 2.29 (m, 2H).

4,5,6,7,17-Pentachloro-14-hydroxyspiro[3-hydroisobenzofuran-3,14'-benzo[f]chromano[7,6-b]4H-chromene]-1,19-dione (21a). Lactone 21a was prepared by the procedure described for compound 18a. $^1$H NMR (DMSO-$d_6$): δ 11.47 (br s, 1H), 8.24 (m, 1H), 7.42 (m, 2H), 7.08 (s, 1H), 6.95 (m, 1H), 9.92 (s, 1H), 2.99 (m, 2H), 2.83 (m, 2H).

17-Chloro-14-hydroxyspiro[3-hydroisobenzofuran-3,14'-benzo[f]chromano[7,6-b]4H-chromene]-1,19-dione (21b). Lactone 21b was prepared by the procedure described for compound 18a. $^1$H NMR (DMSO-$d_6$): δ 11.39 (br s, 1H), 8.19 (m, 2H), 7.74 (m, 2H), 7.4–7.2 (m, 3H), 6.95 (s, 1H), 6.55 (d, J=8.5 Hz, 1H), 6.66 (s, 1H), 3.05 (m, 2H), 2.79 (m, 2H).

3-(4,5,6,7,20-Pentachloro-12,19-dihydroxy-1-oxospiro [3-hydroisobenzofuran-3,7'-benzo[h]xanthene]-18-yl)propanoic acid (22). Compound 22 was prepared from 18a and 1,6-dihydroxynaphtalene in 75% yield using the general method described for 19a. $^1$H NMR (DMSO-$d_6$): δ 12.05 (br s, 1H), 10.24 (br s, 1H), 8.39 (d, 9 Hz, 1H), 7.46 (d, J=9 Hz, 1H), 7.31 (d, J=9 Hz, 1H), 7.21 (s, 1H), 7.03 (s, 1H), 6.99 (d, J=9 Hz, 1H), 2.74 (m, 2H), 2.40 (t, J=7.5 Hz, 2H).

4,5,6,7,22-Pentachloro-12-hydroxyspiro[3-hydroisobenzofuran-3,7'-benzo[h]chromano[7,6-b]4H-chromene]-1,20-dione (23). $^1$H NMR (DMSO-$d_6$): δ 10.3 (br s, 1H), 8.39 (d, 9 Hz, 1H), 7.49 (d, J=9 Hz, 1H), 7.33 (m, 2H), 7.22 (s, 1H), 7.05 (d, J=9 Hz, 1H), 3.05 (m, 2H), 2.79 (m, 2H).

Derivatization of amino-tailed oligonucleotides using chromanone dye derivatives. To a solution of triethylammonium salt of 5'-aminohexyl-octathymidylate (0.2 μmol) in 30 μL of DMSO was added 1 μmol of one of the lactone 8, 12, 18 or 21 followed by 0.5 μL of triethylamine. The mixture was sonicated for a few seconds to dissolve the reagents, and the reaction was allowed to proceed for 3–6 h. Progress of the reaction was monitored by reverse-phase HPLC, an aliquot of 0.5 μL was typically taken for the analysis. To precipitate the product (in some cases together with the derivatizing agent) 1 mL of 2% solution of $LiClO_4$ was added, the precipitate was collected by centrifugation, washed with acetone and dried. The crude products were purified by denaturing gel-electrophoresis followed by reverse-phase HPLC.

(5S,3R)-5-{[Bis(4-methoxyphenyl)phenylmethoxy] methyl}pyrrolidin-3-ol (25). To a stirred solution of Fmoc-DMT-prolinol (24) (Normand, H et al Tetrahedron Lett., 1994, v. 35; 51; 9509–9512.) (31.39 g, 48.9 mmol) in anhydrous $CH_2Cl_2$ (250 ml) was added 11.5 ml (76.7 mmol) of DBU. After being stirred at temperature for 0.5 h reaction mixture was concentrated and chromatographed on silica eluting first with $Et_3N$-MeOH—$CH_2Cl_2$ (2:3:95) and then with $Et_3N$-MeOH—$CH_2Cl_2$ (2:10:88) mixture. Concentration of the pure product fraction and drying under vacuum afforded 15.07 g (73%) of amine 25 as white foam.

Mixture of 8-[3-((5S,3R)-5-{[bis(4-methoxyphenyl)phenylmethoxy]methyl}-3-hydroxypyrrolidinyl)-3-oxopropyl ]-7-oxophenoxazin-3-yl 2,2-dimethylpropanoate and 2-[3-((5S,3R)-5-{[bis(4-methoxyphenyl)phenylmethoxy]methyl}-3-hydroxypyrrolidinyl)-3-oxopropyl]-7-oxophenoxazin-3-yl 2,2-dimethylpropanoate (27). Lactone 12a (7.5 g, 28.07 mmol) was added in one portion to a solution of amine 25 (14.13 g, 433.68 mmol) in 150 ml of anhydrous DMF. After being stirred at room temperature for 0.5 h diisopropylethylamine (10.88 g, 14.67 ml, 84.2 mmol) was added followed by trimethylacetic anhydride (12.55 g, 16.37 ml, 67.36 mmol) and the reaction was stirred was stirred for another 1 h. The material obtained after evaporation of the solvent was chromatographed on silica eluting first with EtOAc:$Et_3N$ (98:2) and then with a 0 to 5% gradient of MeOH in EtOAc. The fractions containing pure product were collected and concentrated to give 21.7 g of an amorphous solid. To remove residual methanol the solid was dissolved in EtOAc (60 ml) and precipitated by slowly adding to 600 ml of stirred hexane. The precipitate was filtered off and washed with hexane. Drying under vacuum afforded 17.9 g (83%) of 27 as a yellow-orange solid (9:1 mixture of isomers).

A mixture of 8-[3-((2S,4R)-2-{[1,1-bis(4-methoxyphenyl)-2-ethylidenebut-3-enyloxy]methyl}-4-{(2-cyanoethoxy)[ethyl(methylethyl)amino]phosphinooxy}-pyrrolidinyl)-3-oxopropyl] -7-oxophenoxazin-3-yl 2,2-dimethylpropanoate and 2-[3-((2S,4R)-2-{[bis(4-methoxyphenyl)phenylmethoxy] methyl}-4-{[bis(methylethyl)amino](2-cyanoethoxy) phosphinooxy}pyrrolidinyl)-3-oxopropyl]-7-oxophenoxazin-3-yl 2,2-dimethylpropanoate (28). To a solution of 27 (10.5 g, 13.62 mmol) in anhydrous $CH_2Cl_2$ (200 ml) was added with stirring diisopropylethylamine (6.99 ml, 5.187 g, 40.13 mmol) followed by 2-cyanoethyl-N,N-diisopropylchlorophosphoramidite (4.22 g, 3.98 ml, 17.84 mmol). After being stirred at room temperature for 2 h, methanol (0.2 ml, 4.9 mmol) was added to quench excess chlorophosphoramidite. The reaction mixture was concentrated and loaded on a silica gel column which had been pre-washed with EtOAc:Hexane:$Et_3N$ (60:40:5) mixture (1 L) and then equilibrated with EtOAc:Hexane (3:2) mixture. The product was eluted a 10–60% gradient of ethyl acetate in hexane. Concentration of the pure product fractions gave the desired phosphoramidite as an orange foam. To obtain product as a solid, the foam was dissolved in anhydrous ether (20 ml) and precipitated by dropwise addition to vigorously stirred hexane (700 ml) under argon. The precipitate was filtered off and dried in vacuo to afford (8.9 g) of 28 (67%) as an amorphous solid. $^{31}$P NMR (DMSO-$d_6$): δ 143.64, 143.04.

Methyl 3-(2,6-dihydroxyphenyl)propionate (30) was prepared by treating methanolic solution of 3-(2,6-dihydroxyphenyl)propionic acid (29) (Mitoshi K. et al. Syn. Lett., 12; 1997; 1472–1474) with anhydrous HCl gas. $^1$H NMR (d6-DMSO) δ: 9.16 (s, 2H), 6.76 (t, J=8 Hz, 1H), 6.26 (d, J=8 Hz, 2H), 3.59 (s, 3H), 2.75 (t, J=7.5 Hz, 2H), 2.34 (t, J=7.5 Hz, 2H).

Methyl 3-(3-chloro-2,6-dihydroxyphenyl)propionate (31). To a solution of 30 (5.0 g, 25.5 mmol) in 50 ml of methanol was added 3.4 g (25.5 mmol) of N-chlorosuccinimide. The reaction was stirred overnight at room temperature and concentrated. The residue was suspended in a mixture of hexane and ethyl acetate and the precipitated succinimide was removed by filtration. Crude product obtained after evaporation of the solvent was chromatographed on silica eluting with 4:1 hexane-ethyl acetate. Concentration of the pure product fractions afforded 4.4 g of the title compound as colorless oil that slowly crystallized during prolonged drying under vacuum. $^1$H NMR (d6-DMSO) δ: 9.52 (s, 1H), 8.95 (s, 1H), 6.97 (d, J=8.5 Hz, 1H), 6.35 (d, J=8.5 Hz, 1H), 3.59 (s, 3H), 2.81 (t, J=7.5 Hz, 2H), 2.34 (t, J=7.5 Hz, 2H).

4,5-Dichloro-2-({5-chloro-2,4-dihydroxy-3-[2-(methoxycarbonyl)ethyl]phenyl}carbonyl)benzoic acid (35). Benzophenone 35 was synthesized according to the general procedure described for compound 14a in a similar synthetic yield. $^1$H NMR (d6-DMSO) δ: 12.25 (s, 1H), 10.69 (br s, 1H), 8.14 (s, 1H), 7.90 (s, 1H), 7.06 (s, 1H), 3.61 (s, 3H), 2.93 (t, J=7.5 Hz, 2H), 2.48 (t, J=7.5 Hz, 2H).

3-(5,6,11,16-Tetrachloro-12,15-dihydroxy-14-methyl-1-oxospiro[3-hydroisobenzofuran-3,9'-xanthene]-13-yl)propanoic acid (37). To a suspension of 35 (200 mg, 0.45 mmol) and 2-methyl-4-chlororesorcinol (110 mg, 0.69 mmol) in 5 ml of trifluoroacetic acid was added 0.7 ml of methanesulfonic acid. The reaction was stirred at room temperature for 6 h to give a dark-purple solution. The solvent was removed on a rotary evaporator at room temperature and water was added to precipitate the colorless intermediate 36. The solid was collected by filtration, washed with water and re-suspended in 15 ml of water. Sodium hydroxide solution (5 ml, 1N) was added and the resultant solution was kept at room temperature for 20 min and acidified with 1N HCl to pH of 2. The precipitated product was filtered off and washed with water. Drying under vacuum afforded 202 mg (81%) of the desired dye as an orange solid. $^1$H NMR (d6-DMSO) δ: 12.25 (s, 1H), 9.96 (br s, 1H), 8.14 (s, 1H), 7.82 (s, 1H), 7.05 (s, 1H), 6.82 (s, 1H), 3.14 (m, 2H), 2.87 (m, 2H), 2.35 (s, 3H).

5,9,23,24-Tetrachloro-10-hydroxy-11-methylspiro[1,2-dihydro-2H-pyrano[2,3-c]xanthene-7,3'-3-hydroisobenzofuran]-3,19-dione (38). Lactone 38 was synthesized according to the general method described for compound 18a. $^1$H NMR (d6-DMSO) δ: 10.03 (s, 1H), 8.27 (s, 1H), 7.85 (s, 1H), 7.13 (s, 1H), 6.85 (s, 1H), 3.28 (m, 2H), 2.39 (m, 2H), 2.36 (s, 3H).

11-[2-(N-{6-[Bis(4-methoxyphenyl)phenylmethoxy]hexyl}carbamoyl)ethyl]-15-(2,2-dimethylpropanoyloxy)-5,6,13,16-tetrachloro-14-methyl-1-oxospiro[3-hydroisobenzofuran-3,9'-xanthene]-12-yl 2,2-dimethylpropanoate (41). A solution of 18d (2.67 g, 4.9 mmol), 5-aminohexanol (0.7 g, 5.4 mmol) and triethylamine (5 ml) in 20 ml of anhydrous DMF was kept at room temperature for 5 h. TLC analysis (1:9, MeOH:CH$_2$Cl$_2$) showed complete conversion of 18d into a new, lower mobility product (compound 39). DMTr-chloride (6.0 g) was added in several portions over several hours until all the intermediate 39 was converted into compound 40 (analysis by TLC).

N-Methylimidazole (5 ml) and trimethylacetic anhydride (6 ml) were added. The reaction was heated at 50° C. with stirring for 7 h. The solvent was evaporated under vacuum and the resultant oil was partitioned between water (200 ml) and ethyl acetate (150 ml). The organic phase was washed with brine and dried over Na$_2$SO$_4$. The material obtained after solvent concentration was chromatographed on silica eluting with 3:1 hexane-ethyl acetate. Concentration of the product containing fractions afforded 3.4 g (61%) of 41 as a pale yellow, amorphous solid. $^1$H NMR (DMSO-d$_6$): δ 8.32 (s, 1H), 8.0 (br s, 1H), 7.66 (t, J=5 Hz, 1H), 7.4–7.1 (m, 10H), 6.90)s, 1H), 6.88 (s, 2H), 6.87 (s, 2H), 3.72 (s, 6H), 2.9 (m, 4H), 2.58 (m, 2H), 2.30 (s, 3H), 1.49 (m), 1.38 (s, 18H), 1.27 (m), 1.16 (m).

15-(2,2-Dimethylpropanoyloxy)-5,6,13,16-tetrachloro-11-{2-[N-(6-hydroxyhexyl)carbamoyl]ethyl}-14-methyl-1-oxospiro[3-hydroisobenzofuran-3,9'-xanthene]-12-yl 2,2-dimethylpropanoate (42). To a solution of 41 (3.4 g, 3 mmol) in 50 ml of 10% methanol in dichloromethane was added 0.15 ml of trifluoroacetic acid. After being stirred for 1 h, the solution was treated with triethylamine (0.15 ml) to neutralize the acid. The reaction mixture was chromatographed on a silica gel column eluting with ethyl acetate. Concentration of the pure product fraction afforded 2.0 g (73%) of the title compound (42) as an off-white, amorphous solid. $^1$H NMR (DMSO-d$_6$): δ 7.75 (s, 1H), 7.73 (br t, 1H), 7.69 (s, 1H), 7.19 (s, 1H), 3.34 (t, J=6.5 Hz, 2H), 2.89 (m, 2H), 2.59 (m, 2H), 2.20 (m, 2H), 1.38 (s, 9H), 1.34 (s, 9H), 1.4–1.1 (m overlapping with two (CH$_3$)$_3$ signals, 6H).

11-{2-[N-(6-{[Bis(methylethyl)amino](2-cyanoethoxy)phosphinooxy}hexyl)carbamoyl]ethyl}-15-(2,2-dimethylpropanoyloxy)-5,6,13,16-tetrachloro-14-methyl-1-oxospiro[3-hydroisobenzofuran-3,9'-xanthene]-12-yl 2,2-dimethylpropanoate (43). To a stirred solution of 42 (1.2 g, 1.45 mmol) in 10 ml of anhydrous CH$_2$Cl$_2$ was added diisopropylethylamine (0.5 ml) followed by 0.35 ml (1.5 mmol) of 2-cyanoethyl-N,N-diisipropyl chlorophosphoramidite. After being stirred for 1 h, the reaction was quenched with methanol (0.05 ml) and diluted with ethyl acetate (50 ml). The solution was washed with saturated sodium bicarbonate, brine and dried over Na$_2$SO$_4$. The crude material obtained after evaporation of the solvent was purified by precipitation in anhydrous hexane from small amount of ether. The precipitated solid was collected by filtration and washed with hexane. Drying under vacuum afforded 1.1 g (74%) of 43 as a colorless, amorphous solid. $^1$H NMR (DMSO-d$_6$): δ.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method for preparing a fluorescent dye-labeled phosphoramidite reagent, said method comprising:
   (a) contacting a fluorescent dye-fused lactone derivative with a linking group component to form an intermediate fluorescent dye-labeled linking group; and
   (b) contacting said intermediate fluorescent dye-labeled linking group with a phosphoramidite moiety under conditions sufficient to covalently attach the phosphoramidite moiety to said fluorescent dye-labeled linking group and form said fluorescent dye-labeled phosphoramidite reagent.

2. A method in accordance with claim 1, wherein said fluorescent dye-fused lactone derivative has a formula selected from the group consisting of:

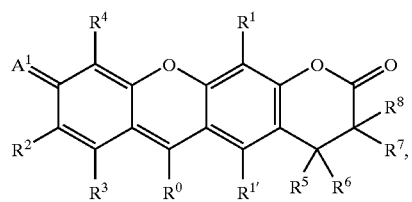

I

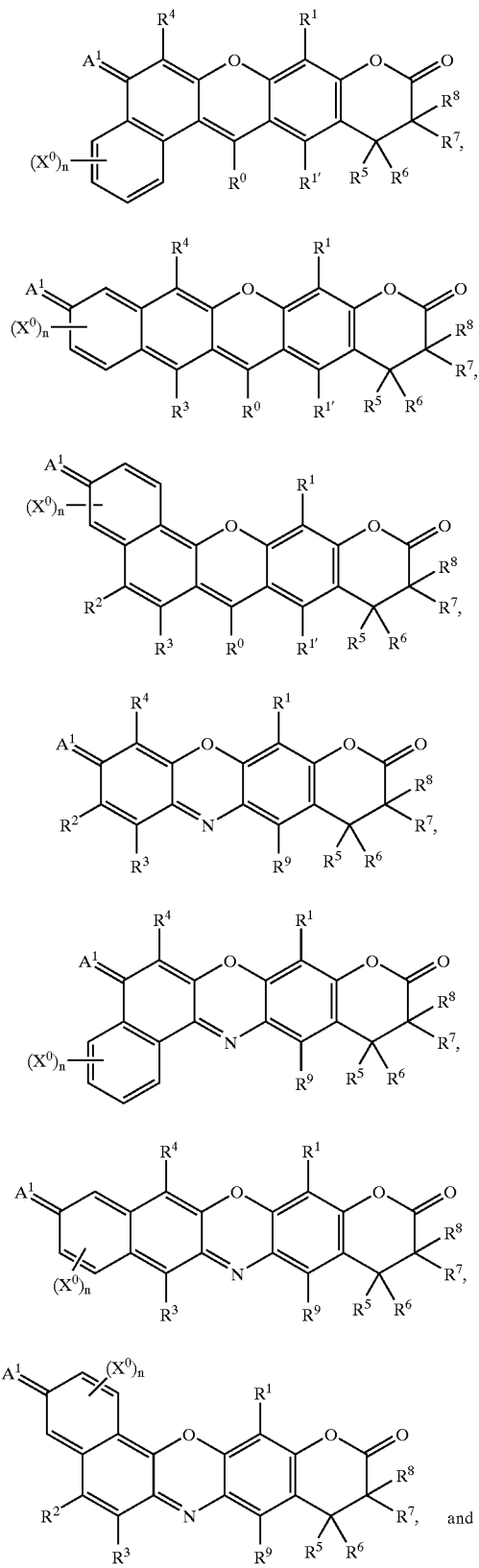

wherein
A¹ represents O or N—Z in which Z is H or $(C_1-C_8)$alkyl, or is optionally combined with $R^2$ or $R^4$ to form a 5- or 6-membered ring or is combined with each of $R^2$ and $R^4$ to form two fused 6-membered rings; or is optionally combined with and adjacent $X^0$ to form a 5- or 6-membered ring or is combined with two adjacent $X^0$ to form two fused 6-membered rings;

$R^{1'}$, $R^1$, $R^2$, $R^3$ and $R^4$ are each independently selected from H, halogen, cyano, $CF_3$, $(C_1-C_8)$alkyl, $(C_1-C_8)$alkylthio, $(C_1-C_8)$alkoxy, aryl and heteroaryl;

$R^5$, $R^6$, $R^7$, $R^8$ and $R^9$ are each independently selected from H, $(C_1-C_8)$alkyl, aryl heteroaryl, aryl$(C_1-C_4)$alkyl and heteroaryl$(C_1-C_4)$alkyl; wherein the alkyl portions of any of $X^0$, $R^{1'}$ and $R^1$ through $R^9$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and the aryl portions of any of $X^0$, $R^{1'}$ and $R^1$ through $R^9$ are optionally substituted with from one to four substituents selected from the group consisting of halogen, cyano, carboxy, sulfo, hydroxy, amino, mono- or di$(C_1-C_6)$alkylamino, $(C_1-C_6)$alkyl, $(C_1-C_6)$alkylthio and $(C_1-C_6)$alkoxy;

the subscript n is an integer of from 0 to 4:

each $X^0$ is a member independently selected from the group consisting of H, halogen, cyano, $CF_3$, $(C_1-C_8)$alkyl, $(C_1-C_8)$alkoxy, $(C_1-C_8)$alkylthio, $(C_2-C_8)$alkenyl, $(C_2-C_8)$alkynyl aryl, heteroaryl, $SO_3H$ and $CO_2H$;

$R^0$ is a member selected from the group consisting of halogen, cyano, $CF_3$, $(C_2-C_8)$alkyl, $(C_2-C_8)$alkenyl, $(C_2-C_8)$alkynyl, substituted or unsubstituted heteroaryl or aryl having the formula:

wherein $X^1$, $X^2$, $X^3$, $X^4$ and $X^5$ are each independently selected from the group consisting of H, halogen, cyano, $CF_3$, $(C_1-C_8)$alkyl, $(C_1-C_8)$alkoxy, $(C_1-C_8)$alkylthio, $(C_2-C_8)$alkenyl, $(C_2-C_8)$alkynyl, $SO_3H$ and $CO_2H$, and optionally, any two adjacent $X^1$ through $X^5$ are combined to form an aromatic or heteroaromatic ring.

3. A method in accordance with claim 1, wherein fluorescent dye-fused lactone derivative has a formula selected from the group consisting of:

Ia
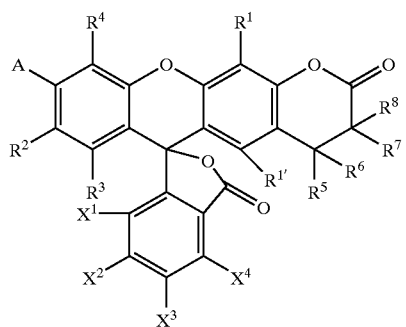

Ib
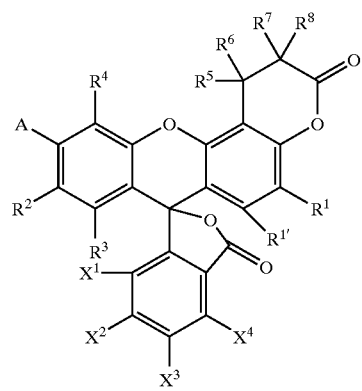

IIa
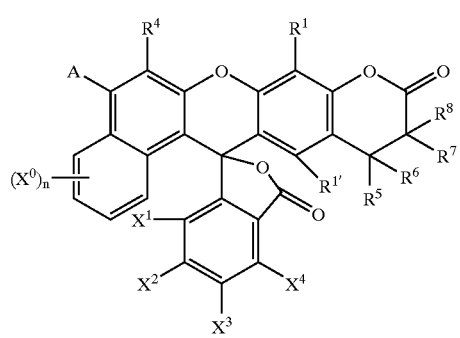

IIb
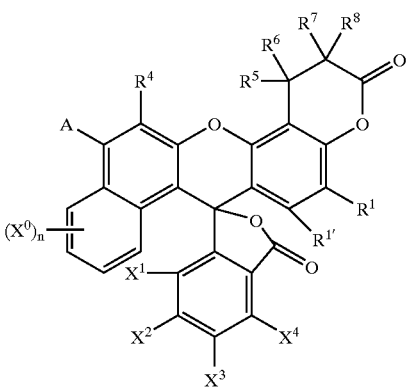

IIIa
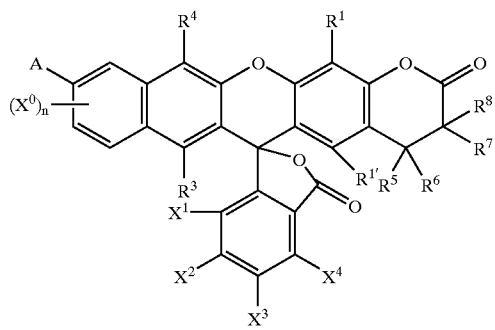

IIIb
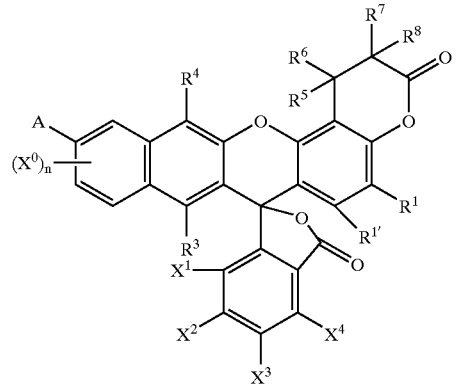

IVa
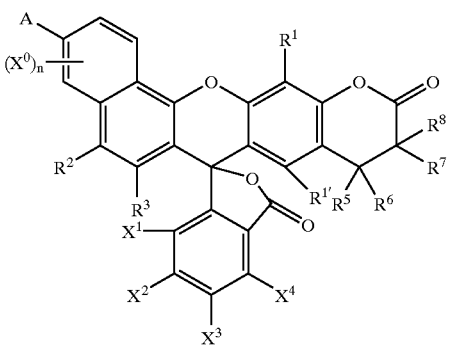

and

-continued

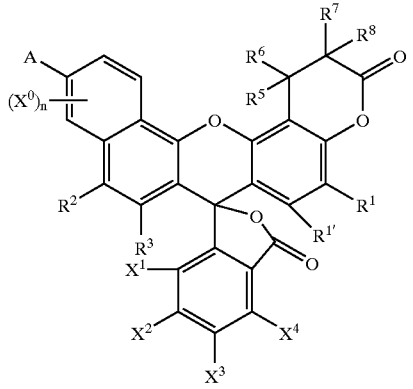

IVb wherein
- A is hydroxy, amino, protected hydroxy, or protected amino;
- the subscript n is an integer of from 0 to 4;
- each $X^0$ is a member independently selected from the group consisting of H, halogen, cyano, $CF_3$, $(C_1-C_8)$alkyl, $(C_1-C_8)$alkoxy, $(C_1-C_8)$alkylthio, $(C_2-C_8)$alkenyl, $(C_2-C_8)$alkynyl, aryl, heteroaryl, $SO_3H$ and $CO_2H$;
- $R^{1'}$, $R^1$, $R^2$, $R^3$ and $R^4$ are each independently selected from H, halogen, cyano, $CF_3$, $(C_1-C_8)$alkyl, $(C_1-C_8)$alkylthio and $(C_1-C_8)$alkoxy;
- $R^5$, $R^6$, $R^7$ and $R^8$ are each independently selected from H, $(C_1-C_8)$alkyl, aryl and aryl$(C_1-C_4)$alkyl; wherein the alkyl portions of any of $X^0$, $R^{1'}$ and $R^1$ through $R^8$ are optionally substituted with halogen, carboxy, sulfo, amino, mono- or dialkylamino, alkoxy, cyano, haloacetyl or hydroxy, and the alkyl portions of the substituents have from 1 to 6 carbon atoms; and the aryl portions of any of $X^0$, $R^{1'}$ and $R^1$ through $R^8$ are optionally substituted with from one to four substituents selected from the group consisting of halogen, cyano, carboxy, sulfo, hydroxy, amino, mono- or di$(C_1-C_6)$alkylamino, $(C_1-C_6)$alkyl, $(C_1-C_6)$alkylthio and $(C_1-C_6)$alkoxy; and
- optionally, any two adjacent substituents $X^1$ through $X^4$ can be taken together to form a fused aromatic or heteroaromatic ring that is optionally further substituted with from one to four substituents selected from halogen cyano, carboxy, sulfo, hydroxy, amino, mono- or di$(C_1-C_6)$alkylamino, $(C_1-C_6)$alkyl, $(C_1-C_6)$alkylthio and $(C_1-C_6)$alkoxy.

4. A method in accordance with claim 1, wherein said linking group component comprises two reactive functional groups selected from amino, hydroxy, hydrazino and thiol.

5. A method in accordance with claim 1, wherein said linking group is linear or cyclic or a combination thereof.

6. A method in accordance with claim 1, wherein said linking group comprises a $(C_2-C_{20})$alkylene or $(C_2-C_{20})$heteroalkylene group.

7. A method in accordance with claim 1, wherein said linking group is cyclic and comprises a five-membered heterocycle.

8. A method in accordance with claim 7, wherein said cyclic linking group is a prolinol linker.

* * * * *

UNITED STATES PATENT AND TRADEMARK OFFICE
CERTIFICATE OF CORRECTION

| | | |
|---|---|---|
| PATENT NO. | : 6,972,339 B2 | |
| APPLICATION NO. | : 10/026374 | |
| DATED | : December 6, 2005 | |
| INVENTOR(S) | : Eugeny A. Lukhtanov et al. | |

It is certified that error appears in the above-identified patent and that said Letters Patent is hereby corrected as shown below:

Column 82, at line 44, replace "$(C_2-C_8)$" with --$(C_1-C_8)$--.

Signed and Sealed this

Twenty-seventh Day of November, 2007

JON W. DUDAS
*Director of the United States Patent and Trademark Office*